United States Patent
Boyaka

(10) Patent No.: US 10,286,068 B2
(45) Date of Patent: May 14, 2019

(54) METHODS TO IMPROVE INDUCTION OF IGA ANTIBODIES BY VACCINES

(71) Applicant: OHIO STATE INNOVATION FOUNDATION, Columbus, OH (US)

(72) Inventor: Prosper Boyaka, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 15/566,884

(22) PCT Filed: Apr. 15, 2016

(86) PCT No.: PCT/US2016/027891
§ 371 (c)(1),
(2) Date: Oct. 16, 2017

(87) PCT Pub. No.: WO2016/168696
PCT Pub. Date: Oct. 20, 2016

(65) Prior Publication Data
US 2018/0099043 A1 Apr. 12, 2018

Related U.S. Application Data

(60) Provisional application No. 62/148,044, filed on Apr. 15, 2015.

(51) Int. Cl.
| | | |
|---|---|---|
| A61K 39/00 | (2006.01) | |
| A61K 39/39 | (2006.01) | |
| A61K 39/12 | (2006.01) | |
| A61P 37/04 | (2006.01) | |
| A61P 29/00 | (2006.01) | |
| A61K 9/00 | (2006.01) | |
| A61K 39/02 | (2006.01) | |
| A61K 39/07 | (2006.01) | |

(52) U.S. Cl.
CPC .............. *A61K 39/39* (2013.01); *A61K 9/006* (2013.01); *A61K 9/0019* (2013.01); *A61K 9/0036* (2013.01); *A61K 39/00* (2013.01); *A61K 39/0291* (2013.01); *A61K 39/07* (2013.01); *A61K 39/12* (2013.01); *A61P 29/00* (2018.01); *A61P 37/04* (2018.01); *A61K 2039/541* (2013.01); *A61K 2039/542* (2013.01); *A61K 2039/543* (2013.01); *A61K 2039/55527* (2013.01); *A61K 2039/55561* (2013.01); *A61K 2039/55566* (2013.01); *A61K 2039/6037* (2013.01)

(58) Field of Classification Search
CPC .................................................... A61K 39/39
See application file for complete search history.

(56) References Cited

U.S. PATENT DOCUMENTS

| | | | |
|---|---|---|---|
| 5,145,839 A | * | 9/1992 | Beljanski ............... A61K 31/35 514/27 |
| 8,063,073 B2 | | 11/2011 | Marjana et al. |
| 2011/0280911 A1 | | 11/2011 | Myc et al. |
| 2013/0089570 A1 | | 4/2013 | Ouaked et al. |
| 2013/0149312 A1 | | 6/2013 | Finch et al. |
| 2015/0065414 A1 | | 3/2015 | Long et al. |

OTHER PUBLICATIONS

Siedle et al (Planta Med vol. 73, pp. 401-420) (Year: 2007).*
Betancourt et al (International Journal of Infectious Diseases vol. 11, pp. 394-401) (Year: 2007).*
Kong et al (PNAS vol. 98, No. 20, pp. 11539-11544) (Year: 2001).*
International Search Report and Written Opinion issued for International Application No. PCT/US2016/027891, dated Jul. 22, 2016.
International Preliminary Report on Patentability issued for International Application No. PCT/US2016/027891, dated Oct. 26, 2017.
Bonnegarde-Bernard, A. et al. IKKbeta in intestinal epithelial cells regulates allergen-specific IgA and allergic inflammation at distant mucosal sites. Mucosal Immunol. 7, 257-267 (2014).
Boyaka, P. N. et al. Chimeras of labile toxin one and cholera toxin retain mucosal adjuvanticity and direct Th cell subsets via their B subunit. J. Immunol. 170, 454-462 (2003).
Mucosal vaccines: an overview. In Mucosal Immunology, vol. 1 (Mestecky, J. ed), 855-874 (Elsevier, Acadamic Press, San Diego, CA, 2005).
Branzk, N. & Papayannopoulos, V. Molecular mechanisms regulating NETosis in infection and disease. Semin. Immunopathol. 35, 513-530 (2013).
Brereton, C. F. et al. *Escherichia coli* heat-labile enterotoxin promotes protective Th17 responses against infection by driving innate IL-1 and IL-23 production. J. Immunol. 186, 5896-5906 (2011).
Bromander, A. K. et al. Cholera toxin enhances alloantigen presentation by cultured intestinal epithelial cells. Scand. J. Immunol. 37, 452-458 (1993).
Chou, R. C. et al. Lipid-cytokine-chemokine cascade drives neutrophil recruitment in a murine model of inflammatory arthritis. Immunity 33, 266-278 (2010).
Cong, Y et al. Effects of cholera toxin on macro- phage production of co-stimulatory cytokines. Eur. J. Immunol. 31, 64-71 (2001).
Cox, J. C., et al., "Adjuvants-a classification and review of their modes of action",Vaccine 15:248-256 (1997).
Cuburu, N. et al. Sublingual immunization induces broad-based systemic and mucosal immune responses in mice. Vaccine 25, 8598-8610 (2007).

(Continued)

*Primary Examiner* — Albert M Navarro
(74) *Attorney, Agent, or Firm* — Meunier Carlin & Curfman LLC

(57) ABSTRACT

A vaccine composition is disclosed that contains a vaccine antigen and a neutrophil inhibitor in amounts effective to promote an IgA response to the antigen in a subject. Also disclosed is a method for enhancing immune response to a vaccine antigen in a subject that involves co-administering to the subject the vaccine antigen and an adjuvant composition comprising a neutrophil inhibitor in an amount effective to promote an IgA response to the vaccine antigen in the subject.

20 Claims, 35 Drawing Sheets

Specification includes a Sequence Listing.

(56) References Cited

OTHER PUBLICATIONS

Datta, S. K. et al. Mucosal adjuvant activity of cholera toxin requires Th17 cells and protects against inhalation anthrax. Proc. Natl Acad. Sci. USA 107, 10638-10643 (2010).
Defrance, T. et al. Interleukin 10 and transforming growth factor beta cooperate to induce anti-CD40-activated naive human B cells to secrete immunoglobulin A. J. Exp. Med. 175, 671-682 (1992).
Duverger, A. et al. Bacillus anthracis edema toxin acts as an adjuvant for mucosal immune responses to nasally administered vaccine antigens. J. Immunol. 176, 1776-1783 (2006).
Duverger, A. et al. Contributions of edema factor and protective antigen to the induction of protective immunity by Bacillus anthracis edema toxin as an intranasal adjuvant. J. Immunol. 185, 5943-5952 (2010).
Eisenbarth, S. C. et al. Crucial role for the Nalp3 inflammasome in the immunostimulatory properties of aluminium adjuvants. Nature 453, 1122-1126 (2008).
Fong, C. H. et al. An antiinflammatory role for IKKbeta through the inhibition of 'classical' macrophage activation. J. Exp. Med. 205, 1269-1276 (2008).
Gaffen, S. L. Structure and signalling in the IL-17 receptor family. Nat. Rev. Immunol. 9, 556-567 (2009).
Geissmann, F. et al. Blood monocytes consist of two principal subsets with distinct migratory properties. Immunity 19, 71-82 (2003).
Gorio et al., Reparixin, an Inhibitor of CXCR2 Function, Attenuates Inflammatory Responses and Promotes Recovery of Function after Traumatic Lesion to the Spinal Cord. The J of Pharmacology and Experimental Therapeutics 322:3, 973-981, (2007).
Grespan, R. et al. CXCR2-specific chemokines mediate leukotriene B4-dependent recruitment of neutrophils to inflamed joints in mice with antigen-induced arthritis. Arthritis Rheum. 58, 2030-2040 (2008).
Greten, F. R. et al. NF-kappaB is a negative regulator of IL-1beta secretion as revealed by genetic and pharmacological inhibition of IKKbeta. Cell 130, 918-931 (2007).
Grivennikov, S. I. et al. Dangerous liaisons: STAT3 and NF-kappaB collaboration and crosstalk in cancer. Cytokine Growth Factor Rev. 21, 11-19 (2010).
Harrington, L. E. et al. Interleukin 17-producing CD4 þ effector T cells develop via a lineage distinct from the T helper type 1 and 2 lineages. Nat. Immunol. 6, 1123-1132 (2005).
Hatzelman et al., Anti-Inflammatory and Immunomodulatory Potential of the Novel PDE4 Inhibitor Roflumilast in Vitro. The Journal of Pharmacology and Experimental Therapeutics 297:1, 267-279, (2001).
Hsu, H. C. et al. Interleukin 17-producing T helper cells and interleukin 17 orchestrate autoreactive germinal center development in autoimmune BXD2 mice. Nat. Immunol. 9, 166-175 (2008).
Jackson, E. M. et al. Intranasal vaccination with murabutide enhances humoral and mucosal immune responses to a virus-like particle vaccine. PLoS One 7, e41529 (2012).
Jin, J. et al. The kinase TBK1 controls IgA class switching by negatively regulating noncanonical NF-kappaB signaling. Nat. Immunol. 13, 1101-1109 (2012).
Jordan, M. B. et al. Promotion of B cell immune responses via an alum-induced myeloid cell population. Science 304, 1808-1810 (2004).
Kim, P. H. et al. Cholera toxin and cholera toxin B subunit induce IgA switching through the action of TGF-beta 1. J. Immunol. 160, 1198-1203 (1998).
Klezovich-Benard, M. et al. Mechanisms of NK cell-macrophage Bacillus anthracis crosstalk: a balance between stimulation by spores and differential disruption by toxins. PLoS Pathog. 8, e1002481 (2012).
Kool, M. et al. Alum adjuvant boosts adaptive immunity by inducing uric acid and activating inflammatory dendritic cells. J. Exp. Med. 205, 869-882 (2008).

Korn, T et al. IL-17 and Th17 Cells. Annu. Rev. Immunol. 27, 485-517 (2009).
Kraal, G. Nasal-associated lymphoid tissue. In Mucosal Immunology, vol. 1 (Mestecky, J., Lamm, M.E., Strober, W., Bienenstock, J., McGhee, J.R. & Mayer, L. eds), 415-422 (Elsevier, Academic Press, San Diego, CA, 2005).
Lacaille-Dubois, M. A., et al. A review of the biological and pharmacological activities of saponins. Phytomedicine 2:363-386 (1996).
Lapponi, M. J. et al. Regulation of neutrophil extracellular trap formation by anti-inflammatory drugs. J. Pharmacol. Exp. Ther. 345, 430-437 (2013).
Lawrence, T. et al. Possible new role for NF-kappaB in the resolution of inflammation. Nat. Med. 7, 1291-1297 (2001).
Lillard, J. W. et al. Mechanisms for induction of acquired host immunity by neutrophil peptide defensins. Proc. Natl Acad. Sci. USA 96, 651-656 (1999).
Lo, D. D. et al. M cell targeting by a Claudin 4 targeting peptide can enhance mucosal IgA responses. BMC Biotechnol. 12, 7 (2012).
Lycke, N. et al. Cholera toxin promotes B cell isotype differentiation. J. Immunol. 142, 3781-3787 (1989).
Macpherson, A. J. et al. The immune geography of IgA induction and function. Mucosal Immunol. 1, 11-22 (2008).
Maitra, A. et al. Distinct functional motifs within the IL-17 receptor regulate signal transduction and target gene expression. Proc. Natl Acad. Sci. USA 104, 7506-7511 (2007).
Martinez, F. O. et al. Alternative activation of macrophages: an immunologic functional perspective. Annu. Rev. Immunol. 27, 451-483 (2009).
May, M. J. IL-17R signaling: new players get in on the Actl. Nat. Immunol. 12, 813-815 (2011).
McGee, D. W. et al. Transforming growth factor-beta and IL-1 beta act in synergy to enhance IL-6 secretion by the intestinal epithelial cell line, IEC-6. J. Immunol. 151, 970-978 (1993).
Mitsdoerffer, M. et al. Proinflammatory T helper type 17 cells are effective B-cell helpers. Proc. Natl Acad. Sci. USA 107, 14292-14297 (2010).
Moayeri, M. et al. The roles of anthrax toxin in pathogenesis. Curr. Opin. Microbiol. 7, 19-24 (2004).
Munks, M. W. et al. Aluminum adjuvants elicit fibrin-dependent extracellular traps in vivo. Blood 116, 5191-5199 (2010).
Pillinger et al., Modes of action of aspirin-like drugs: Salicylates inhibit Erk activation and integrin-dependent neutrophil adhesion. Proc. Natl. Acad. Sci. 95, 14540-14545, (1998).
Price, K. R., et al. The Chemistry and biological significance of saponins in foods and feedingstuffs. CRC Crit. Rev. Food Sci. Nutr. 26:27-135 (1987).
Raghavan, S. et al. Sublingual immunization protects against Helicobacter pylori infection and induces T and B cell responses in the stomach. Infect. Immun. 78, 4251-4260 (2010).
Roghanian et al., The Antimicrobial/Elastase Inhibitor Elafin Regulates Lung Dendritic Cells and Adaptive Immunity. Am J Respir Cell Mol Biol 34, 634-642, (2006).
Schopke, Th., & Hiller, K., Triterpenoid saponins. Pharmazie 45:313-342 (1990).
Shibata, S., New Natural Products Plant Pharmacological Biological Therapeutical Activity. Proc. Int. Congr. 1st, 177-198 (1977).
Song, J. H. et al. CCR7-CCL19/CCL21-regulated dendritic cells are responsible for effectiveness of sublingual vaccination. J. Immunol. 182, 6851-6860 (2009).
Song, J. H. et al. Sublingual vaccination with influenza virus protects mice against lethal viral infection. Proc. Natl Acad. Sci. USA 105, 1644-1649 (2008).
Tang, W. J. et al. The adenylyl cyclase activity of anthrax edema factor. Mol. Aspects Med. 30, 423-430 (2009).
Vallabhapurapu, S. et al. Regulation and function of NF-kappaB transcription factors in the immune system. Annu. Rev. Immunol. 27, 693-733 (2009).
Yang, C. W. et al. Neutrophils control the magnitude and spread of the immune response in a thromboxane A2-mediated process. J. Exp. Med. 210, 375-387 (2013).

(56) References Cited

OTHER PUBLICATIONS

Yang, C. W. et al. Neutrophils influence the level of antigen presentation during the immune response to protein antigens in adjuvants. J. Immunol. 185, 2927-2934 (2010).

* cited by examiner

FIGURE 4B

METHODS TO IMPROVE INDUCTION OF IGA ANTIBODIES BY VACCINES

CROSS REFERENCE TO RELATED APPLICATIONS

This application is a national stage application filed under 35 U.S.C. § 371 of PCT/US2016/027891 filed Apr. 15, 2016, which claims the benefit of U.S. Provisional Patent Application Ser. No. 62/148,044 filed Apr. 15, 2015, the disclosures of which are expressly incorporated herein by reference.

STATEMENT REGARDING FEDERALLY SPONSORED RESEARCH OR DEVELOPMENT

This invention was made with Government Support under Grants No. R01A1043197 and R01DK101323 awarded by the National Institutes of Health. The Government has certain rights in the invention.

BACKGROUND

Most infectious agents enter the body through mucosal tissues. Unfortunately, very few vaccines induce immunoglobulin-A (IgA), the type of immunoglobulins (antibodies) capable of protecting mucosal sites. Induction of mucosal IgA capable of providing a first line of defense against bacterial and viral pathogens remains a major goal of vaccines given via mucosal routes.

SUMMARY

A subset of myeloid cells is shown herein to provide a signal(s) that limits the ability of B lymphocytes to produce IgA antibodies. Disclosed herein are compositions and methods to limit recruitment of these cells in the sites where antibody responses develop after immunization and/or block the function of these cells and thus, limiting their ability to interfere with production of IgA antibodies by B lymphocytes. The methods described herein are not specific to a single vaccine and are expected to improve induction of IgA by most vaccine formulations regardless of the route of delivery.

A vaccine composition is therefore disclosed that contains a vaccine antigen and a neutrophil inhibitor in amounts effective to promote an IgA response to the antigen in a subject. Also disclosed is an adjuvant composition comprising a neutrophil inhibitor and an adjuvant for combination with a vaccine antigen.

Also disclosed is a method for enhancing immune response to a vaccine antigen in a subject that involves co-administering to the subject the vaccine antigen and an adjuvant composition comprising a neutrophil inhibitor in an amount effective to promote an IgA response to the vaccine antigen in the subject.

In some embodiments, the disclosed compositions and methods can be used to make nearly any vaccine a good inducer of IgA antibodies. For example, in some cases, the disclosed compositions and methods can be used to enhance or induce an IgA response for any vaccine antigen that is known to promote an IgG response in a subject. Therefore, the vaccine antigen can be a bacterial or viral antigen. Other useful antigens include protozoa, fungi, helminth, and ectoparasites.

In some embodiments, the disclosed adjuvant composition induces antigen-specific IgA in both the serum and mucosal secretions. Currently only vaccines given via mucosal routes (oral or intranasal) have the potential to induce mucosal IgA (i.e., if they contain appropriate adjuvants). In some embodiments, the disclosed adjuvant can enhance the ability of the vaccine antigen to induce IgA response in the mucosa when they are administered to a mucosal surface, such as by oral or intranasal administration. However, in other embodiments, the disclosed adjuvant allows induction of mucosal IgA for vaccines administered by other routes, such as by intramuscular or subcutaneous injection, by topical application under the tongue (sublingual), on the skin (i.e., epicutaneous as a patch), or by intravaginal administration.

The disclosed adjuvant can be co-administered with the vaccine antigen, e.g., in the same composition or contemporaneously by the same route of administration. In other embodiments, the disclosed adjuvant is administered contemporaneously by an alternative route of administration, e.g., intranasally for an injected vaccine or by injection for an intranasal vaccine. In other embodiments, the vaccine antigen is administered prior to the adjuvant composition. In an alternative embodiment, the vaccine antigen is administered after the adjuvant composition.

In some embodiments, the neutrophil inhibitor of the disclosed adjuvant is any agent that inhibits neutrophil elastase, phosphodiesterase type 4, neutrophil extracellular trap (NET), or neutrophil recruitment.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A shows flow cytometry analysis of total myeloid cells. Top: absolute number; Bottom: frequency of CD11b$^+$ cells. FIG. 1B shows gating strategy for identification of myeloid cell subsets. FIG. 1C shows detailed flow cytometry analysis of myeloid cell subsets. FIG. 1D shows radar plots to summarize the profile of myeloid cell subsets in sublingual tissues. Data are expressed as mean±s.d. (n=3). *p≤0.05 compared with PBS.

FIG. 2A is a representative Western-blot picture (from three independent experiments) of 1-actin and overall (cytoplasmic and nuclear) phospho-NF-κB p65 (pNF-κB p65), and pSTAT3 levels in sublingual tissues 1 and 2 h after administration of EdTx.

FIGS. 2B and 2C show flow cytometry analysis of myeloid cells (FIG. 2B) and cell subsets (FIG. 2C) 3 and 6 h after sublingual application of EdTx. All data are expressed as mean±s.d. (n=3). *p≤0.05 compared with PBS, and ▼p≤0.05 compared with C57BL/6.

FIG. 3A shows gating strategy for identification of chemoattractant receptors on myeloid cell subsets. FIG. 3B shows percentage of receptor-positive cells. FIG. 3C are pie diagrams of relative expression of individual receptors were generated using the formula: Relative number=(% positive cells for a receptor×1/sum of % positive cells for all receptors)×100. Data are expressed as mean±s.d. (n=4). *p≤0.05 receptor expression compared with C57BL/6 mice and ▼p≤0.05 compared with other receptors in the same group.

FIGS. 4A to 4C show lack of IKKβ signaling in myeloid cells improves the adjuvant activity of edema toxin (EdTx) after sublingual immunization and promotes antigen-specific secretory immunoglobulin-A (SIgA) responses. Mice were immunized three times at weekly intervals by sublingual application of the *Yersinia pestis* antigen F1-V alone or F1-V plus EdTx as an adjuvant. Serum, vaginal washes, and fecal samples were collected 1 week (Day 21), and saliva samples were collected 2 weeks (Day 28) after the last immunization. F1-V-specific Ab responses were analyzed by enzyme-linked immunosorbent assay (ELISA). FIGS. 4A and 4B show F1-V-specific serum antibody responses (FIG. 4A) and F1-V-specific SIgA responses in mucosal secretions (FIG. 4B). The end-point titers were expressed as Log 2 GMTs.±s.d. from C57BL/6 (n=5), and IKKβ$^{\Delta M ye}$ mice (n=3-5). *p≤0.05 compared with C57BL/6 mice and ▼p≤0.05 compared with group immunized with F1-V alone. FIG. 4C shows F1 epitope-specific serum IgG responses in C57BL/6 (n=5) and IKKβ$^{\Delta M ye}$ mice (n=5). Sera were diluted 1:50 (groups immunized with F1-V alone) or 1:500 (groups immunized with F1-V plus EdTx), and IgG responses against linear epitopes of the capsular F1 antigen were analyzed by epitope-specific ELISA. Results were expressed as mean $OD_{405\ nm}$±s.d. *p≤0.05 compared with group immunized with F1-V alone.

FIG. 6A shows flow cytometry analysis of myeloid cell subsets. FIG. 6B shows CLN cells further cultured for 3 days in the presence of lipopolysaccharide (5 µg ml$^{-1}$) and Ab-secreting cells analyzed by ELISPOT. FIG. 6C shows linear regression models to correlate the frequency of neutrophils and number of Ig isotype-secreting cells. Data are expressed as mean±s.d. (n=4). *p≤0.05 compared with C57BL/6. In FIG. 6D, wild-type C57BL/6 mice treated by IP administration of the neutrophil Ly6G-specific 1A8 monoclonal Ab (1A8$^+$ C57BL/6 mice). Two days later, control C57BL/6 and IKKβ$^{\Delta M ye}$ mice were immunized three times at weekly intervals by sublingual application of F1-V plus EdTx. F1-V-specific IgA Ab responses in serum and fecal samples were analyzed by enzyme-linked immunosorbent assay (ELISA) and endpoint titers were expressed as $Log_2$GMTs.±s.d. *p≤0.05 compared with C57BL/6 in each day (n=5).

In FIG. 7A, CD11b$^-$ spleen cells from C57BL/6 mice were co-cultured with autologous CD11b$^+$ cells from C57BL/6 mice or heterologous CD11b$^+$ IKKβ$^{\Delta M ye}$ cells in the presence of lipopolysaccharide (LPS; 5 µg ml$^{-1}$) with or without edema toxin (EdTx; 2 µg ml$^{-1}$). The frequencies of expression of IgA$^+$ among B220$^+$ IL-17RA$^{low}$ and B220$^+$ IL-17RA$^{high}$ subpopulations were analyzed by flow cytometry after 5 days of co-culture with autologous or heterologous CD11b$^+$ cells. Data are expressed as mean±s.d. (n=4). *p≤0.05 compared with C57BL/6 CD11b$^+$ cells. In FIGS. 7B and 7C, CD19$^+$ splenocytes from C57BL/6 mice were incubated overnight with 100 ng ml$^{-1}$ of LPS, washed extensively and then co-cultured with autologous neutrophils from C57BL/6 mice or heterologous neutrophils from IKKβ$^{\Delta M ye}$ mice without additional stimuli. FIG. 7B shows IgM, IgG, and IgA levels in 5-day culture supernatants as determined by enzyme-linked immunosorbent assay. Data are expressed as mean±s.d. (n=4). *p≤0.05 compared with CD19$^+$ B cells cultured alone. (c, d) Messenger RNA (mRNA) levels of IgA heavy chain determined by realtime reverse transcriptase-PCR after 24 h of co-culture. FIG. 7C shows individual mRNA levels in three independent experiments. FIG. 7D shows relative mRNA levels from co-culture of B cells with neutrophils as a percentage of mRNA levels in cultures of CD19$^+$ B cells alone (n=3). *p≤0.05 compared with CD19$^+$ B cells cultured alone.

FIG. 8A shows gating strategy for identification of myeloid cell subsets, i.e., F4/80$^-$ cells for neutrophils (I) and F4/80$^+$ cells for the other myeloid subsets (II). FIG. 8B shows Geimsa staining and representative flow cytometry plots (SSC×FSC) of representative myeloid-lineage cells found in sublingual tissues of mice. FIG. 8C shows characteristic side scatter (SSC) of myeloid cell subsets. All data are expressed as mean±SD (n=6). *p≤0.05.

FIG. 9A shows densitometry analysis of pNF-κB p65 and pSTAT3 protein in sublingual tissues 1 and 2 hours after administration of EdTx as normalized with β-actin. FIG. 9B shows variation of pSTAT3 and phosphoNF-κB p65 expression before (PBS) and 2 hours after administration of EdTx. Data are expressed as mean relative relative densitometry units±SD (n=3).

FIG. 12A shows PA-specific IgG responses measured by ELISA. The end-point titers were expressed as $Log_2$ GMTs.±SD from C57BL/6 (n=5), and IKKβ$^{ΔMye}$ mice (n=5). *p≤0.05 compared with C57BL/6. FIG. 12B shows PA-specific neutralizing Ab titers determined by in vitro toxicity assay. Neutralizing Ab titers are expressed as $Log_2$ GMTs.±SD from C57BL/6 (n=5), and IKKβ$^{ΔMye}$ mice (n=5). *p≤0.05 compared with control C57BL/6 mice.

FIG. 14A shows the percentage of CD11b$^-$F4/80$^-$Gr-1$^{high}$ (neutrophils) in the cervical lymph nodes was analyzed 1 (D1), 2 (D2) or 3 (D3) days later by flow cytometry. FIG. 14B shows the percentages of myeloid subsets in the sublingual tissues were analyzed by flow cytometry 3 hours after sublingual administration of PBS and EdTx (15 μg) in mice pretreated by ip injection of 1A8 (1A8=EdTx) or not (EdTx). Results are expressed as mean±SD (n=3).

FIG. 15A shows B cell (B220+) populations based on IL-17RA expression. FIG. 15B shows frequency of B220$^+$IL-17RA$^{low}$ and B220$^+$IL-17RA$^{high}$. FIG. 15C shows APRIL, BAFF, and AID mRNA responses. Spleen cells from C57BL/6 mice were depleted of CD11b cells (CD11b$^-$ spleen) and cultured for 24 hours at 37° C. with either autologous CD11b$^+$ cells from C57BL/6 or heterologous CD11b$^+$ cells from IKKβ$^{ΔMye}$ mice (IKKβ$^{ΔMye}$ CD11b$^+$ cells) in the presence or absence of EdTx (2 μg/ml). mRNA levels were determined by real time RT-PCR. Data are expressed as mean±SD and are representative of three independent experiments. *p≤0.05 compared with C57BL/6 CD11b$^+$ cells, and ▼p≤0.05 compared with co-culture in the absence of EdTx.

Figure 1A:
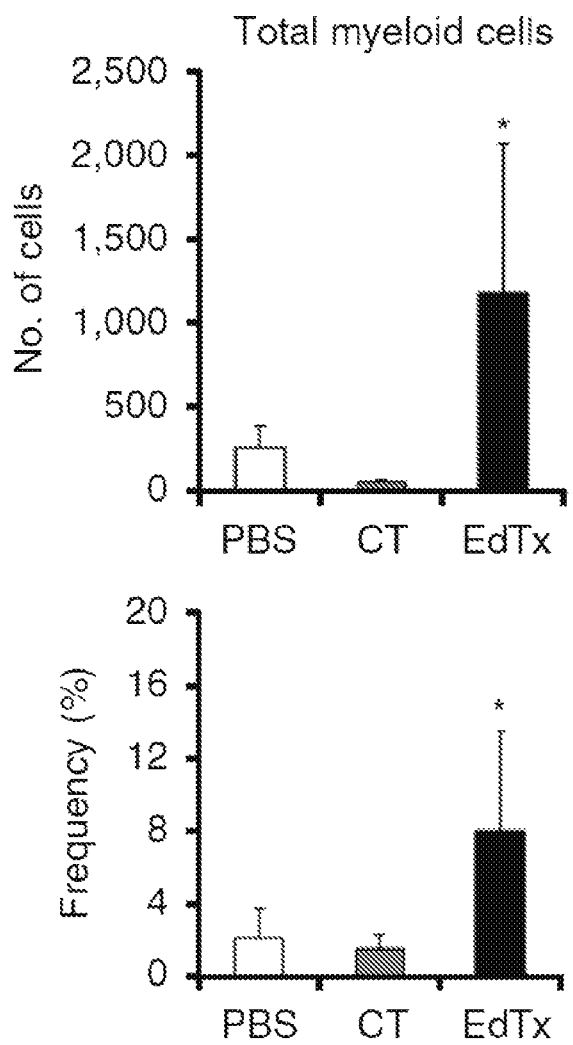
FIGS. 1A to D show *cholera* toxin and *Bacillus anthracis* edema toxin promote different profiles of myeloid cell subsets in sublingual tissues. Sublingual tissues were collected 3 h after sublingual administration of phosphate-buffered saline (PBS), *cholera* toxin (CT) (2 µg) or *Bacillus anthracis* edema toxin (EdTx) (15 µg).
Figure 1B:
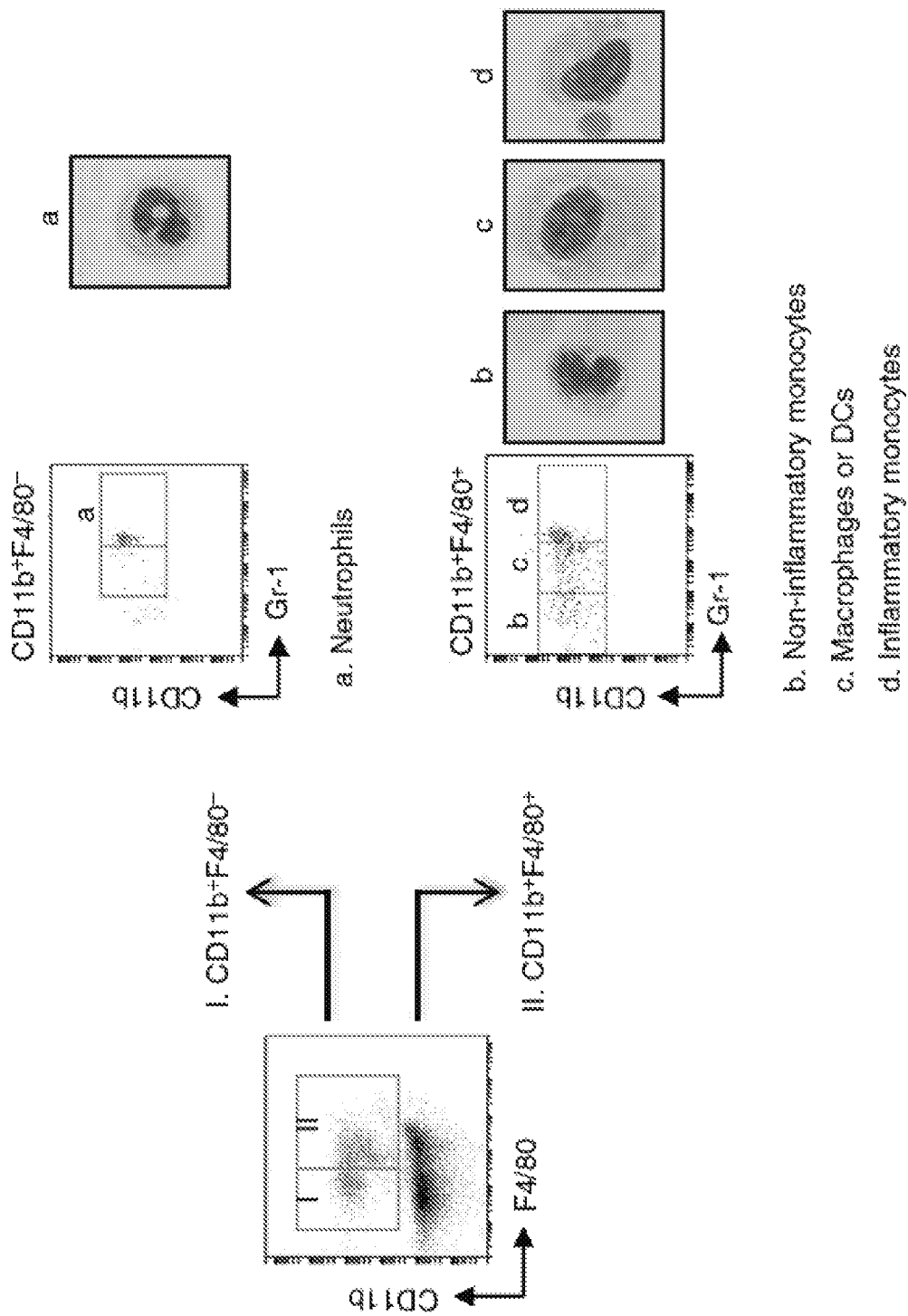
Figure 1C:
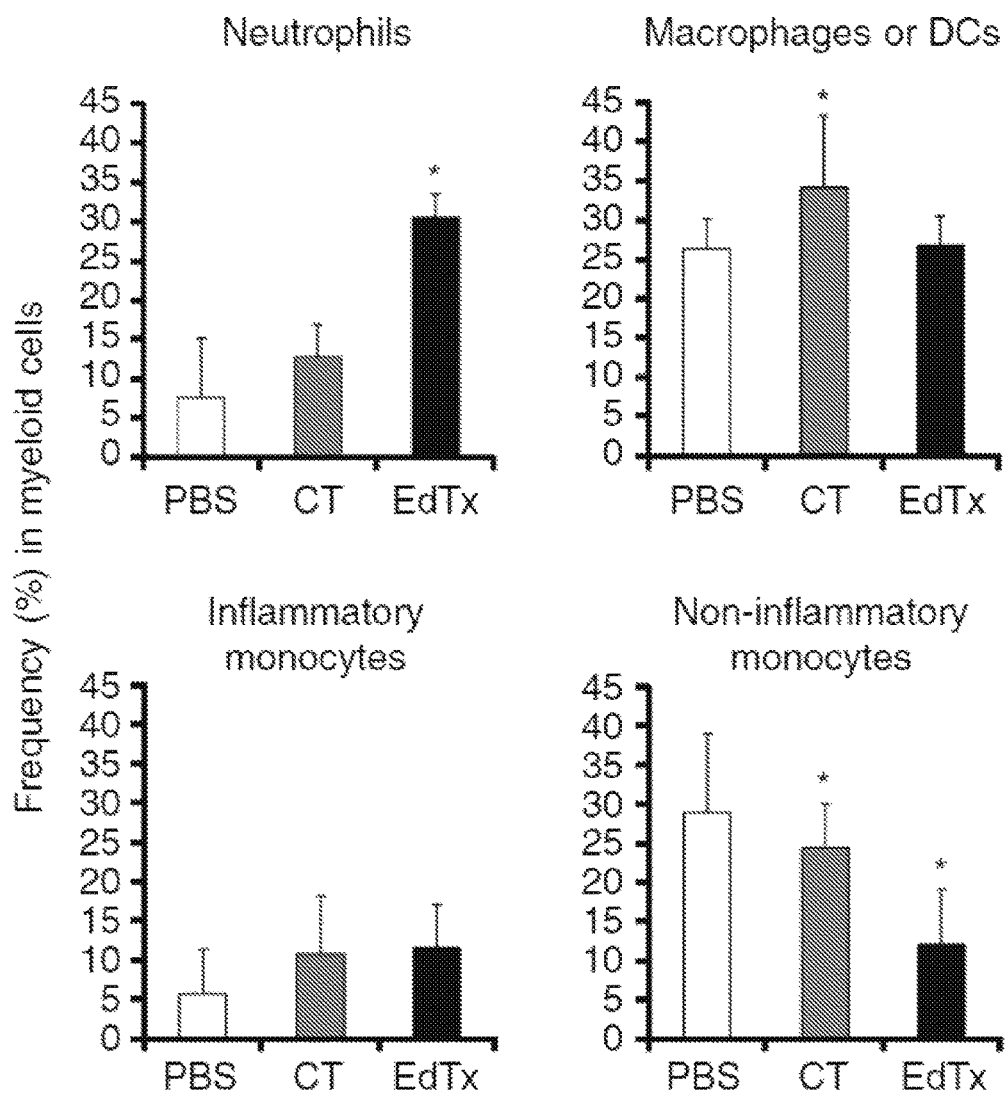
Figure 1D:
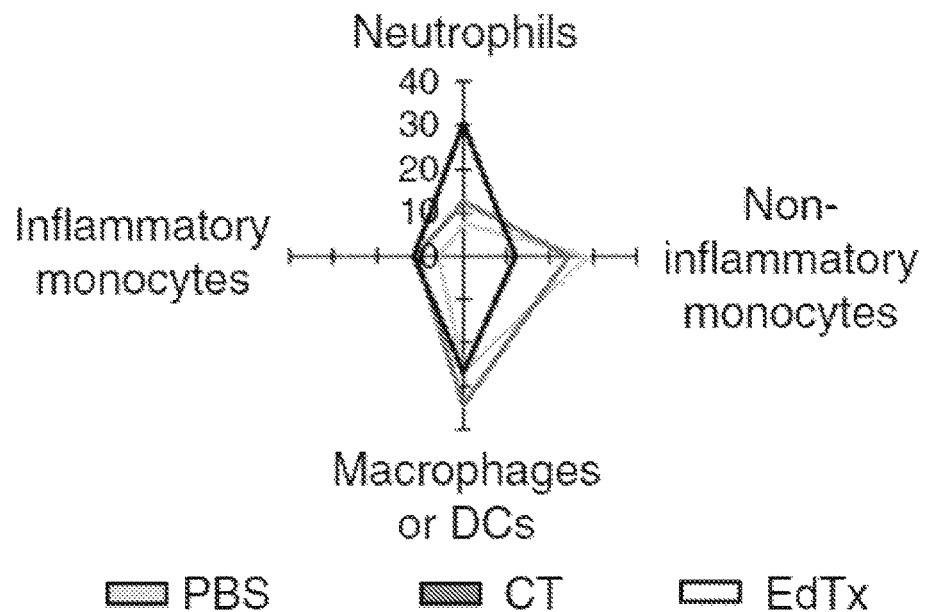

In some embodiments, the neutrophil inhibitor is any agent that inhibits phosphodiesterase type 4 (PDE4). Examples of PDE4 inhibitors include Apremilast (Otezla®), Cilomilast (Ariflo®, SB-207,499), Diazepam (Valium®), Ibudilast (AV-411, MN-166), Luteolin, Mesembrenone, Piclamilast (RP 73401), Roflumilast (Daxas®, Daliresp®), and Rolipram.

In some embodiments, the neutrophil inhibitor is any agent that inhibits neutrophil extracellular trap (NET), such as sulfasalazine (Azulfidine®, Salazopyrin®, Sulazine®) or thalidomide (Immunoprin®, Talidex®, Talizer®, Thalomid®). Extracellular trap formation (ETosis) is a recently discovered form of cell death distinct from necrosis or apoptosis where a lattice of DNA strands is extruded from innate immune cells. Sulfasalazine and thalidomide have been shown to significantly inhibit ET formation in neutrophils and mast cells in a dose-dependent fashion.

In some embodiments, the neutrophil inhibitor is any agent that inhibits neutrophil recruitment. For example, the neutrophil inhibitor can be a CXCR1/2 antagonist, such as reparixin.

In some embodiments, the neutrophil inhibitor is any agent that inhibits IL-1R. For example, the IL-1R inhibitor can be anakinra (Kineret®). Anakinra blocks the biologic activity of naturally occurring IL-1, including inflammation and cartilage degradation associated with rheumatoid arthritis, by competitively inhibiting the binding of IL-1 to the Interleukin-1 type receptor, which is expressed in many tissues and organs.

In some embodiments, the neutrophil inhibitor is a non-steroidal anti-inflammatory drug (NSAID). NSAIDS include Salicylates, such as Aspirin (acetylsalicylic acid), Diflunisal (Dolobid®), Salicylic acid and other salicylates, and Salsalate (Disalcid); N-acetyl-para-aminophenol (APAP) derivatives, such as acetaminophen/paracetamol (Tylenol®); Propionic acid derivatives, such as Ibuprofen (Advil®, Motrin®, Nuprin®, and Medipren®), Dexibuprofen, Naproxen (Aleve®, Anaprox®, Antalgin®, Feminax Ultra®, Flanax®, Inza®, Midol® Extended Relief, Nalgesin®, Naposin®, Naprelan®, Naprogesic®, Naprosyn®, Naprosyn® suspension, EC-Naprosyn®, Narocin®, Proxen®, Synflex® and Xenobid®), Fenoprofen, Ketoprofen, Dexketoprofen, Flurbiprofen, Oxaprozin, and Loxoprofen; Acetic acid derivatives, such as Indomethacin (Indocin®), Tolmetin, Sulindac, Etodolac, Ketorolac, Diclofenac, Aceclofenac, and Nabumetone (Relafen®, Relifex®, Gambaran®); Enolic acid (Oxicam) derivatives, such as Piroxicam, Meloxicam, Tenoxicam, Droxicam, Lornoxicam, and Isoxicam; Anthranilic acid derivatives (Fenamates), such as Mefenamic acid, Meclofenamic acid, Flufenamic acid, and Tolfenamic acid; Selective COX-2 inhibitors (Coxibs), such as Celecoxib, Rofecoxib, Valdecoxib, Parecoxib, Lumiracoxib, Etoricoxib, and Firocoxib; and Sulfonanilides, such as Nimesulide.

In some embodiments, when an NSAID is used as neutrophil inhibitor, it is added to the organism or material that contains an antigen and co-administered by intranasal route, intramuscular or subcutaneous injection, or topical application under the tongue (sublingual) or on the skin (i.e., epicutaneous as a patch).

Antigens

In some embodiments, the disclosed compositions and methods can be used to enhance or induce an IgA response for any vaccine antigen that is known to promote an IgG response in a subject. Therefore, the vaccine antigen can be a bacterial or viral antigen.

Vaccines antigens for use in the disclosed compositions and methods can include one or more bacterial antigens from a particular bacteria. Bacteria for which vaccines can be formulated include, but are not limited to: *Helicobacter pylori, Chlamydia pneumoniae, Chlamydia trachomatis, Ureaplasma urealyticum, Mycoplasma pneumoniae, Staphylococcus* spp., *Staphylococcus aureus, Streptococcus* spp., *Streptococcus pyogenes, Streptococcus pneumoniae, Streptococcus viridans, Enterococcus faecalis, Neisseria meningitidis, Neisseria gonorrhoeae. Bacillus anthracis, Salmonella* spp., *Salmonella typhi, Vibrio cholera, Pasteurella pestis, Pseudomonas aeruginosa, Campylobacter* spp., *Campylobacter jejuni, Clostridium* spp., *Clostridium difficile, Mycobacterium* spp., *Mycobacterium tuberculosis, Treponema* spp., *Borrelia* spp., *Borrelia burgdorferi, Leptospira* spp., *Hemophilus ducreyi, Corynebacterium diphtheria, Bordetella pertussis, Bordetella parapertussis, Bordetella bronchiseptica, hemophilus influenza, Escherichia coli. Shigella* spp., *Erlichia* spp., *Rickettsia* spp., *Yersinia pestis, Yersinia enterocolitica*. Bacterial antigens can be native, recombinant or synthetic. Such bacterial antigens include, but are not limited to, selectins or lectins from bacteria that bind to carbohydrate determinants present on cell surfaces; and bacteria receptors for proteins, such as fibronectin, laminin, and collagens.

Vaccines antigens for use in the disclosed compositions and methods can include one or more antigens from a particular virus to form a vaccine. Viruses for which vaccines can be formulated include, but are not limited to: Influenza viruses, Parainfluenza viruses, Mumps virus, Adenoviruses, Respiratory syncytial virus, Epstein-Barr virus, Rhinoviruses, Polioviruses, Coxsackieviruses, Echoviruses, Rubeola virus, Rubella virus, Varicell-zoster virus, Herpes viruses (human and animal), Herpes simplex virus, Parvoviruses (human and animal), Cytomegalovirus, Hepatitis viruses, Human papillomavirus, Alphaviruses, Flaviviruses, Bunyaviruses, Rabies virus, Arenaviruses, Filoviruses, HIV 1, HIV 2, HTLV-I, HTLV-II, FeLV, Bovine LV, FeIV, Canine distemper virus, Canine contagious hepatitis virus, Feline calicivirus, Feline rhinotracheitis virus, TGE virus (swine), and Foot and mouth disease virus. Viral antigens can be native, recombinant or synthetic. Such viral antigens include, but are not limited to, viral proteins that are responsible for attachment to cell surface receptors to initiate the infection process, such as (i) envelope glycoproteins of retroviruses (HIV, HTLV, FeLV and others) and herpes viruses, and (ii) the neuramidase of influenza viruses. Additionally, peptides derived from such viral proteins can be employed, either free, or associated non-covalently, or conjugated covalently to a suitable carrier.

Additional Adjuvants

In some embodiments, the disclosed adjuvant is used in combination with one or more other adjuvants. Adjuvants that have been used to enhance an immune response include aluminum compounds (all generally referred to as "alum"), oil-in-water emulsions (often containing other compounds), Freund's adjuvant (CFA or IFA), an oil-in-water emulsion containing dried, heat-killed *Mycobacterium tuberculosis* organisms), and pertussis adjuvant (a saline suspension of killed *Bordetella pertussis* organisms). These adjuvants generally are thought to have their mechanism of action by causing a depot of antigen and permitting a slow release of the antigen to the immune system, and by producing non-specific inflammation thought to be responsible for their observed activity (Cox, J. C., et al., Vaccine 15:248-256 (1997)). Some saponins have been shown to have different types of immune stimulating activities, including adjuvant activity. These activities have been reviewed previously (Shibata, S., New Nat. Prod. Plant Pharmacol. Biol. Ther. Act., Proc. Int. Congr. 1st, 177-198 (1977); Price, K. R., et al. CRC Crit. Rev. Food Sci. Nutr. 26:27-135 (1987); Schopke, Th., & Hiller, K., Pharmazie 45:313-342 (1990); Lacaille-Dubois, M. A., et al., Phytomedicine 2:363-386 (1996).

Adjuvant could also consist of bacterial toxin derivatives either as subunit of toxins or detoxified derivatives of bacterial toxins, DNA with or without CpG oligodeoxynucleotides (ODN) (TLR9 ligands), or cyclic dinucleotides (STING ligands).

In some cases, the additional adjuvant is an aluminium salt (i.e., alum), TLR9 agonists (i.e., CpG oligodeoxynucleotides (ODN), TLR4 agonist (i.e., Monophosphoryl lipid A or MPL), agonist of other TLR molecules (i.e., TLR3 or TLR5), or a squalene-based oil-in-water emulsion (i.e., AS03, MF59).

Pharmaceutical Compositions

Disclosed is a pharmaceutical compositions containing therapeutically effective amounts of one or more of the disclosed adjuvants and a pharmaceutically acceptable carrier. Pharmaceutical carriers suitable for administration of the adjuvants provided herein include any such carriers known to those skilled in the art to be suitable for the particular mode of administration.

In addition, the adjuvants may be formulated as the sole active ingredient in the composition or may be combined with other active ingredients.

The compositions contain one or more adjuvants provided herein and may also contain one more vaccine antigens, as provide herein. The adjuvants are, in one embodiment, formulated into suitable pharmaceutical preparations such as solutions, suspensions, tablets, dispersible tablets, pills, capsules, powders, sustained release formulations or elixirs, for oral or sublingual administration or in sterile solutions or suspensions for parenteral administration, as well as transdermal patch preparation and dry powder inhalers. In one embodiment, the adjuvants described above are formulated into pharmaceutical compositions using techniques and procedures well known in the art (See, e.g., Ansel, Introduction to Pharmaceutical Dosage Forms, 4th Edition, 1985, 126).

In one embodiment, the compositions are formulated for single dosage administration. To formulate a composition, the weight fraction of compound is dissolved, suspended, dispersed or otherwise mixed in a selected carrier at an effective concentration such that the treated condition is relieved or one or more symptoms are ameliorated.

The adjuvant is included in the pharmaceutically acceptable carrier in an amount sufficient to exert a therapeutically useful effect in the absence of undesirable side effects on the subject or patient treated. The therapeutically effective concentration may be determined empirically by testing the compounds in in vitro, ex vivo and in vivo systems, and then extrapolated therefrom for dosages for the subject or patient.

The concentration of adjuvants in the pharmaceutical composition will depend on absorption, inactivation and excretion rates of the adjuvants, the physicochemical characteristics of the adjuvants, the dosage schedule, and amount administered as well as other factors known to those of skill in the art.

Pharmaceutical dosage unit forms are prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

In instances in which the adjuvants exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrin derivatives, sorbitan monolaurate, triethanolamine sodium acetate, triethanolamine oleate, and other such agents.

In one embodiment, the adjuvant is administered in a dose equivalent to parenteral administration of about 0.1 ng to about 100 g per kg of body weight, about 10 ng to about 50 g per kg of body weight, about 100 ng to about 1 g per kg of body weight, from about 1 µg to about 100 mg per kg of body weight, from about 1 µg to about 50 mg per kg of body weight, from about 1 mg to about 500 mg per kg of body weight; and from about 1 mg to about 50 mg per kg of body weight. Alternatively, the amount of adjuvant administered to achieve a therapeutic effective dose is about 0.1 ng, 1 ng, 10 ng, 100 ng, 1 µg, 10 µg, 100 µg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

Administration

The disclosed adjuvant compositions can be administered topically (patch), orally, parenterally, rectally, sublingually, by intravaginal administration, by inhalation or by direct gene transfer. The term "parenteral" includes subcutaneous injections, intravenous, intramuscular, intracisternal injection, or infusion techniques. Administration of the disclosed adjuvant can be done prior to, concurrent with or subsequent to the administration of the vaccine to the host. In any of the slow, controlled or sustained release formulations, the disclosed adjuvant will normally be administered concurrently with the vaccine, although the release characteristics of the disclosed adjuvant and the vaccine may differ in vivo. The disclosed adjuvant can be administered from 5 days prior to vaccine administration to about 30 days post vaccine administration. Such compositions will typically contain an immunogenicity-augmenting amount of the disclosed adjuvant, alone or in combination with an effective amount of any other active material. The dosages and desired drug concentrations contained in the compositions may vary depending upon many factors, including the intended use, patient's body weight and age, and route of administration. Preliminary doses can be determined according to animal tests, and the scaling of dosages for administration can be performed according to art-accepted practices without undue experimentation.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Neutrophils Negatively Regulate Induction of Mucosal IgA Responses after Sublingual Immunization

INTRODUCTION

Mucosal surfaces are constantly exposed to microorganisms and represent the main portal of entry of pathogens and toxins. Mucosal immunoglobulin-A (IgA) or secretory IgA (SIgA) neutralizes pathogenic microorganisms and toxins, interferes with bacterial or viral colonization of the epithelium, and participates in homeostasis of mucosal tissues (Macpherson, A. J., et al. Mucosal Immunol. 1, 11-22 (2008)). Ideally, vaccines capable of promoting both IgG in the bloodstream and SIgA in mucosal tissues would provide two layers of defense for optimal protection against infectious agents. Injected vaccines containing alum, the most widely used adjuvant, induce serum IgG responses, but unlike experimental mucosal adjuvants, fails to promote SIgA responses (Jackson, E. M., et al. PLoS One 7, e41529 (2012); Lo, D. D., et al. BMC Biotechnol. 12, 7 (2012)). Cholera toxin (CT) and the related heat labile toxin (LT) I of Escherichia coli are the most studied experimental adjuvants for induction of SIgA, however, their inherent toxicity precludes their use in oral or nasal vaccines.

Cytokines play a crucial role in shaping the profile of T-helper (Th) cytokine responses as well as the Ig isotype and subclass responses. Previous studies have shown that the mucosal adjuvant CT induces pro-inflammatory cytokine (i.e., interleukin-6 (IL-6) or IL-13) secretion by antigen-presenting cells (i.e., macrophages and dendritic cells) (Cong, Y., et al. Eur. J. Immunol. 31, 64-71 (2001); Datta, S. K., et al. Proc. Natl Acad. Sci. USA 107, 10638-10643 (2010)). CT also induces transforming growth factor beta (TGF-β) and IL-10, two anti-inflammatory cytokines that play a central role in the induction of SIgA (Datta, S. K., et al. Proc. Natl Acad. Sci. USA 107, 10638-10643 (2010); Defrance, T., et al. J. Exp. Med. 175, 671-682 (1992); Kim, P. H., et al. J. Immunol. 160, 1198-1203 (1998)). Studies with live bacterial and viral vectors as well as immunization studies with Th1-inducing cytokines (i.e., IL-12 and IL-18) have now established that SIgA can also be induced in the context of Th1-biased responses. More recently, the ability of CT as an adjuvant to promote SIgA responses was shown to be impaired in mice lacking IL-17A, suggesting a role for IL-17A or related signaling in SIgA responses. 6 In this regard, differentiation of Th17 cells requires IL-1β, IL-6, and TGF-β (Datta, S. K., et al. Proc. Natl Acad. Sci. USA 107, 10638-10643 (2010); Harrington, L. E., et al. Nat. Immunol. 6, 1123-1132 (2005)), which are cytokines that support IgA responses. Unlike Th1 and Th2 cytokines, which activate JAK-STAT signaling pathways, signaling through IL-17R activates Act1 for subsequent activation of the classical nuclear factor kB (NF-κB) signaling pathway (Gaffen, S. L., et al. Nat. Rev. Immunol. 9, 556-567 (2009)). Furthermore, IL-17A directly triggers Ig class switching to IgG2a and IgG3, but not to IgG1 (Mitsdoerffer, M., et al. Proc. Natl Acad. Sci. USA 107, 14292-14297 (2010)). To our knowledge, it is still unclear whether production of IgA is directly regulated by IL-17A/IL-17RA signaling in B cells. The NF-κB pathway plays an important role in inflammatory responses and a number of stimuli can lead to NF-κB translocation to the nucleus (Vallabhapurapu, S., et al. Annu. Rev. Immunol. 27, 693-733 (2009)). Previous studies have shown that the NF-κB pathway can mediate both pro- and anti-inflammatory effects (Greten, F. R., et al. Cell 130, 918-931 (2007); Lawrence, T., et al. Nat. Med. 7, 1291-1297 (2001)) depending on the immune cells in which the IKKβ-NF-κB signaling occurs (Fong, C. H., et al. J. Exp. Med. 205, 1269-1276 (2008)) and stimuli to which they are exposed. A recent study showed a link between activation of the non-canonical NF-kB pathway in B cells and their ability to undergo immunoglobulin class switch for the production of IgA (Jin, J., et al. Nat. Immunol. 13, 1101-1109 (2012)). However, it remains unclear if IKKβ-dependent signaling in myeloid cells regulates IgA responses to mucosal vaccination.

Sublingual tissues have been used as a delivery site for bacterial and viral vaccines (Raghavan, S., et al. Infect. Immun. 78, 4251-4260 (2010), Song, J. H., et al. Proc. Natl Acad. Sci. USA 105, 1644-1649 (2008)), and cervical lymph nodes (CLNs) were identified as the primary site of antigen presentation after sublingual immunization (Song, J. H., et al. J. Immunol. 182, 6851-6860 (2009)). However, how innate immune cells in sublingual tissues and/or CLNs regulate antibody production remains unknown. Edema toxin (EdTx) is one of the exotoxins produced by the Gram-positive, spore-forming rod Bacillus anthracis (Moayeri, M., et al. Curr. Opin. Microbiol. 7, 19-24 (2004)). EdTx is composed of two subunits: a binding subunit and an enzymatic subunit. The binding subunit, or protective Ag (PA), allows the binding of these toxins to the anthrax toxin receptors that are expressed by most cells. The enzymatic subunit, or edema factor, is a calmodulin- and calcium-dependent adenylate cyclase that catalyzes the conversion of ATP to cyclic AMP (Moayeri, M., et al. Curr. Opin. Microbiol. 7, 19-24 (2004); Tang, W. J., et al. Mol. Aspects Med. 30, 423-430 (2009)). We previously showed that EdTx is a mucosal adjuvant that promotes mucosal and systemic immunity to intranasally co-administered vaccine antigens (Duverger, A., et al. J. Immunol. 185, 5943-5952 (2010); Duverger, A., et al. J. Immunol. 176, 1776-1783 (2006)). Here we addressed the contribution of monocytes/macrophages to mucosal SIgA responses after sublingual immunization. Using B. anthracis EdTx as a model of vaccine adjuvant to target anthrax toxin receptors, we show a previously unknown role of neutrophils as negative regulators of IgA responses. Thus, recruitment of neutrophils into sublingual tissues and CLNs shortly after sublingual immunization impaired the development of IgA responses. The negative role of neutrophils in IgA responses was confirmed in vivo by depletion of neutrophils before immunization with EdTx and in vitro by co-culture of B cells with neutrophils.

Methods

Mice.

Control C57BL/6 mice were obtained from The Jackson Laboratory (Bar Harbor, Me.) or NCI-Frederick (Frederick, MD) and acclimated to our facility for at least 2 weeks before being used. IKKβ$^{\Delta M y e}$ mice were kindly provided by Dr Karin (University of California at San Diego) and were generated by crossing LysMCre mice, expressing Cre downstream of the lysozyme promoter in myeloid-lineage cells, with IKKβ$^{f/f}$ mice harboring a loxP-flanked IKKβ gene (Greten, F. R., et al. Cell 130, 918-931 (2007), Lawrence, T., et al. Nat. Med. 7, 1291-1297 (2001)). Mice were bred in our facility, maintained in a pathogen-free environment and were used at 8-12 weeks of age. All experiments were performed in co-housed mice in accordance with both NIH and Institutional Animal Care and Use Committee guidelines.

Immunization and Sample Collection.

Figure 2A:
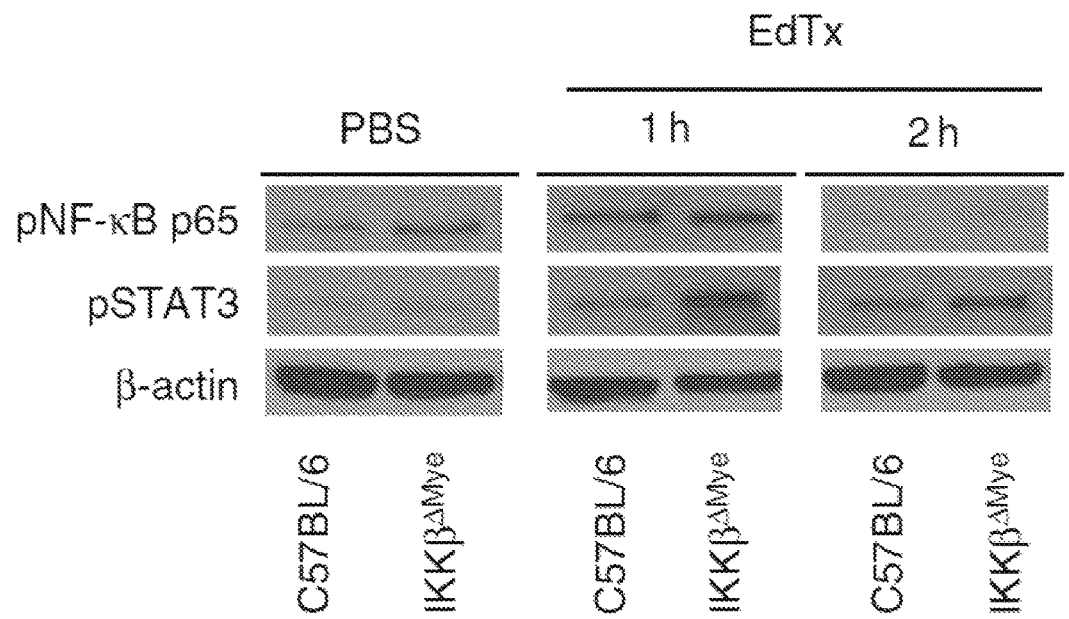
FIGS. 2A to 2C show expression of phospho-NF-kB, phospho-STAT3, and profile of myeloid cell subsets in sublingual tissues after application of edema toxin (EdTx) to wilde-type mice or genetically modified mice lacking IKKβ signaling in myeloid cells. Sublingual tissues were collected at different time points after sublingual administration of phosphate-buffered saline (PBS) or EdTx (15 µg).
Figure 9A:
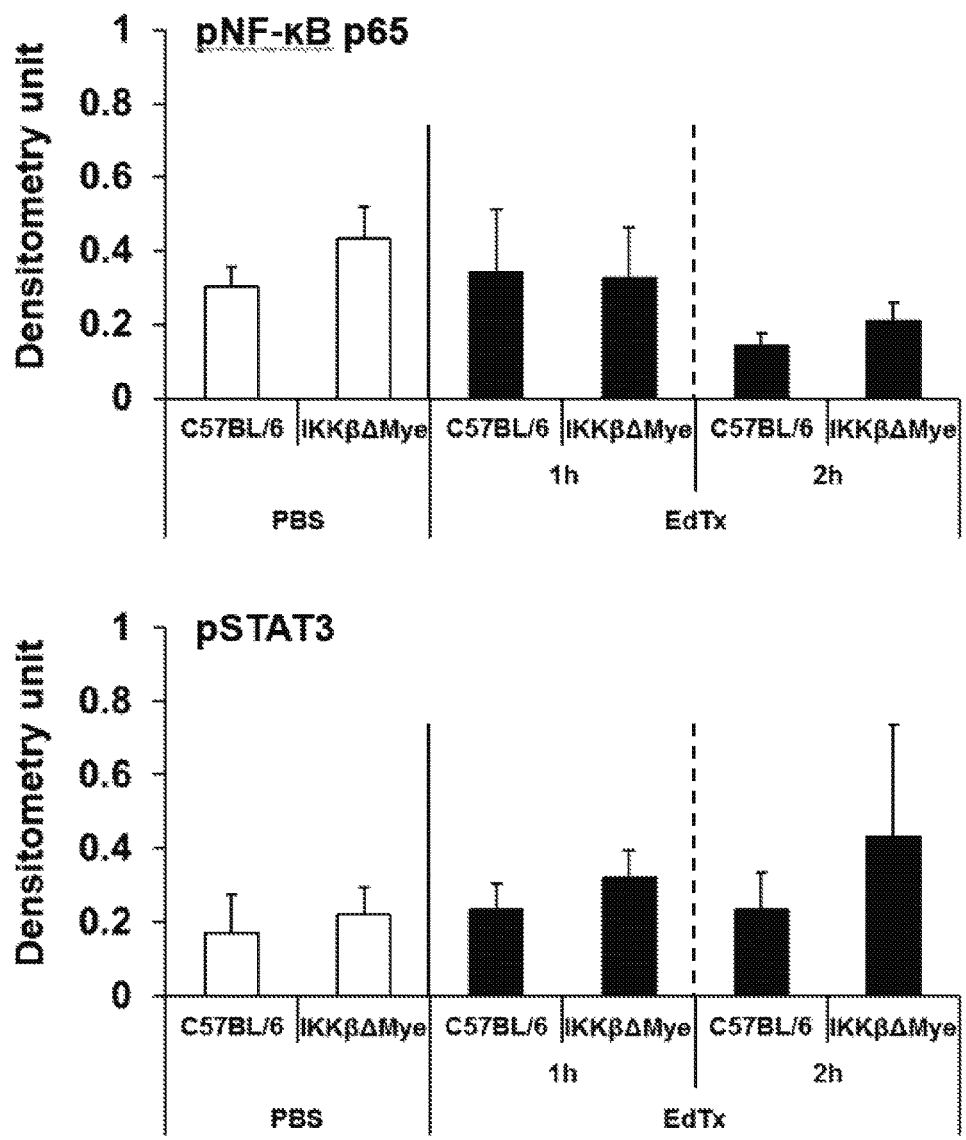
FIGS. 9A and 9B show expression of phospho-NF-κB and phospho-STAT3 in sublingual tissues after application of EdTx. Sublingual tissues of C57BL/6 or IKKβ$^{\Delta M ye}$ mice were collected at different time points after sublingual administration of PBS or EdTx (15 µg). Expression of pSTAT3 and phosphoNF-κB p65 was analyzed by western blotting.
Figure 9B:
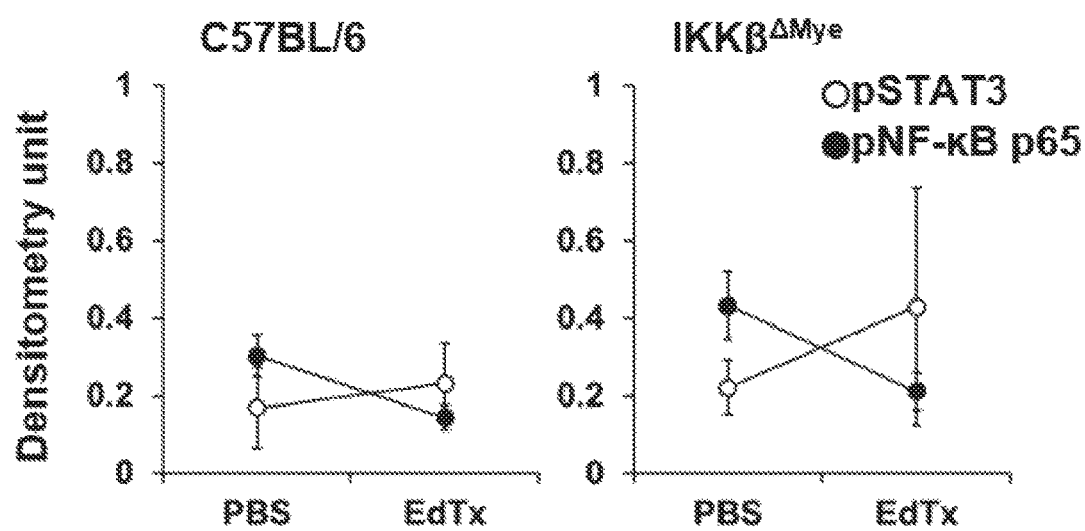

Sublingual immunization was performed on mice anesthetized by intraperitoneal injection of ketamine and xylazine hydrochloride. The F1-V antigen and *Bacillus anthracis* protective antigen (PA) and edema factor (EF) were obtained from BEI Resources (Manassas, Va.). Mice were immunized three times, i.e., Day 0, 7, and 14 by administration of 30 μl of PBS containing 50 μg of F1-V antigen alone, or 50 μg of F1-V antigen plus 15 μg EdTx, i.e., 15 μg PA and 15 μg EF. To prevent accidental spill-over into the digestive tract, 15 μl of antigen plus adjuvant was administered twice at 6 hour intervals. Blood and external secretions (fecal extracts, vaginal washes, and saliva) were collected as previously described (Boyaka P N, et al. (2003) J Immunol 170(1):454-462). To identify the anatomic sites targeted by the adjuvant EdTx, mice were euthanized at 3, 6 or 12 hours after sublingual application of 15 μg EdTx. Sublingual tissues and CLNs were then collected and analyzed. To address the contribution of neutrophil to Ab isotype responses, mice were administered i.p. with 0.5 mg of the neutrophil Ly6G-specific 1A8 monoclonal Ab (BioXCell) 2 days before the sublingual immunization.

Immunoblot Analysis of Transcription Factors.

The expression of pNF-κB, pSTAT3, and β-actin was analyzed by immunoblot as previously described (Bonnegarde-Bernard A, et al. (2014) Mucosal Immunol 7(2): 257-267) using anti-pNF-κB and pSTAT3 antibodies (Cell Signaling, Danvers, Mass.).

ELISA and ELISPOT Assays for Antigen-Specific Ab Responses and Total Ig Isotype Levels.

Antigen-specific Ab levels in plasma and external secretions were assessed as described previously on microtiter plates coated with 5 μg/ml of F1-V or PA (Duverger A, et al. (2010) J Immunol 185(10):5943-5952; Duverger A, et al. (2006) J Immunol 176(3):1776-1783). For analysis of B cell epitope responses, microtiter plates were coated with 50 μg/ml of overlapping peptides spamming the entire F1 molecule (BEI Resources). The frequency of antibody secreting cells (ASCs) was determined by ELISPOT assay with anti-IgM, IgG and IgA Abs (SBA, Birmingham, Ala.) (Boyaka P N, et al. (2003) J Immunol 170(1):454-462).

Macrophage Toxicity Assay to Assess Anti-PA Neutralizing Abs.

The protective effects of PA-specific Abs were determined by analyzing survival of RAW 264.7 macrophages exposed to *Bacillus anthracis* lethal toxin in vitro as described previously (Duverger A, et al. (2010) J Immunol 185(10): 5943-5952; Duverger A, et al. (2006) J Immunol 176(3): 1776-1783).

In Vitro Cultures and Flow Cytometry Analysis.

To address the role of IKKβ in myeloid cells, myeloid cell-depleted $CD11b^-$ splenocytes were co-cultured with autologous or heterologous $CD11b^+$ cells at 7:1 ratios, i.e., $1.4\times10^5$ to $0.2\times10^5$ cells in the presence or absence of 5 μg/ml LPS (Sigma-Aldrich, St. Louis, Mo.) and 2 μg/ml EdTx. The $CD11b^-$ and $CD11b^+$ splenocytes were purified using CD11b MicroBeads with an autoMACS (Miltenyi Biotec, Auburn, Calif.).

For studies that addressed the direct effect of neutrophils on immunoglobulin production by B cells, $CD19^+$ splenocytes from C57BL/6 mice were incubated overnight with 100 ng/ml of LPS, washed extensively and then co-cultured with autologous neutrophils from C57BL/6 mice or heterologous neutrophils from $IKK\beta^{\Delta Mye}$ mice without additional stimuli. The mRNA responses were analyzed 24 hours later, and culture supernatants were collected on day 5 for analysis of immunoglobulin isotypes (IgM, IgG, and IgA). For analysis of T helper cytokine responses, single-cell suspensions of spleen cells were incubated with 5 μg/ml F1-V at 37° C. for 5 days (Duverger A, et al. (2010) J Immunol 185(10):5943-5952; Duverger A, et al. (2006) J Immunol 176(3):1776-1783). Flow cytometry analysis was performed after extracellular and intracellular staining using the following fluorophore-conjugated monoclonal antibodies: B220, CD11b (Miltenyi Biotec, Auburn, Calif.), CD3e, CD4, CD8, IFN-γ, IL-4, IL-17A, $I\text{-}A^b$ (MHC II), Gr-1, IgE, CCR2 and CXCR2 (BD Biosciences, San Jose, Calif.), F4/80 (AbD Serotec, Raleigh, N.C.), IL-17RA (eBiosciences, San Diego, Calif.), IgM, IgG and IgA (SBA, Birmingham, Ala.), LTB4R2 (Santa Cruz Biotechnology, Inc., Dallas, Tex.). Labeled cells were analyzed with an Accuri C6 flow cytometer (BD Biosciences, San Jose, Calif.)

Quantitative real-time RT-PCR. Extraction of total RNA, cDNA generation and RT-PCR were performed as previously described (Duverger A, et al. (2010) J Immunol 185(10):5943-5952). RT-PCR for the expression of IgA heavy chain transcripts was determined using the following forward and reverse primers set: 5'-AGC TGG TAA AGC CTG GGG CCT-3' (SEQ ID NO:6) and 5'-CGG TGA CTG AGG TTC CTT GAC CC-3' (SEQ ID NO:7) with cDNA as template. The level of mRNA expression in each target gene was calculated with the formula: 20−(mean of $Ct_{target\ gene}$− mean of $Ct_{\beta\text{-}actin}$).

Statistical analysis. Factorial ANOVA, followed by analysis of interaction effect and Duncan's multiple range test were used to compare values across categorical groups. Tests were considered significant at a probability of $p\leq0.05$. Statistical analyses were performed with the Statistica 10.0 software package (StatSoft, Tulsa, Okla.).

Results

Toxin Adjuvants Differentially Recruit Myeloid-Lineage Cells into Sublingual Tissues Both CT (Boyaka, P. N., et al. J. Immunol. 170, 454-462 (2003)) and EdTx (Duverger, A., et al. J. Immunol. 185, 5943-5952 (2010); Duverger, A., et al. J. Immunol. 176, 1776-1783 (2006)) are mucosal adjuvants that promote mucosal SIgA responses via the nasal route. CT can also promote IgA responses when used as an adjuvant for vaccines given by the epicutaneous route or topically on the sublingual mucosa (Song, J. H., et al. J. Immunol. 182, 6851-6860 (2009); Cuburu, N., et al. Vaccine 25, 8598-8610 (2007)). In contrast, EdTx was not effective at inducing IgA when used as an epicutaneous (Duverger et al., unpublished observation) or sublingual adjuvant. To elucidate the mechanism underlying the inability of EdTx to induce IgA by the sublingual route, innate cell subsets present in sublingual tissues after sublingual application of EdTx were first analyzed. The number of $CD11b^+$ myeloid cells increased in the sublingual tissues of mice 3 h after application of EdTx, but not CT (FIG. 1A). Flow cytometric (Geissmann, F., et al. Immunity 19, 71-82 (2003)) and morphologic analysis of the myeloid cell subsets (FIGS. 8B to 8D) in sublingual tissues 3 h after application of EdTx showed a high frequency (32%) of $CD11b^+F4/80^-Gr\text{-}1^{high}$ cells (neutrophils) and a lower frequency (12%) of $CD11b^+F4/80^+Gr\text{-}1^-$ cells (non-inflammatory monocytes). The frequencies of $CD11b^+F4/80^+Gr\text{-}1^{low}$ cells (macrophages or DCs) and $CD11b^+F4/80^+Gr\text{-}1^{high}$ cells (inflammatory monocytes) were not affected by EdTx. In contrast with EdTx, CT increased the frequency (34 vs. 26%) of macrophages/dendritic cell (FIGS. 1C,1D).

EdTx does not Recruit Neutrophils into Sublingual Tissues of Mice Lacking IKKβ in Myeloid Cells The adjuvant activities of CT and EdTx involve proinflammatory responses and acquisition of antigen-presenting cell functions by myeloid cells (Duverger, A., et al. J. Immunol. 185, 5943-5952 (2010); Duverger, A., et al. J. Immunol. 176, 1776-1783 (2006); Bromander, A. K., et al. Scand. J. Immunol. 37, 452-458 (1993); McGee, D. W., et al. J. Immunol. 151, 970-978 (1993)). The transcription factor NF-κB is a master regulator of cytokine responses and migration of innate cells (Grivennikov, S. I., et al. Cytokine Growth Factor Rev. 21, 11-19 (2010)). Activation of NF-κB in mouse epithelial cells lacking IKKβ and with impaired ability for nuclear translocation of phospoNF-κB p65, resulted in increased pSTAT3 responses in gut tissues (Bonnegarde-Bernard, A., et al. Mucosal Immunol. 7, 257-267 (2014)). Thus, how EdTx affects the expression of STAT3 in sublingual tissues of control and IKKβ$^{\Delta M y e}$ mice, which lack IKKβ in myeloid cells, was examined. As depicted in FIGS. 2A and 9, pSTAT3 levels were low in tissues of mice that received saline and increased after application of EdTx. In contrast, pNF-κB levels were higher in tissues of phosphate-buffered saline—than in EdTx-treated mice. Although the transcription factors appeared to be regulated in the opposite direction after EdTx-treatment, the difference in their levels of expression failed to reach statistical significance during the time frame analyzed (FIGS. 2A and 9).

Figure 2B:
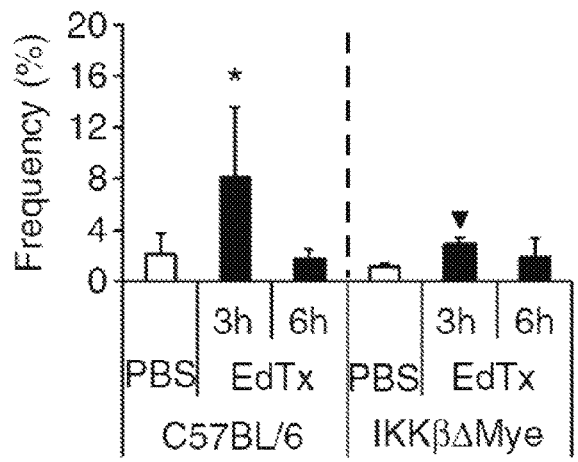
Figure 2C:
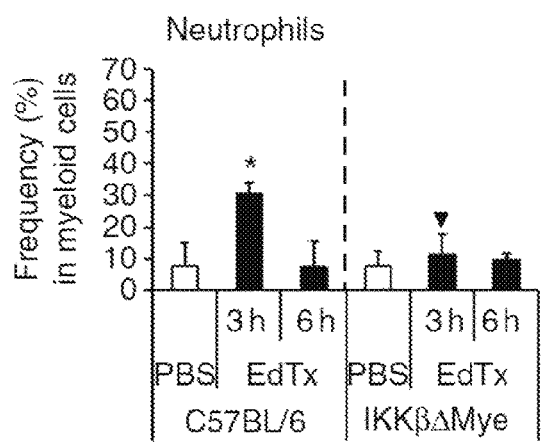
Figure 2C:
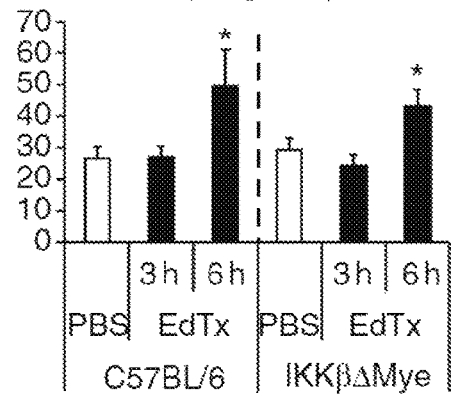
Figure 2C:
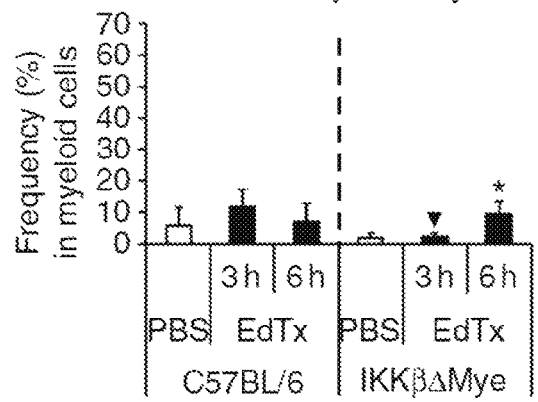
Figure 2C:
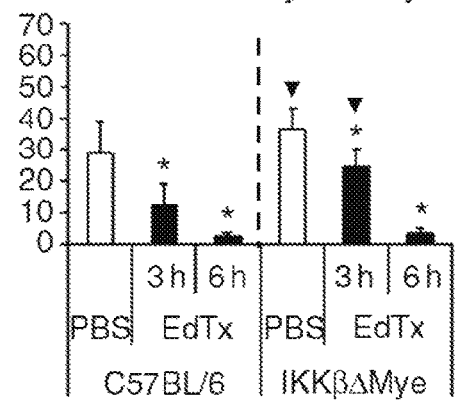
Figure 10:
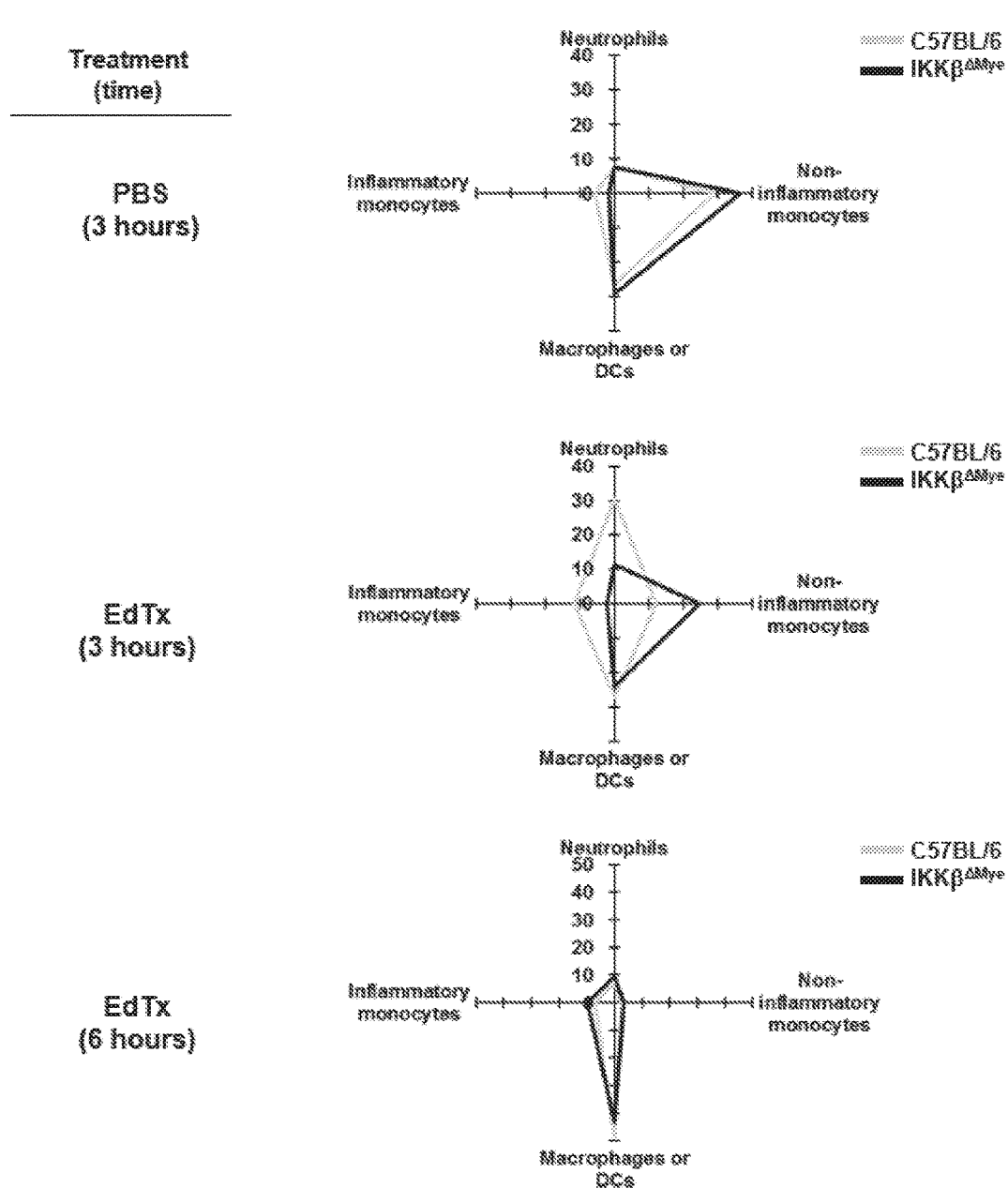
FIG. 10 shows profile of myeloid cell subsets in sublingual tissues. Sublingual tissues of C57BL/6 and IKKβ$^{\Delta M ye}$ mice were collected at 3 and 6 hours after sublingual administration of PBS or EdTx (15 µg). Flow cytometry analysis of myeloid cell subsets determined by expression of CD11b, F4/80 and Gr-1. Results are expressed as mean percentage of three independent experiments and represented as radar plots to facilitate visual comparison between groups.

Myeloid cells in sublingual tissues were also analyzed at 3 and 6 h after application of EdTx (FIGS. 2B, 2C, and 10). Unlike control C57BL/6 mice, the IKKβ$^{\Delta M y e}$ mice did not exhibit an important increase in the frequency of CD11b♭ cells in the sublingual tissues 3 h after application of EdTx (FIG. 2B). Control C57BL/6 and IKKβ$^{\Delta M y e}$ mice exhibited a similar proportion of myeloid cell subsets before application of EdTx, except for non-inflammatory monocytes, which were higher in IKKβ$^{\Delta M y e}$ than in control C57BL/6 mice (FIGS. 2C and 10). Three hours after application of EdTx, sublingual tissues of IKKβ$^{\Delta M y e}$ mice showed significantly lower frequencies of neutrophils when compared with C57BL/6 (FIGS. 2C and 10).

Figure 3A:
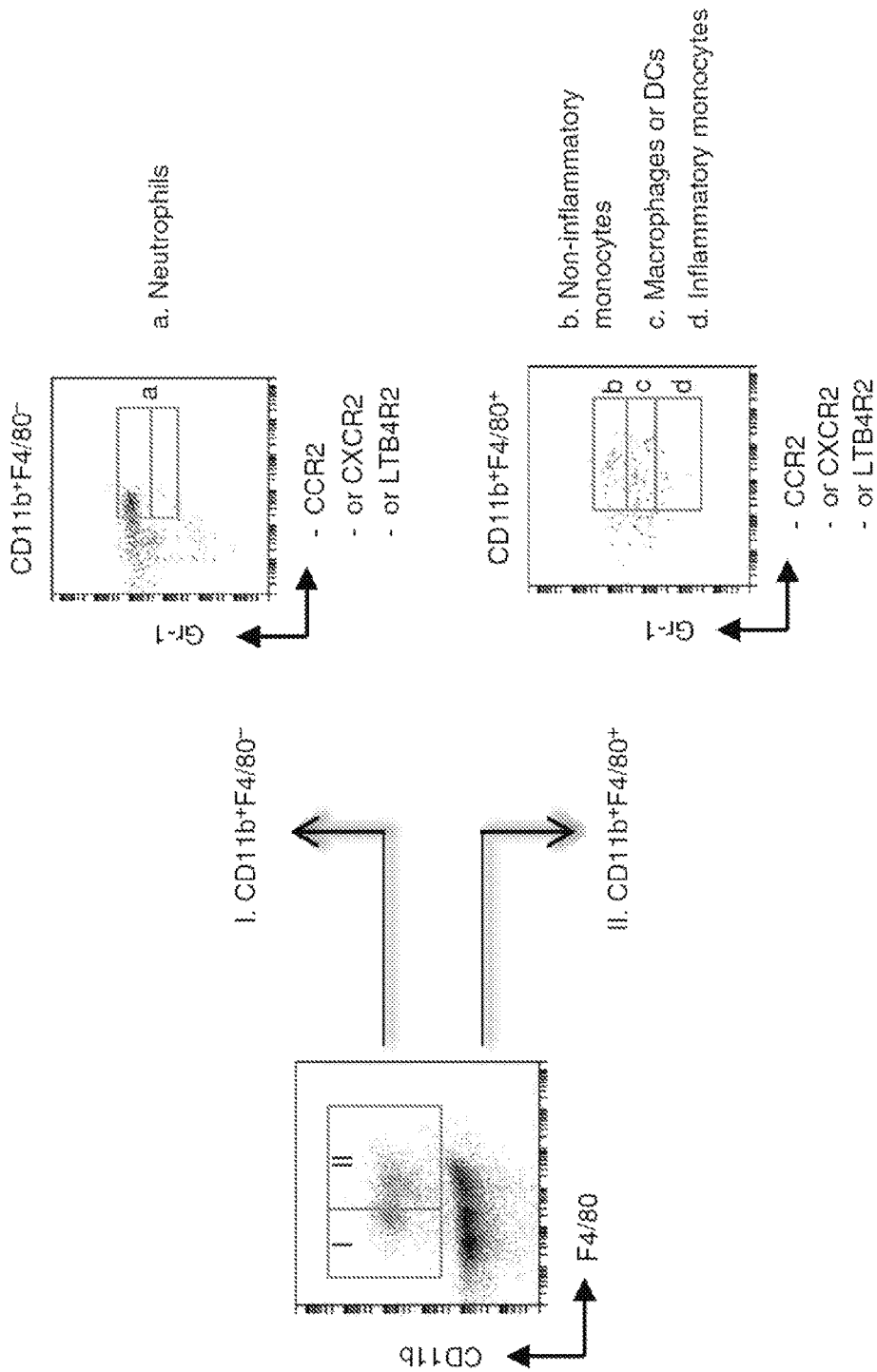
FIGS. 3A to 3C show expression of chemokine and leukotriene B4 receptors by myeloid cell subsets in sublingual tissues. Sublingual tissues were collected 3 h after sublingual application of phosphate-buffered saline (PBS) or edema toxin (EdTx) (15 µg). Expression of CCR2, CXCR2, and LTB4R2 by myeloid cell subsets was analyzed by flow cytometry.
Figures 3B, 3C:
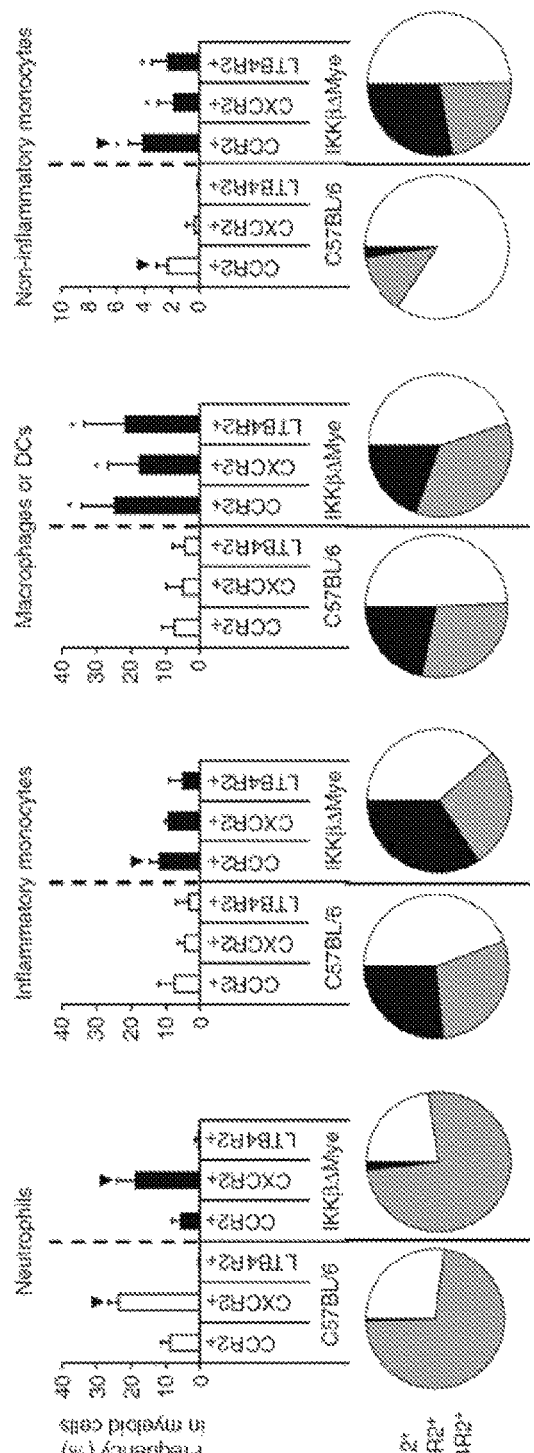
Figure 11A:
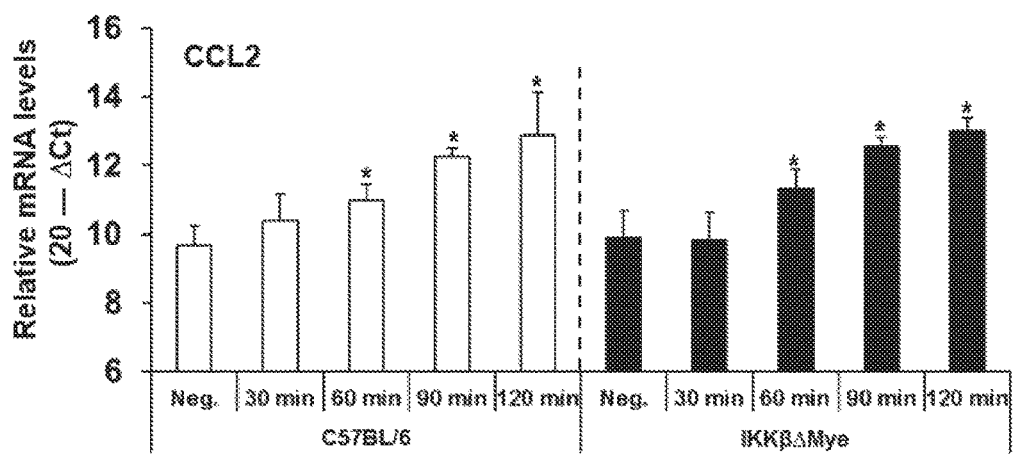
FIGS. 11A and 11B show kinetics of CCL2 (monocyte chemoattractant)-specific (FIG. 11A) and CXCL2 (neutrophils chemoattractant)-specific (FIG. 11B) mRNA responses in sublingual tissues of C57BL/6 or IKKβ$^{ΔMye}$ mice exposed to EdTx in vitro. Single-cell suspensions of sublingual tissues from naïve mice were incubated with EdTx (2 μg/ml). At indicated time points, mRNA responses for CCL2 and CXCL2 were analyzed by real-time RT-PCR. Data represent mean±SD (n=3). *p≤0.05 compared to cultures without EdTx.
Figure 11B:
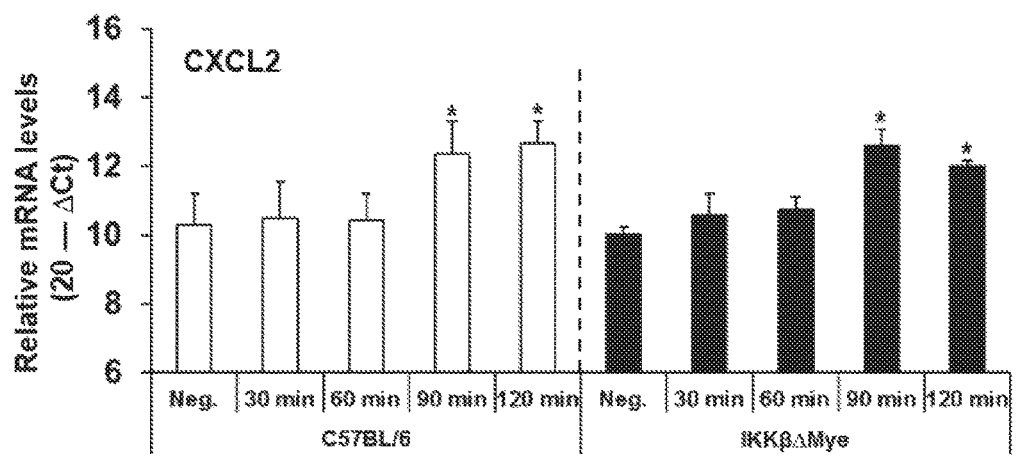

EdTx was reported to differentially affect the recruitment and cytokine secretion by some immune cells (Klezovich-Benard, M., et al. PLoS Pathog. 8, e1002481 (2012)). Therefore, the expression of CCL2 and CXCL2, two chemokines known to recruit inflammatory monocytes and neutrophils, respectively, was also examined. Sublingual tissue cells of control C57BL/6 and IKKβ$^{\Delta M y e}$ mice had similar basal levels of CCL2 and CXCL2 messenger RNA (mRNA), and exhibited similar kinetics and magnitude of responses after exposure to EdTx (FIG. 11). The expression of CCR2 and CXCR2, the receptors of CCL2 and CXCL2 by myeloid cell subsets, was also examined in sublingual tissues 3 h after application of EdTx in vivo (FIG. 3). Since leukotriene B4 could mediate chemotaxis of macrophages and granulocytes (Grespan, R., et al. Arthritis Rheum. 58, 2030-2040 (2008); Chou, R. C., et al. Immunity 33, 266-278 (2010)), the expression of the leukotriene B4 receptor (LTB4R2) was also investigated. Neutrophils in sublingual tissues of C57BL/6 and IKKβ$^{\Delta M y e}$ mice exhibited similar profiles of receptor expression (FIG. 3B, 3C). On the other hand, macrophages/DCs and non-inflammatory monocytes collected in sublingual tissues of IKKβ$^{\Delta M y e}$ mice exhibited higher frequencies of CCR2$^+$, CXCR2$^+$, and LTB4R2$^+$ cells. Alone, these results cannot explain the higher number of neutrophils in the sublingual tissues of C57BL/6. The pie diagram (FIG. 3C), which summarizes the relative contribution of each receptor in myeloid cell subsets shows a broader profile of receptor expression in macrophages/DCs and non-inflammatory monocytes of IKKβ$^{\Delta M y e}$ mice. Thus, these cells may have a competitive advantage for responding to chemoattractant signals via ligand binding to these receptors.

Figure 4A:
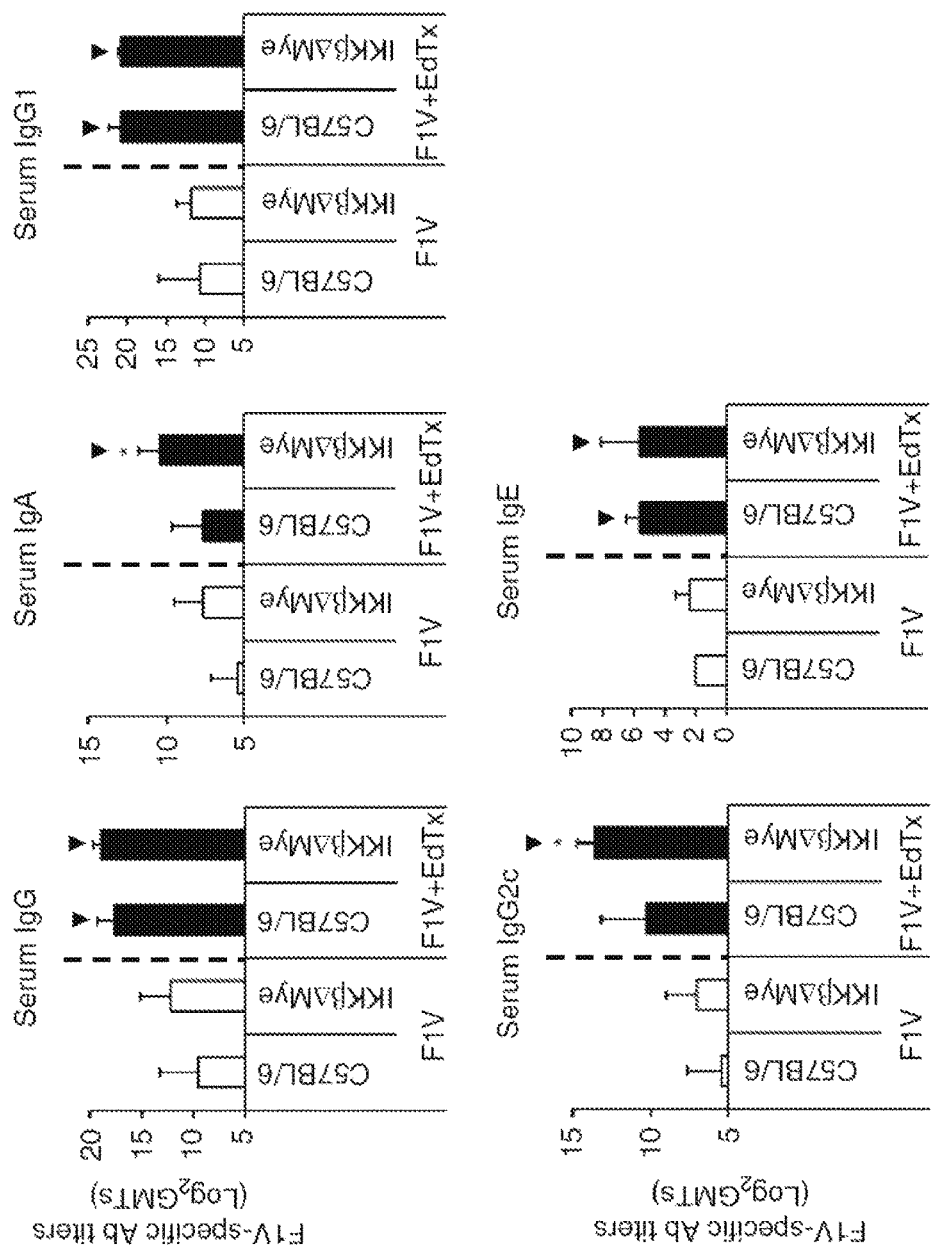
Figure 4B:
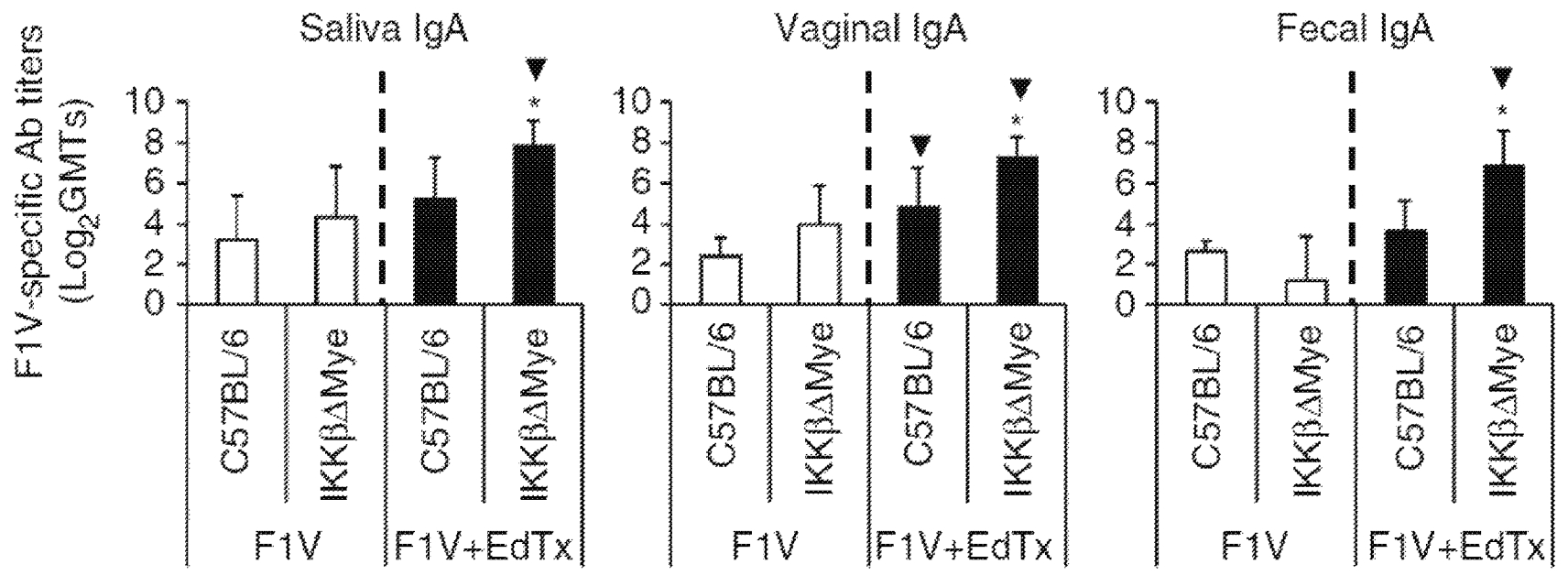
Figure 4C:
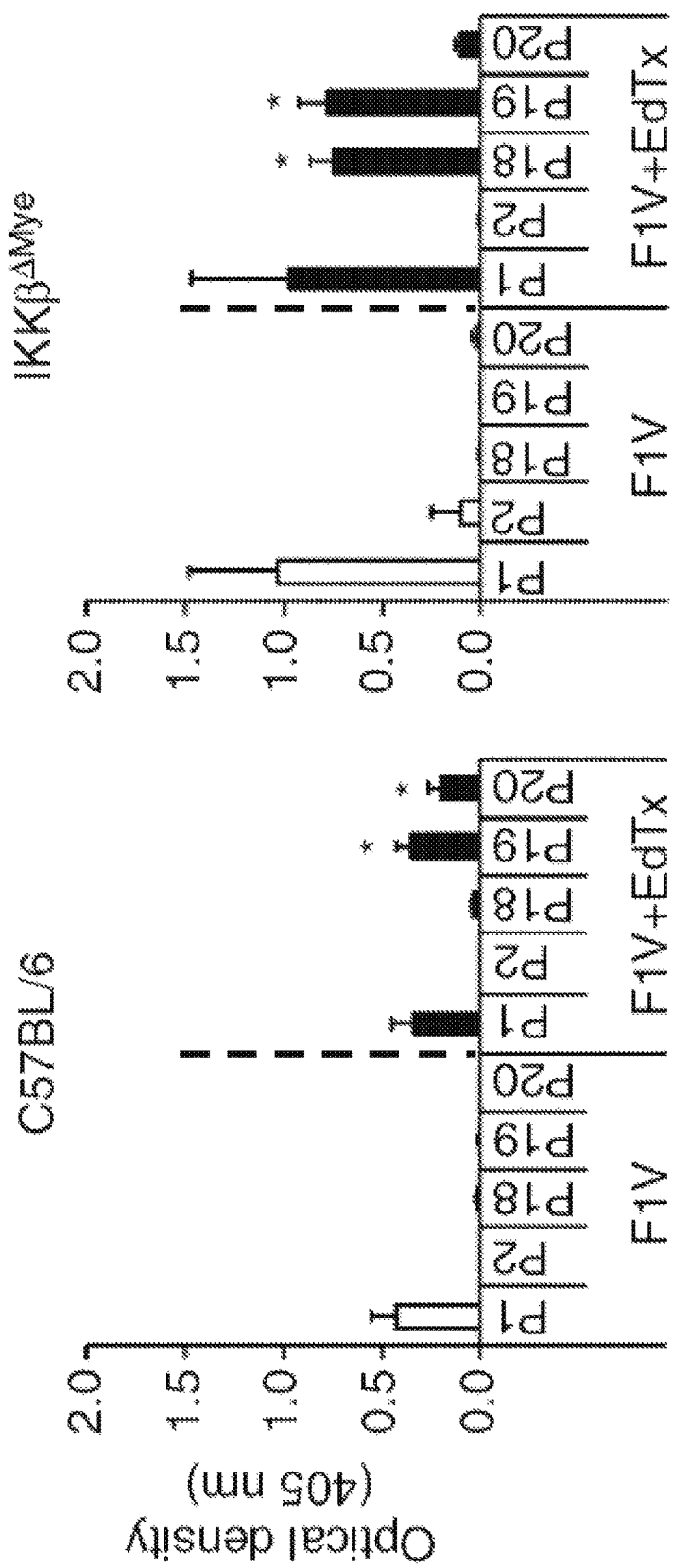

IKKβ Deficiency in Myeloid Cells Enhances the Adjuvant Activity of EdTx for Sublingual Immunization and Promotes Ag-Specific SIgA Responses Experiments were conducted to determine whether the broader expression of chemokine receptors and LTB4R2s by macrophage/dendritic cell and non-inflammatory monocytes in sublingual tissues of IKKβ$^{\Delta M y e}$ mice after application of EdTx could affect the profile of immune responses induced by this adjuvant. For this purpose, mice were immunized via the sublingual route with recombinant Yersinia pestis F1-V antigen and B. anthracis EdTx as adjuvant. Sublingual co-application of EdTx enhanced antigen (F1-V)-specific serum IgG responses (IgG and IgG1) and no difference was seen between control C57BL/6 and IKKβ$^{\Delta M y e}$ mice (FIG. 4A). The similar levels of IgE responses were seen in control C57BL/6 and IKKβ$^{\Delta M y e}$ mice, suggesting that Th2-dependent Abs were not affected in IKKβ$^{\Delta M y e}$ mice. On the other hand, IKKβ$^{\Delta M y e}$ mice exhibited enhanced IgG2c responses (FIG. 4A). Interestingly, unlike control C57BL/6 mice, IKKβ$^{\Delta M y e}$ mice developed antigen-specific serum IgA responses, (FIG. 4A). The increase in serum IgA responses in IKKβ$^{\Delta M y e}$ mice was associated with antigen-specific SIgA in the saliva, vaginal washes, and fecal extracts (FIG. 4B). Experiments were also conducted to determine whether the specificity and function of antibody (Ab) induced by EdTx as sublingual adjuvant were affected by the absence of IKKβ-dependent signaling in myeloid cells. After sublingual immunization with F1-V alone, control C57BL/6 and IKKβ$^{\Delta M y e}$ mice developed IgG Abs, which were directed against the same peptide (i.e., P1-17 or P1) of the F1-capsular antigen (FIG. 4C and Table 1). EdTx as an adjuvant promoted Abs that reacted to two additional epitope peptides in control C57BL/6 and IKKβ$^{\Delta M y e}$ mice. However, only one of the additional peptides (P19) was shared by Abs from control C57BL/6 and IKKβ$^{\Delta M y e}$ mice (FIG. 4C and Table 1).

TABLE 1

Linear epitopes of Yersinia pestis F1-capsular antigen recognized by antibodies after sublingual immunization

| Peptide | Residues | Sequence | |
|---------|----------|----------|---|
| P1 | 1-17 | 5'-MKKISSVIAIALFGTIA-3' | SEQ ID NO: 1 |
| P2 | 7-23 | 5'-VIAIALFGTIATANAAD-3' | SEQ ID NO: 2 |
| P18 | 103-119 | 5'-HQFTTKVIGKDSRDFDI-3' | SEQ ID NO: 3 |

TABLE 1-continued

Linear epitopes of *Yersinia pestis* F1-capsular antigen
recognized by antibodies after sublingual immunization

| Peptide | Residues | Sequence | | |
|---------|----------|----------|---|---|
| P19 | 109-125 | 5'-VIGKDSRDFDISPKVNG-3' | SEQ ID NO: | 4 |
| P20 | 115-131 | 5'-RDFDISPKVNGENLVGD-3' | SEQ ID NO: | 5 |

Abbreviation ELISA, enzyme-linked immunosorbent assay.
Mice were immunized three times at weekly intervals by sublingual application of F1-V alone or F1-V plus EdTx as an adjuvant. Serum samples were collected 1 week (Day 21) after the last immunization, and the B-cell epitope responses were evaluated by ELISA using overlapping peptides spamming the all F1 molecule (BEI Resources, Manassas, VA). Shown are the sequences and corresponding residues of peptides that reacted with sera of mice immunized with F1-V alone or F1-V plus EdTx as an adjuvant.

Figure 12A:
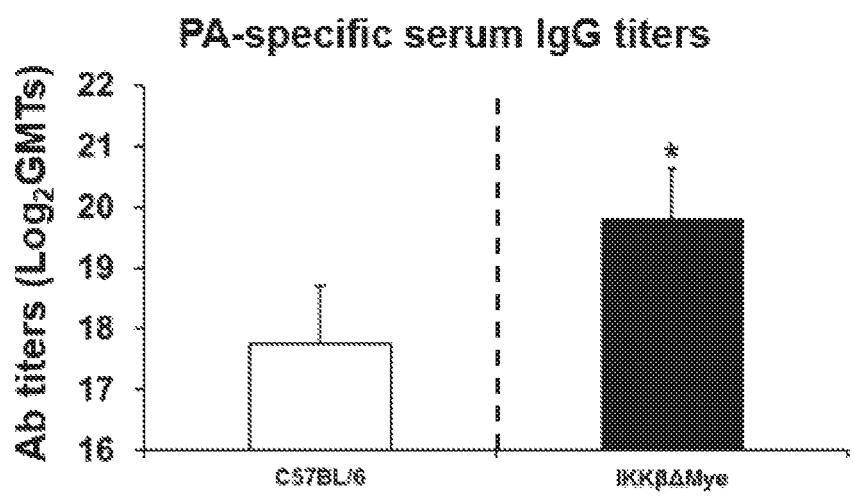
FIGS. 12A and 12B show lack of IKKβ signaling in myeloid cells enhances PA-specific responses after sublingual immunization with EdTx. Control C57BL/6 and IKKβ$^{ΔMye}$ mice were immunized three times at weekly intervals by sublingual application of F1-V alone or F1-V plus EdTx as adjuvant. Serum samples were collected 1 week (Day 21) after the last immunization.
Figure 12B:
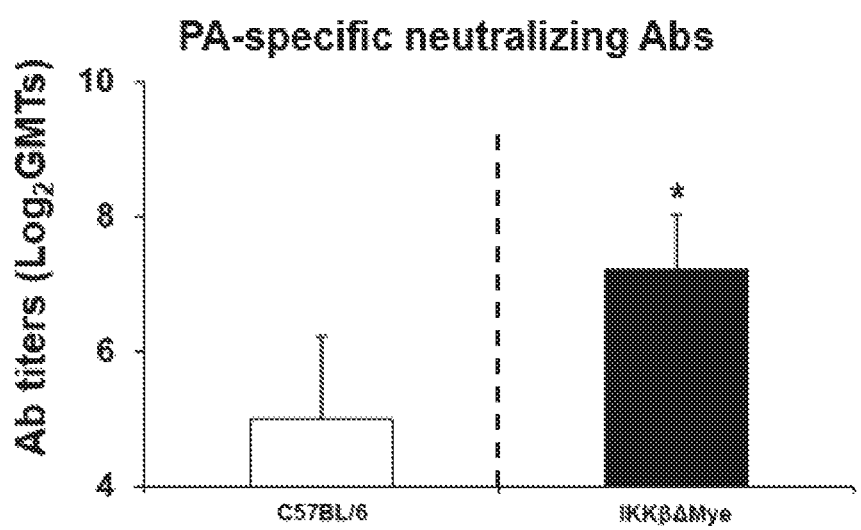
Figure 13A:
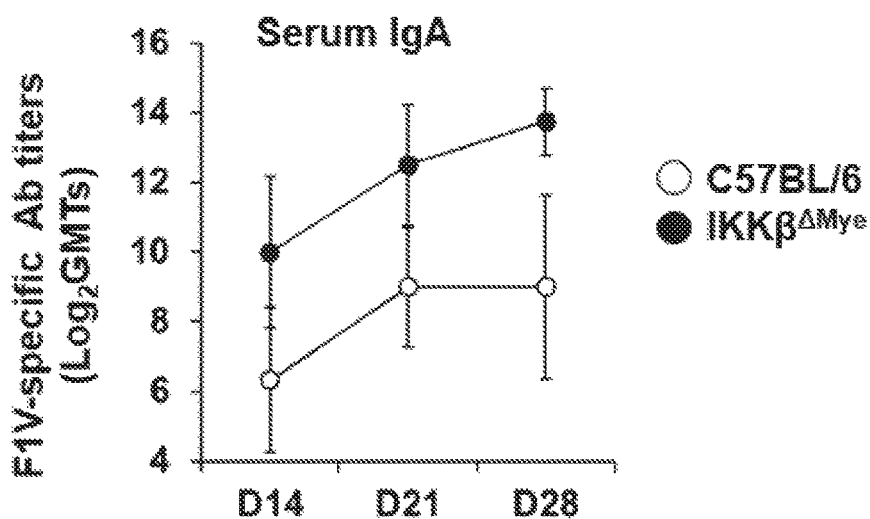
FIGS. 13A and 13B show Ag-specific serum (FIG. 13A) and fecal IgA (FIG. 13B) responses of IKKβ$^{ΔMye}$ mice to sublingual vaccination. Control C57BL/6 and IKKβ$^{ΔMye}$ mice were immunized three times at weekly intervals by sublingual application of F1-V alone plus cholera toxin (5 μg) as adjuvant. Serum and fecal extract samples were collected weekly, and antigen-specific IgA responses were measured by ELISA. The end-point titers are expressed as $Log_2$ GMTs.±SD from C57BL/6 (n=5), and IKKβ$^{ΔMye}$ mice (n=5). *p≤0.05 compared with C57BL/6. No response was detected in naïve mice.
Figure 13B:
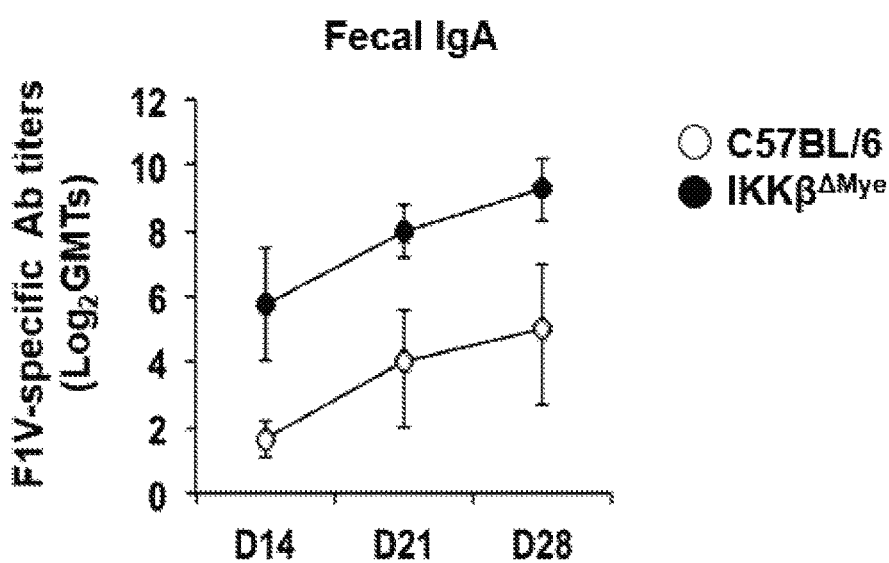

Experiments were also conducted to determine whether the enhanced IgA responses seen in IKKβ$^{\Delta Mye}$ mice were restricted to F1-V as antigen and EdTx as adjuvant. Nasal immunization with EdTx is known to promote immunity against the EdTx binding subunit PA (Duverger, A., et al. J. Immunol. 185, 5943-5952 (2010); Duverger, A., et al. J. Immunol. 176, 1776-1783 (2006)). Sublingual immunization with EdTx also enhanced PA-specific serum IgG Ab titers in IKK$^{\Delta Mye}$ mice (FIG. 12A) and this was consistent with the enhanced levels of PA-specific neutralizing Abs (FIG. 12B). In addition, serum and mucosal IgA responses induced by CT as a sublingual adjuvant were enhanced in IKKβ$^{Mye}$ mice (FIG. 13).

Figure 5:
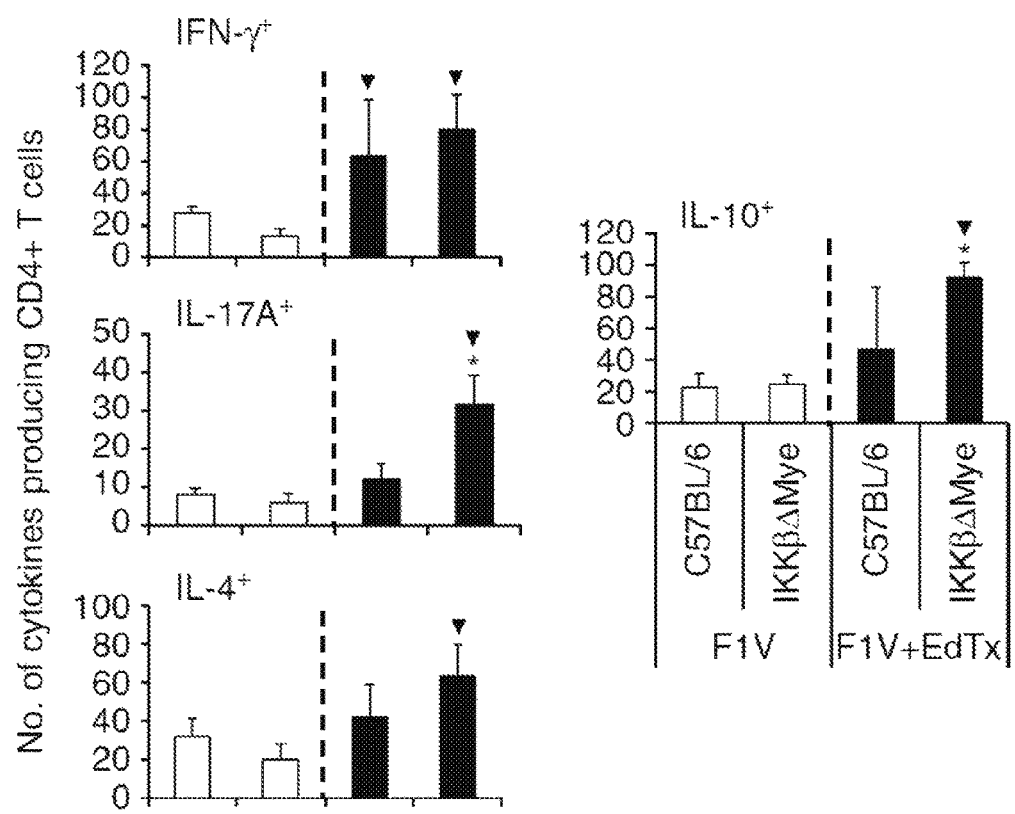
FIG. 5 shows lack of IKKβ in myeloid cells broadens antigen-specific T-helper cytokine responses to sublingual immunization with edema toxin as an adjuvant. Spleen cells were collected three weeks after the last immunization and cultured for 5 days in the presence of recombinant F1-V (5 µg ml$^{-1}$). The numbers of CD4$^+$ T cells expressing Th1, Th2, and Th17 cytokines were analyzed by flow cytometry. Data are expressed as mean±s.d. from C57BL/6 (n=4) and IKKβ$^{\Delta M ye}$ mice (n=4). *p≤0.05 compared with C57BL/6, and ▼p≤0.05 compared with mice immunized with F1-V alone.

Finally, antigen (F1-V)-specific Th cytokine responses supported by EdTx as an adjuvant for sublingual vaccination was analyzed. In wild-type C57BL/6 mice, the sublingual adjuvant EdTx enhanced the frequency of antigen-specific IFN-γ producing Th cells in the spleen (FIG. 5). On the other hand, the IKKβ$^{\Delta Mye}$ mice exhibited a broader profile of Th-cell responses with a significant increase of antigen-specific IFN-γ (Th1), IL-4 (Th2), IL-10$^+$, and IL-17$^+$ producing Th cells (FIG. 5).

Figure 6A:
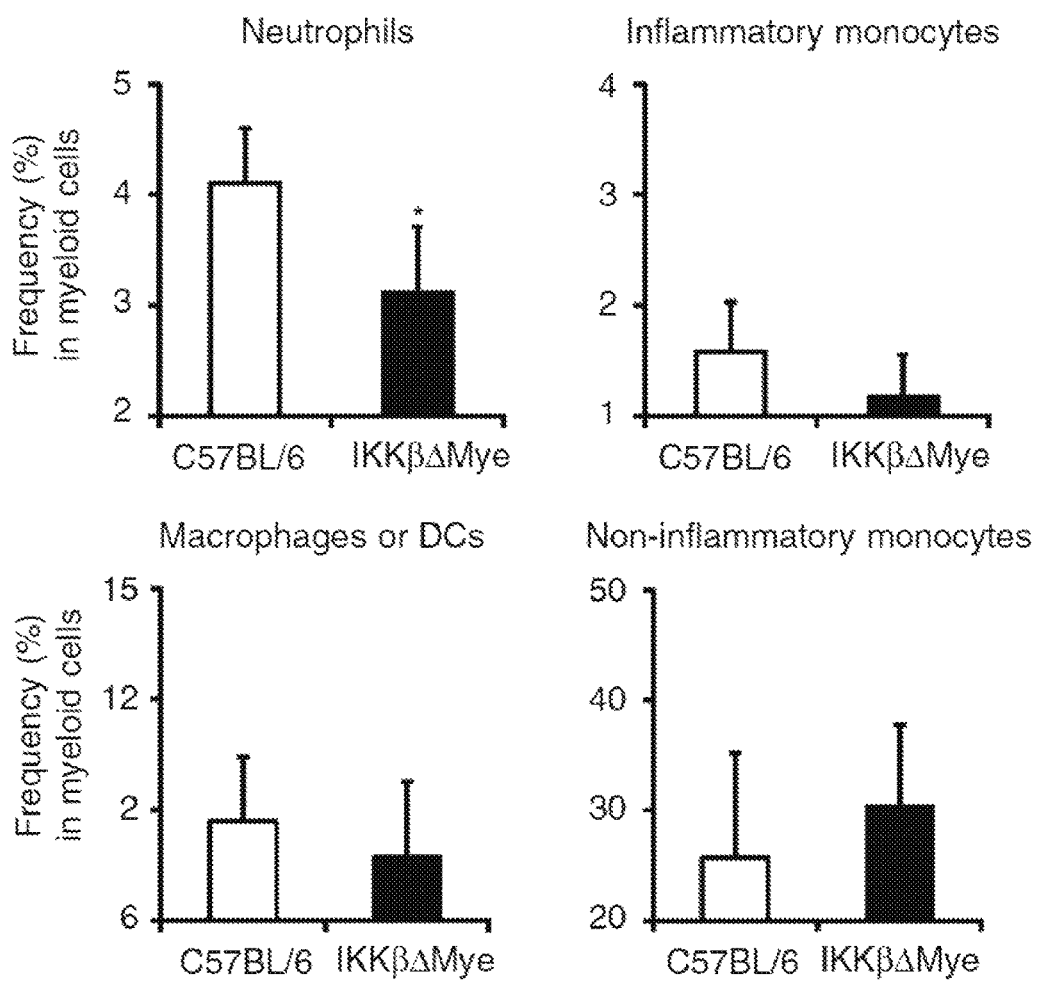
FIGS. 6A to 6D show inverse correlation between the number of neutrophils and immunoglobulin-A (IgA) responses to sublingual immunization. Cervical lymph nodes were collected at 6 h after sublingual administration of edema toxin (EdTx) (15 µg).
Figure 6B:
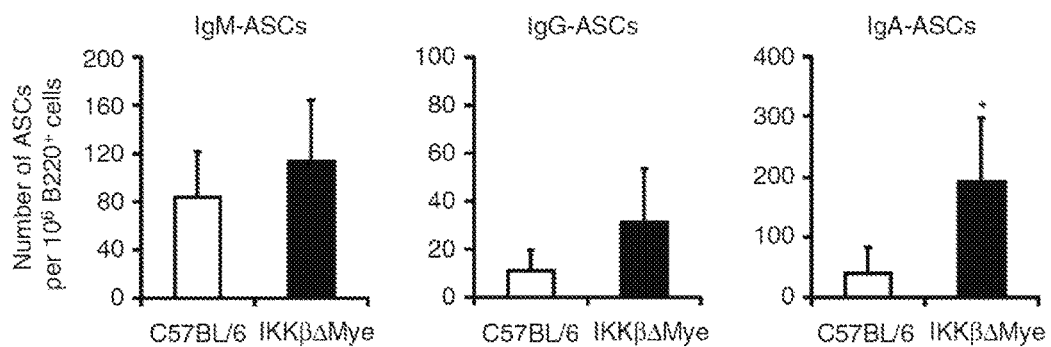
Figure 6C:
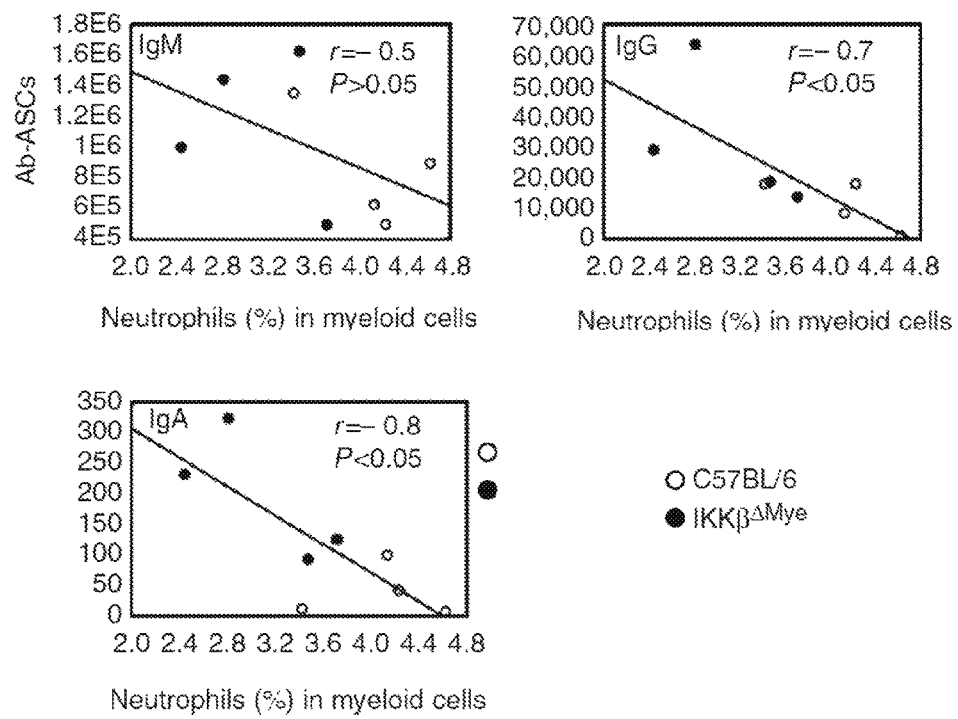

The Frequency of Neutrophils Inversely Correlates with Production of IgA in CLNs CLNs are considered inductive sites for adaptive immune responses after sublingual and nasal immunization. 6 h after application of EdTx, the frequency of CD11b$^+$ cells returned toward basal levels in sublingual tissues (FIG. 2B). Cells may have migrated to CLN and thus myeloid cell subsets in these lymphoid tissues were analyzed. The frequency of neutrophils was significantly reduced in CLNs of IKKβ$^{\Delta Mye}$ compared to control C57BL/6 mice, while the other myeloid cell subsets remained unchanged (FIG. 6A). CLN cells from EdTx-treated mice were then cultured in the presence of lipopolysaccharide. Three days later, a significantly higher number of IgA-secreting cells in IKKβ$^{\Delta Mye}$ than in control C57BL/6 mice (FIG. 6B). Of interest, the number of IgA-secreting cells in the CLNs of both control C57BL/6 and IKKβ$^{\Delta Mye}$ mice were inversely correlated (r=−0.8) with the numbers of neutrophils in these tissues (FIG. 6C).

Figure 6D:
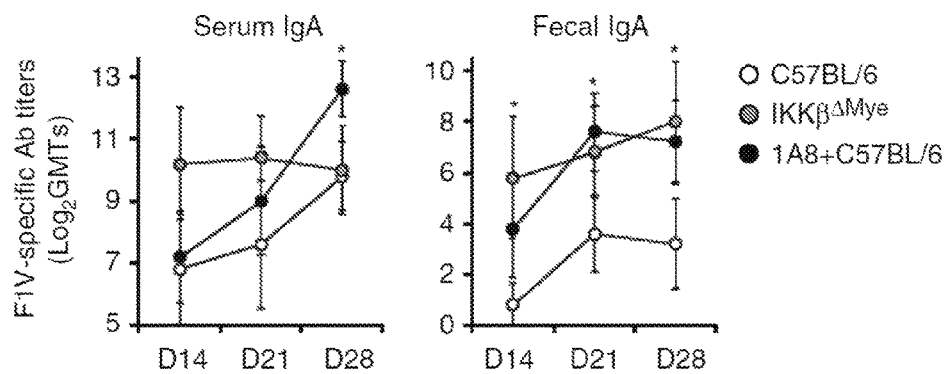
Figure 14A:
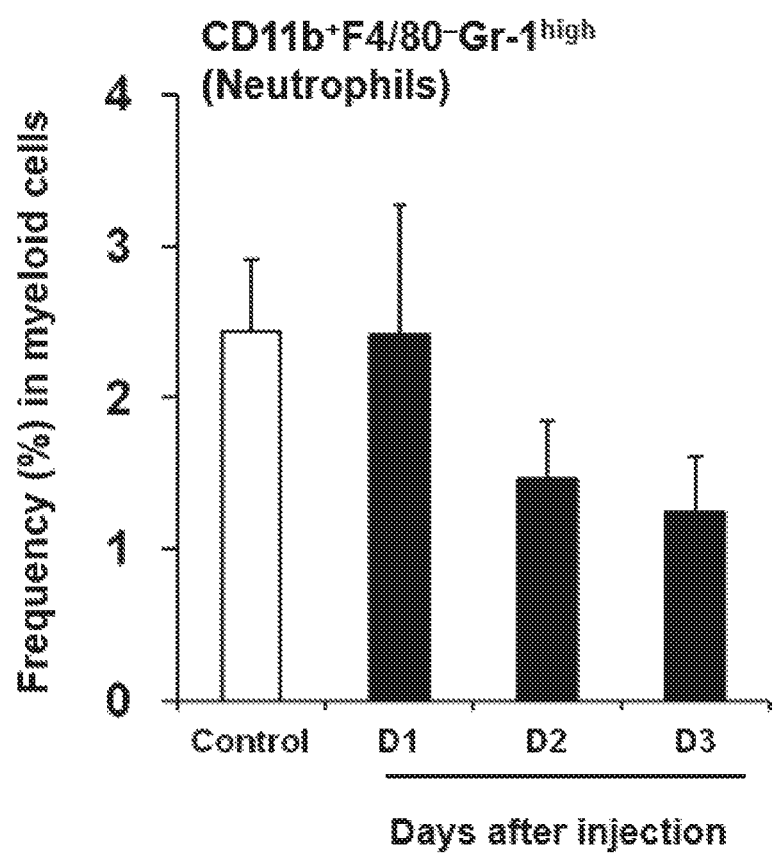
FIGS. 14A and 14B show frequencies of myeloid cells in sublingual tissues and cervical lymph nodes after treatment with 1A8 mAb. Wild-type C57BL/6 mice were treated by ip administration of the neutrophil Ly6G-specific 1A8 monoclonal Ab or PBS (control).
Figure 14B:
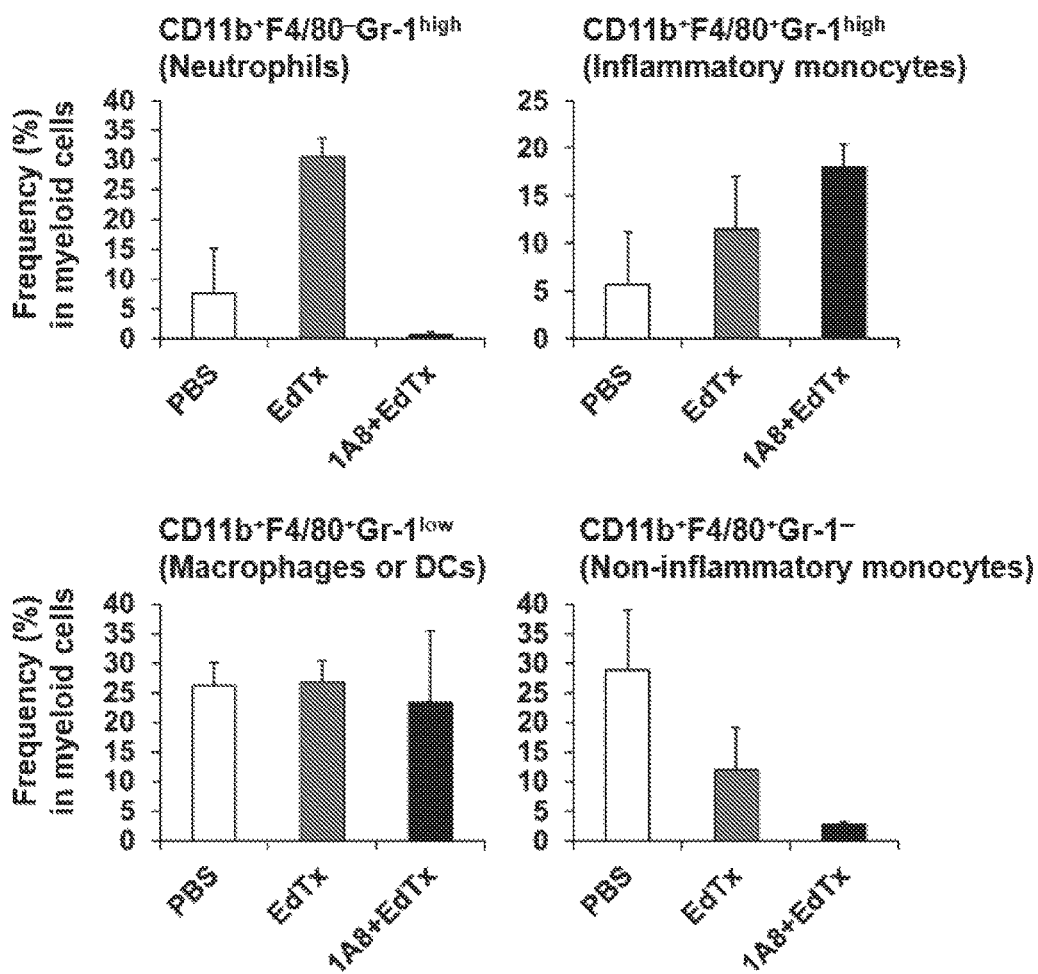

Reduction of Neutrophils Augments the Adjuvant Effect of EdTx on Ag-Specific IgA Responses To further establish that an inverse correlation exists between the frequency of neutrophils in sublingual tissues and CLNs, and antigen-specific IgA responses, wild-type C57BL/6 were injected (IP) with a neutrophil Ly6G-specific 1A8 monoclonal Ab 2 days before sublingual immunization with F1-V and EdTx as an adjuvant. This treatment reduced the frequency of neutrophils in CLNs of wild-type C57BL/6 mice (FIG. 14A), and C57BL/6 mice pre-treated with 1A8 (1A8+C57BL/6) contained virtually no neutrophils in sublingual tissues after application of EdTx (FIG. 14B). These 1A8+C57BL/6 mice also gradually developed F1-V-specific serum IgA titers over the time points tested and reached higher serum IgA titers than non-treated C57BL/6 or IKKβ$^{\Delta Mye}$ mice at Day 28 (FIG. 6D). Interestingly, depletion of neutrophils also enhanced mucosal IgA Ab responses; 1A8+C57BL/6 mice produced high levels of F1-V-specific fecal IgA Abs, which were comparable to those measured in IKK$^U$Me mice (FIG. 6D).

Neutrophils Suppress Production of IgA by B Cells

Figure 7A:
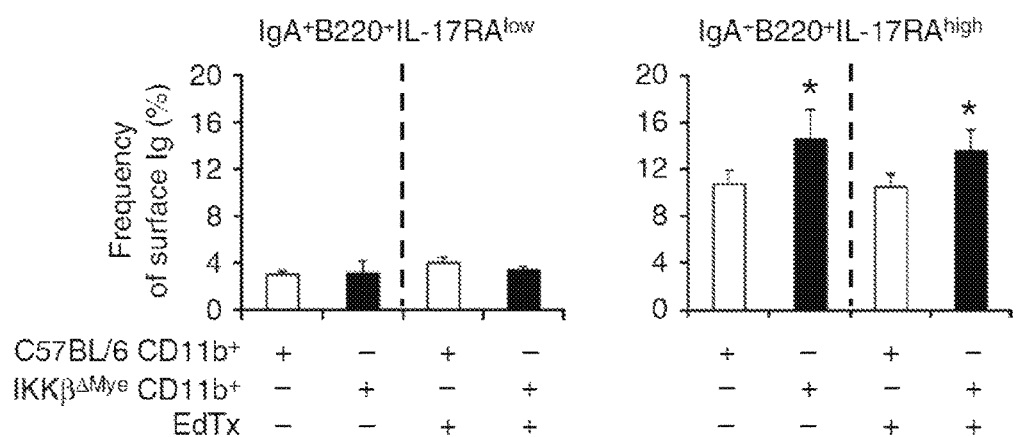
FIGS. 7A to 7D show neutrophils suppress the production of immunoglobulin A (IgA) by B cells.
Figure 15A:
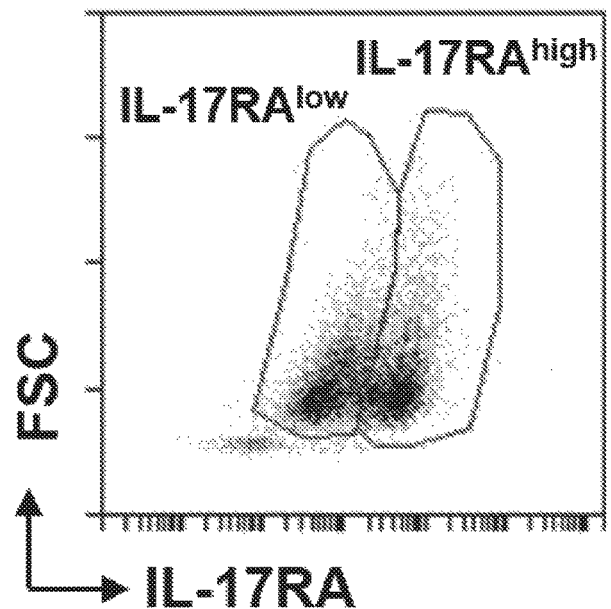
FIGS. 15A to 15C show CD11b$^+$IKKβ$^{ΔMye}$ cells increase expression of surface IgA on B220$^+$IL-17RA$^{high}$ cells. CD11b$^-$ spleen cells from C57BL/6 mice were co-cultured with autologous CD11b$^+$ cells from C57BL/6 or heterologous CD11b$^+$IKKβ$^{ΔMye}$ cells in the presence of LPS (5 μg/ml) with or without EdTx (2 μg/ml) for 5-day co-culture.
Figure 15B:
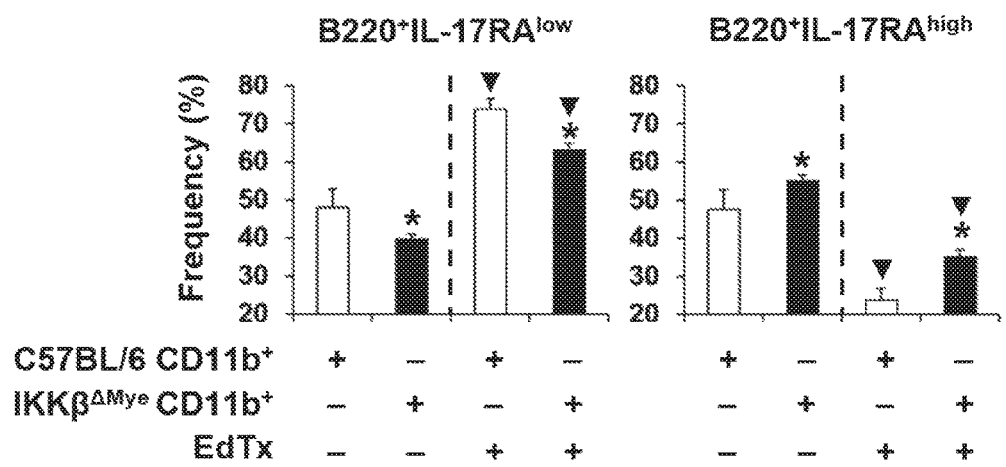
Figure 15C:
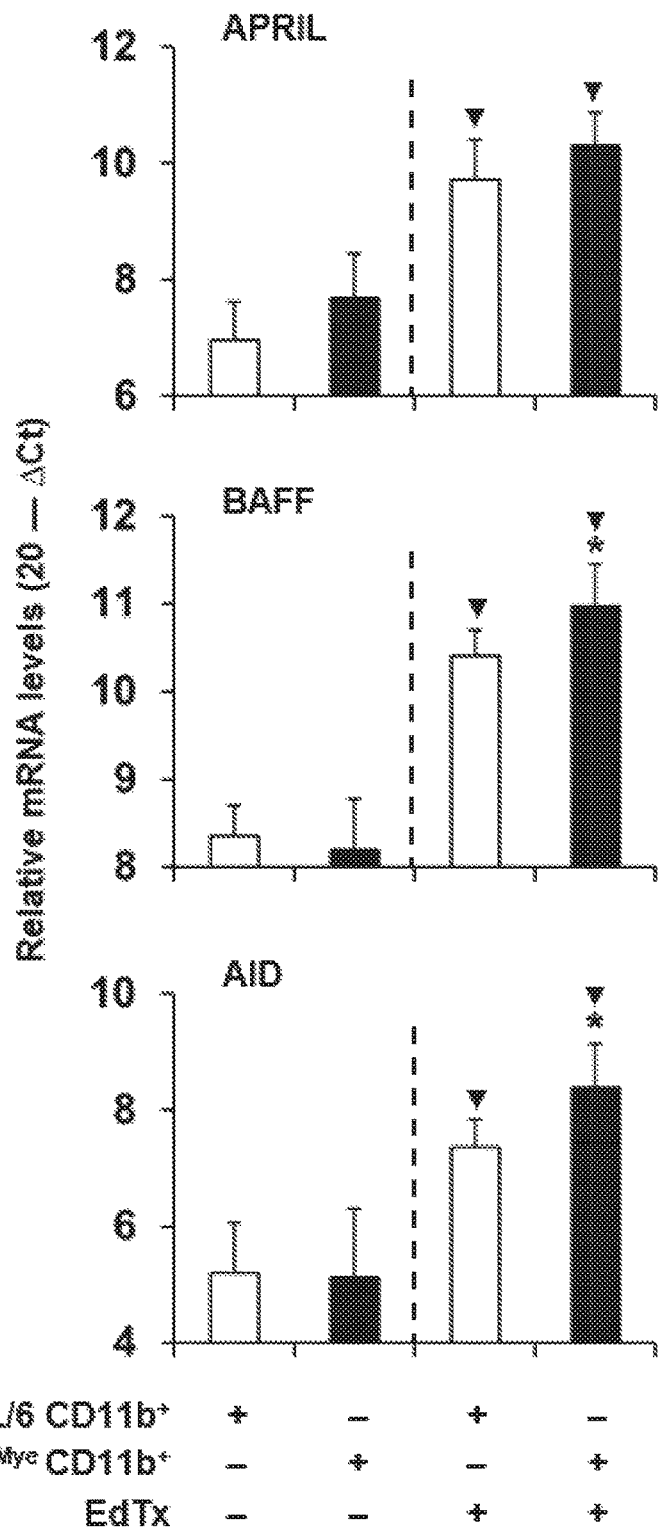
Figure 16A:
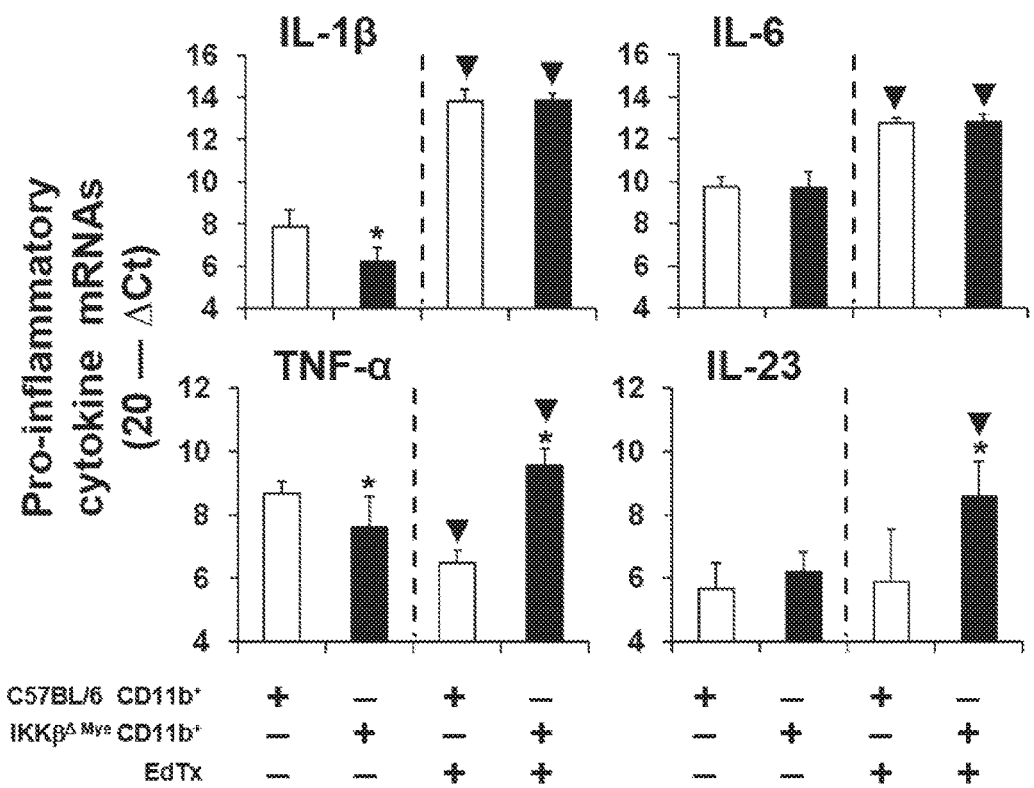
FIGS. 16A to 16C show IKKβ$^{ΔMye}$ CD11b$^+$ cells and edema toxin regulate mRNA expression of cytokines and enzymes implicated in immunoglobulin class switch and Ab production. Spleen cells from C57BL/6 mice were depleted of CD11b cells (CD11b$^-$ spleen) and cultured for 24 hours at 37° C. with either autologous CD11b$^+$ cells from C57BL/6 or heterologous CD11b$^+$ cells from IKKβ$^{ΔMye}$ mice (IKKβ$^{ΔMye}$ CD11b$^+$ cells) in the presence or absence of EdTx (2 μg/ml). The mRNA levels of pro-inflammatory cytokines (FIG. 16A), anti-inflammatory cytokines (FIG. 16B) and Caspase 1 (FIG. 16C) were determined by real time RT-PCR. Data are expressed as mean±SD and are representative of three independent experiments. *p≤0.05 compared with C57BL/6 CD11b$^+$ cells, and ▼p≤0.05 compared with co-culture in the absence of EdTx.
Figure 16B:
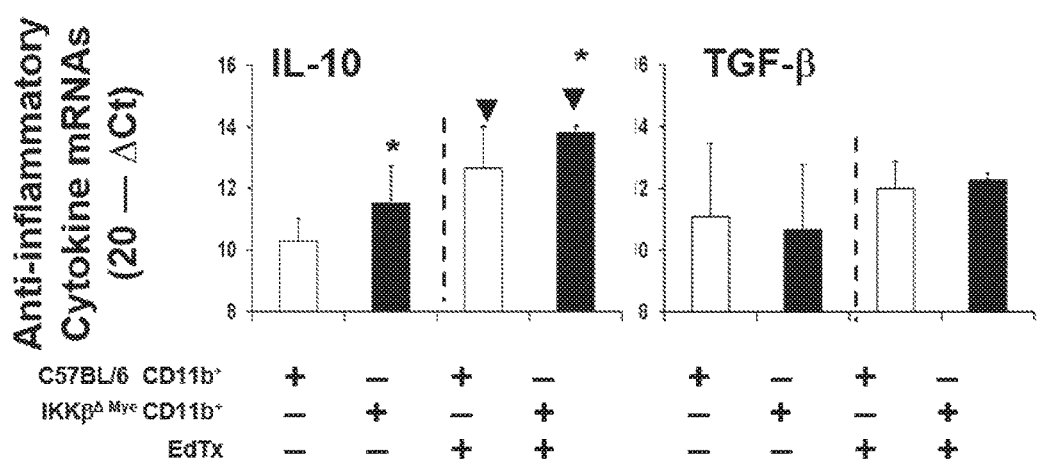
Figure 16C:
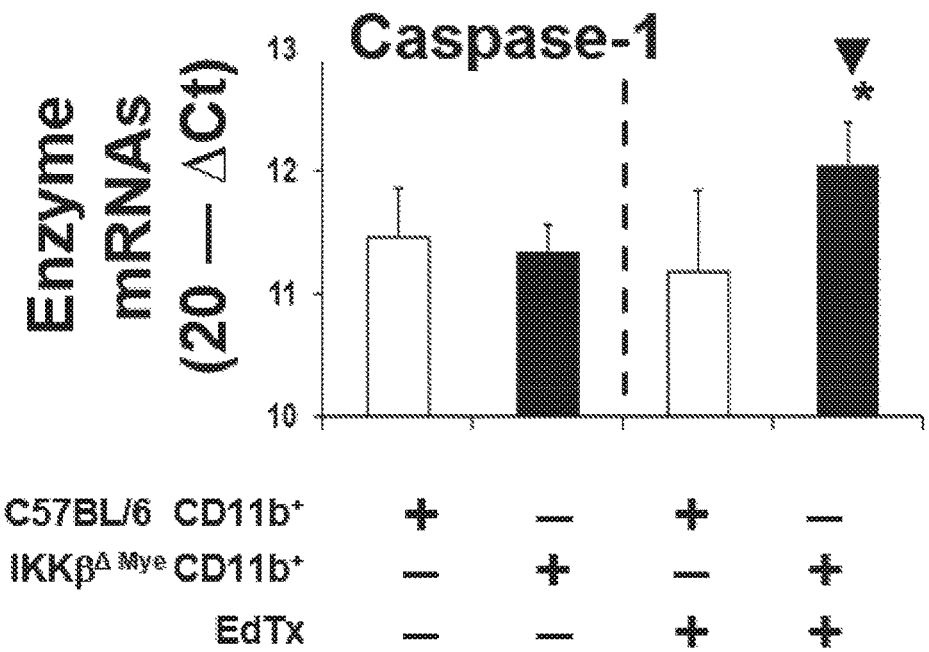

Results clearly show that the ability to generate IgA responses is enhanced in the absence of IKKβ in myeloid cells or when the number of neutrophils is reduced. In addition, the ability of EdTx to induce systemic and mucosal IgA responses in IKKβ$^{\Delta Mye}$ mice is associated with increased Th17 responses and production of IL-17A (FIG. 5). Thus, experiments were conducted to determine how alteration of canonical NF-κB-mediated signaling via IKKB-deletion in myeloid cells (IKKβ$^{\Delta Mye}$) could support Ig class switch and Ab production by B cells. For this purpose, CD11b-depleted spleen cells from C57BL/6 mice were co-cultured with 20% autologous CD11b$^+$ cells (C57BL/6 CD11b$^+$) or CD11b$^+$ cells from IKK$^{\Delta Mye}$ mice (IKKβ$^{\Delta Mye}$ CD11b$^+$) with or without EdTx in the presence of lipopoly-saccharide (Lycke, N., et al. J. Immunol. 142, 3781-3787 (1989)). After 5 days of culture, cells were segregated into IL-17RA$^{low}$ and IL-17RA$^{high}$ cells (FIG. 15A). Co-culture with IKKβ$^{\Delta Mye}$ CD11b$^+$ cells significantly increased the frequency of B220$^+$ IL-17RA$^{high}$ B cells (FIG. 15B). As shown in FIG. 7A, these cultures contained low frequencies of surface IgA cells among IL-17RA$^{low}$ B cells regardless of the presence of IKKβ$^{\Delta Mye}$ CD11b$^+$ cells. Interestingly, high frequencies of IL-17RA$^{high}$ B cells expressed surface IgA and co-culture with IKKβ$^{\Delta Mye}$ CD11b$^+$ cells further increased these frequencies. To further elucidate signals that supported IgA responses, mRNA levels of the B-cell activators a proliferation-inducing ligand (APRIL) and B-cell activation factor of the TNF family (BAFF), and activation-induced deaminase (AID) were analyzed. Addition of EdTx to cultures of spleen cells enhanced mRNA levels of APRIL, BAFF, and AID, and the presence of IKKβ$^{\Delta Mye}$ CD11b♭ further enhanced BAFF- and AID-specific mRNA expression (FIG. 15C). The presence of IKK$^{\Delta Mye}$ CD11b$^+$ did not affect EdTx-induced IL-1β and IL-6 mRNA levels, but increased EdTx-induced TNF-α, IL-23, IL-10, and Caspase-1 mRNA levels (FIG. 16). Taken together, these results show that myeloid cells lacking IKKβ provide a microenvironment favorable for Ig class switch and B-cell production of IgA.

Figure 7B:
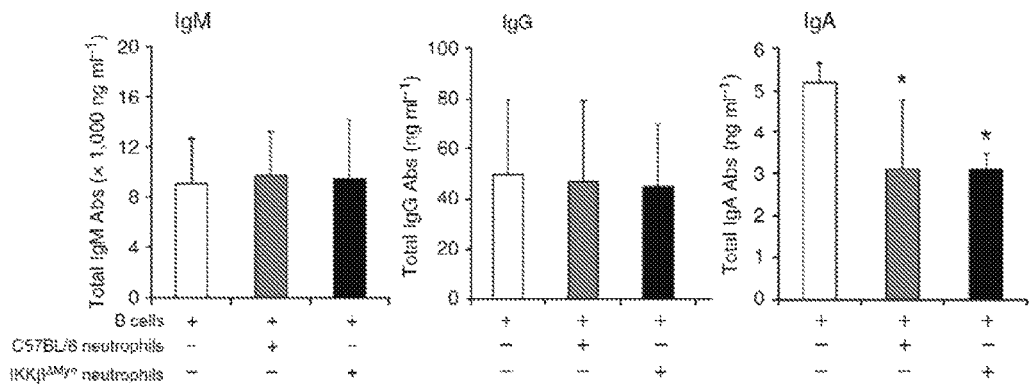
Figure 7C:
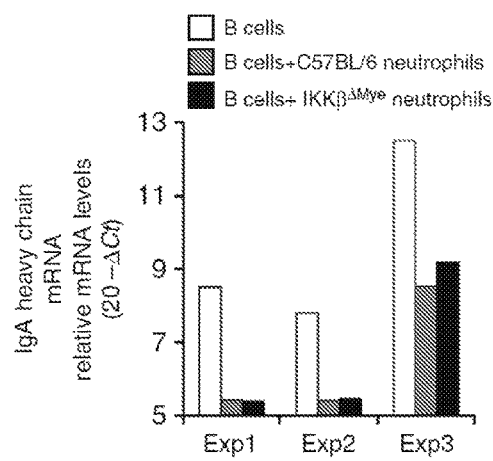
Figure 7D:
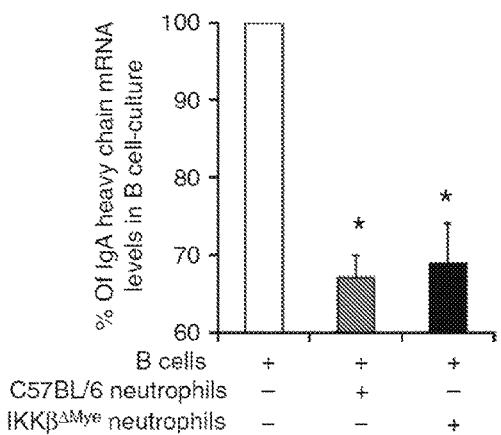
Figure 8A:
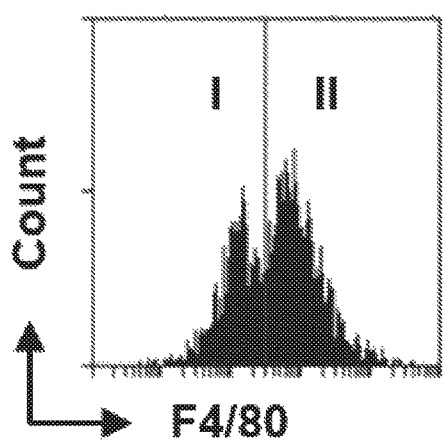
FIGS. 8A to 8C show analysis of myeloid cell subsets recruited to sublingual tissues after sublingual application of EdTx. Sublingual tissues of C57BL/6 and IKKβ$^{\Delta M ye}$ mice were collected 3 hours after sublingual administration of PBS or EdTx (15 µg).
Figure 8B:
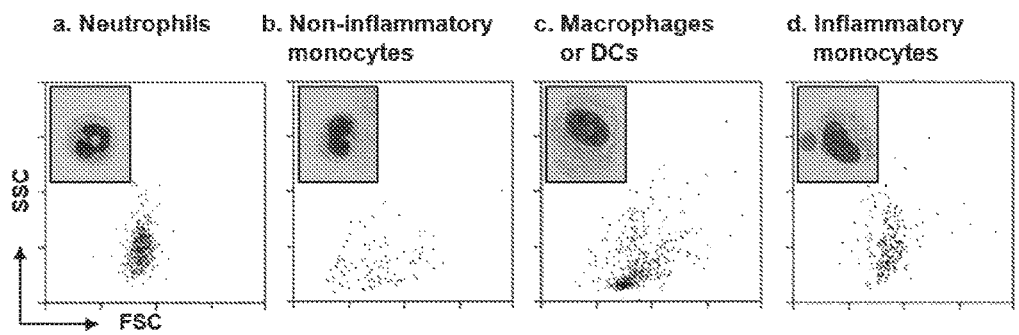
Figure 8C:
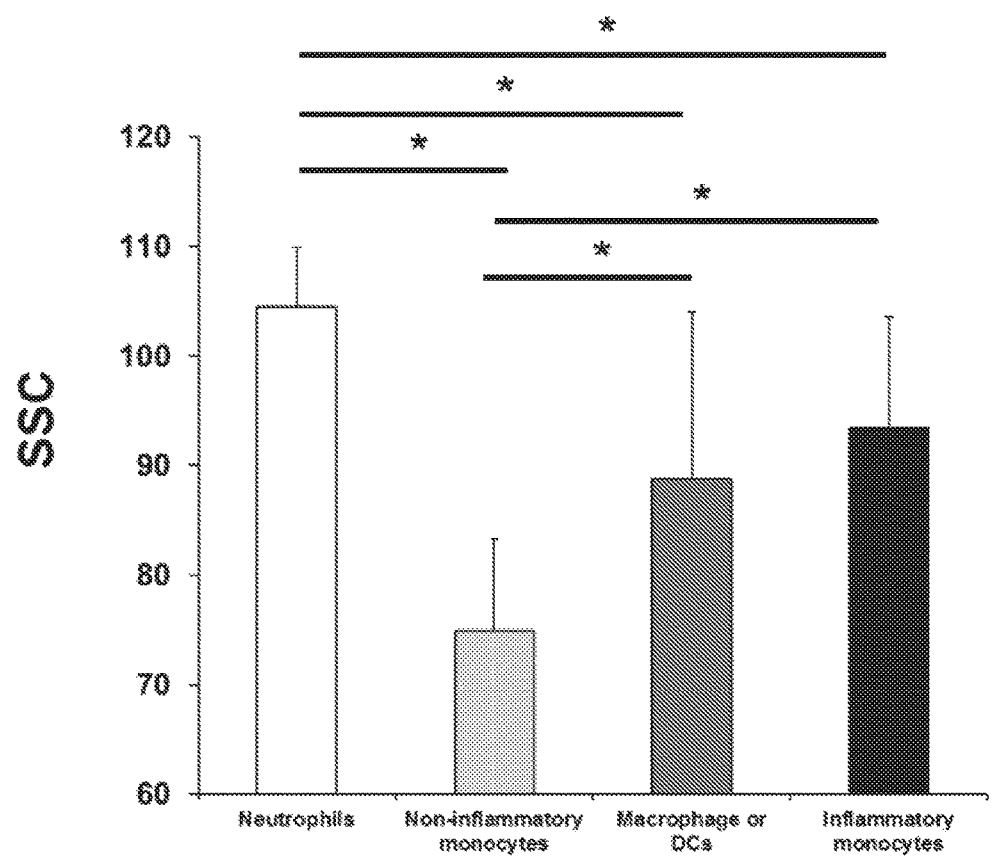

To gain insight into the mechanism of how neutrophils affect IgA responses, B cells from C57BL/6 mice were co-cultured with or without neutrophils from C57BL/6 or IKKβ$^{ΔMye}$ mice for 5 days. The addition of neutrophils from either C57BL/6 or IKKβ$^{ΔMye}$ mice to cultures of B cells did not affect the secretion of IgM or IgG Abs into culture supernatants (FIG. 7B). Interestingly, co-culture with neutrophils significantly reduced the amounts of IgA Abs secreted by B cells and this inhibitory effect was independent of the presence of functional IKKβ in neutrophils (FIG. 7B). Finally, mRNA analysis of B cells co-cultured with neutrophils showed that neutrophils reduced the level of IgA heavy chain transcripts in B cells (FIG. 7C).

Discussion

Recent studies have identified sublingual immunization as a potentially safer alternative to nasal immunization. However, inductive sites for generating immune responses to sublingual immunization, the identity and function of the cells involved, and the signaling pathways for induction of SIgA via this mucosal route are poorly understood. Disclosed herein is the ability of a sublingual vaccine to mount a SIgA response inversely correlates with the presence of neutrophils in sublingual tissue and CLNs. Depletion of Ly6G$^+$ cells improves the development of IgA responses after sublingual immunization and that neutrophils impair the transcription of IgA heavy chain in B cells. This work also shows that myeloid cells lacking IKKβ-dependent NF-κB signaling provide an environment that supports the production of IgA by B cells.

Alum is the most widely used adjuvant for injected vaccines. However, attempts to include alum in mucosal vaccines aimed at prompting SIgA responses have been unsuccessful because this adjuvant fails to effectively induce IgA (Jackson, E. M., et al. PLoS One 7, e41529 (2012)). Studies that addressed mechanisms underlying the adjuvant activity of alum have shown that alum acts via Gr-1 splenic myeloid cells expressing IL-4 to stimulate early B-cell priming (Jordan, M. B., et al. Science 304, 1808-1810 (2004)). Other studies have shown that the NALP3 inflammasome was a crucial element in the adjuvant activity of alum by promoting the maturation of inflammatory cytokines (Eisenbarth, S. C., et al. Nature 453, 1122-1126 (2008)); and furthermore, alum recruits inflammatory monocytes (Kool, M., et al. J. Exp. Med. 205, 869-882 (2008)). In other studies, intranasal co-administration of human neutrophil proteins enhanced antigen-specific serum IgG responses, but failed to promote SIgA responses (Lillard, J. W., et al. Proc. Natl Acad. Sci. USA 96, 651-656 (1999)). These reports are consistent with the disclosed finding that less recruitment of neutrophils into sublingual tissues and CLNs of IKKβ$^{ΔMye}$ mice is a reliable indication of the ability of EdTx as an adjuvant to promote SIgA responses. Because IgG production is not impaired by the recruitment of neutrophils, it is unlikely that neutrophils limit SIgA responses by limiting antigen access to antigen-presenting cells or interactions between the latter and T cells as was previously suggested (Yang, C. W., et al. J. Immunol. 185, 2927-2934 (2010)). Induction of SIgA is well-known to require priming of effector cells in unique inductive sites. Thus, the disclosed finding, that the low proportion of Gr-1$^+$ inflammatory monocytes and/or higher proportion of Gr-1$^-$ non-inflammatory monocytes in the sublingual tissue correlates with induction of broad Ab responses consisting of both serum IgG and SIgA responses, is in agreement with the recent report that neutrophils also control the spread of T-cell responses to distant lymph nodes (Yang, C. W., et al. J. Exp. Med. 210, 375-387 (2013)). The Gr-1$^-$ monocytes, also described as tissue resident myeloid cells, have been classified as alternatively activated macrophages (M2 macrophages) capable of producing IL-10 and TGF-β (Geissmann, F., et al. Immunity 19, 71-82 (2003); Martinez, F. O., et al. Annu. Rev. Immunol. 27, 451-483 (2009)). Interestingly, these two cytokines are central for Ig class switch in B cells and for production of IgA.

Experiments using IKKβ$^{ΔMye}$ mice provided new insights into signaling for the induction of SIgA responses. Previous studies have shown that the NF-κB pathway can mediate both pro- and anti-inflammatory effects (Greten, F. R., et al. Cell 130, 918-931 (2007); Lawrence, T., et al. Nat. Med. 7, 1291-1297 (2001)). The disclosed data suggest that activation of IKKβ-NF-κB signaling in myeloid cells may in fact reduce their capacity to help B cells undergo Ig class switch for production of IgA. This finding is interesting in light of the recent report that the kinase TBK1 in B cells limits IgA class switch by negative regulation of the non-canonical NF-κB pathway (Jin, J., et al. Nat. Immunol. 13, 1101-1109 (2012)). Thus, stimulation of non-canonical NF-κB signaling either directly in B cells or in other antigen-presenting cells could represent a major pathway for induction of IgA Abs. In this regard, IKKβ deficiency in intestinal epithelial cells increases IgA responses induced by CT used as an oral adjuvant (Bonnegarde-Bernard, A., et al. Mucosal Immunol. 7, 257-267 (2014)). The notion that IKKβ can reduce or suppress the functions of macrophages or DCs is consistent with previous studies by others, suggesting that IKKβ may suppress activation of M1 macrophages during infections through inhibition of STAT-1 (Fong, C. H., et al. J. Exp. Med. 205, 1269-1276 (2008)). In those studies, deletion of IKKβ in macrophages increased STAT-1 activation and promoted a shift toward the M1 phenotype, characterized by increased production of pro-inflammatory and inflammatory cytokines, i.e., IL-1β, TNF-α, IL-12 and IFN-γ, and iNOS in response to IP injection of Group B streptococcus or E. coli lipopolysaccharide (Greten, F. R., et al. Cell 130, 918-931 (2007); Fong, C. H., et al. J. Exp. Med. 205, 1269-1276 (2008)). While the disclosed studies showed enhanced antigen-specific Th1 cytokine responses in IKKβ$^{ΔMye}$ mice after sublingual immunization, the most striking observation was the enhanced IL-17 response.

The IKKβ$^{ΔMye}$ mice were useful tools that helped identify the repressive effect of neutrophils on IgA responses. Analysis of chemokine receptors expression by myeloid cell subsets in sublingual tissues revealed a broader expression of CCR2, CXCR2, and LTB4R2 on macrophages/dendritic cell and non-inflammatory monocytes from IKKβ$^{ΔMye}$ mice. One can speculate that this pattern of receptor expression could improve cellular responses to corresponding ligands and facilitate migration to inductive sites and support IgA responses. Injection of alum recruits neutrophils and induces the formation of nodules consistent with those of extracellular DNA traps (Munks, M. W., et al. Blood 116, 5191-5199 (2010)). A recent report showed that the formation of neutrophil extracellular traps requires phosphorylation of p65 NFkB (Lapponi, M. J. et al. J. Pharmacol. Exp. Ther. 345, 430-437 (2013)). However, neutrophil extracellular traps are primarily known to be involved in the killing of pathogens (Branzk, N., et al. Semin. Immunopathol. 35, 513-530 (2013)). Furthermore, the disclosed results showing that neutrophils from both wild-type and IKKβ$^{ΔMye}$ mice suppress transcription of IgA heavy chain suggest the involvement of other mechanisms.

Nasal immunization with the cyclic AMP-inducing adjuvant CT (Datta, S. K., et al. Proc. Natl Acad. Sci. USA 107, 10638-10643 (2010)) or E. coli heat LT-I (Brereton, C. F., et al. J. Immunol. 186, 5896-5906 (2011)) promotes Th17 responses. EdTx as a sublingual adjuvant promotes antigen-specific Th17 responses in spleen, and is associated with in vitro induction of IL-1β and IL-6. The hallmark cytokine produced by Th17 cells is IL-17A (Korn, T., et al. Annu. Rev. Immunol. 27, 485-517 (2009)). Unlike most Th-derived cytokines, IL-17A does not activate JAK-STAT (Gaffen, S. L., et al. Nat. Rev. Immunol. 9, 556-567 (2009)), but engages Act1 leading to activation of IKKβ and downstream NF-κB, C/EBP, and AP-1, which in turn lead to expression of pro-inflammatory cytokines (Maitra, A., et al. Proc. Natl Acad. Sci. USA 104, 7506-7511 (2007), May, M. J. Nat. Immunol. 12, 813-815 (2011)). CD11b$^+$ cells from IKKβ$^{\Delta Mye}$ mice increase specific B-cell populations, i.e., IL-17RA$^{high}$ B cells, and the IL-17RA$^{high}$ B cells express higher levels of surface IgA. IL-17A was reported to act as a helper for the development of germinal centers (Hsu, H. C., et al. Nat. Immunol. 9, 166-175 (2008)). The disclosed results suggest that IKKβ$^{\Delta Mye}$ cells stimulate B cells to be more responsive to IL-17A. This pathway could be one of the mechanisms that rescues the mucosal adjuvant EdTx and the induction of SIgA Abs.

The limited understanding of molecular and cellular mechanisms that regulate IgA responses has hampered the development of safe mucosal vaccines capable to promote mucosal IgA production. Using an experimental vaccine adjuvant that does not normally induce SIgA after sublingual immunization, IKKβ is shown to be one of the key regulatory pathways for induction of SIgA responses by sublingual vaccines. Neutrophils were also shown to negatively regulate IgA production by B cells, an effect that can be countered by Gr-1$^-$ myeloid cells lacking a functional IKKβ. The disclosed results provide new insights for the development of sublingual vaccines that can promote both IgA at mucosal surfaces and IgG in the blood stream for optimal protection against infectious agents.

Example 2: Pharmacological Inhibitors of Neutrophil Function

In this example, the effect of pharmacological inhibitors of neutrophil function was analyzed. These pharmacological inhibitors of neutrophil functions can provide a broad choice of tools that can be incorporated into vaccine formulations in order to induce high levels of IgA responses in mucosal secretions such as saliva, vaginal secretion, the intestinal lumen, and tears. More specifically, the ability of pharmacological agents targeting Gr-1$^+$ cells (i.e., neutrophils) to promote IgA production by B cells in vitro was analyzed. Finally, the pharmacological inhibitors that promote IgA production in vitro were tested to determine if they can elicit generalized IgA responses, including in mucosal secretions, when incorporated into injected or needle-free epicutaneous vaccines.

Several Pharmacological Agents Targeting Gr-1$^+$ Cell Products Functions Promote IgA Production by B Cells In Vitro

TABLE 2

Inhibitors of neutrophil function that were tested

| | Inhibitors | | | |
|---|---|---|---|---|
| | Acetyl-salicylic acid (ASA) | Sivelestat Or ONO 5046 | Sulfasalazine | Roflumilast |
| Function | Cox-2 inhibitor | Neutrophil elastase inhibitor | Neutrophil NET inhibitor | PDE4 inhibitor |
| Current use | Marketed as Aspirin (for pain, fiever, inflammation) | Marketed as Elaspol (for acute respiratory failure) | Marketed as Azulfidine (for Rheumatoid artritis) | Marketed as Daxas or Daliresp (for COPD) |

Spleen cells (2×10$^6$/ml) of naïve C57BL/6 mice were cultured 5 days in the presence of LPS (0.5 µg/ml) alone or LPS with ASA or specific inhibitors of neutrophil functions. The IgA Abs secreted in culture supernatants were quantified by ELISA.

TABLE 3

Effect of pharmacological inhibitors of neutrophil function on IgA production by B cells

| | Acetyl-salicylic acid (ASA) | Sivelestat Or ONO 5046 | Sulfasalazine | Roflumilast |
|---|---|---|---|---|
| Relative stimulation of IgA secretion | ++ | ++ | +++ | + |
| Dose effect (Relative stimulation of IgA) | 10 uM (++) 100 uM (++) 500 uM (+) | 4.6 uM (+) 46 uM (++) 230 uM (++) | 10 uM (++) 100 uM (+++) 1000 uM (+) | 0.062 uM (−) 0.62 uM (−) 6.2 uM (+) |

Relative stimulation of IgA secretion is expressed as the relative level of IgA secreted when compared with cells cultured in the presence of LPS alone.

The Neutrophil Elastase Inhibitor Sivelestat Promotes IgA Responses by a Sublingual Vaccine.

Groups of wild-type C57BL/6 mice were immunized three times at weekly intervals by sublingual application of Yersinia pestis F1-V antigen (50 µg) either alone or in the presence of an edema toxin derivative (15 µg, EdTx), or EdTx plus 100 uM Sulfasalazine. F1-V-specific IgA Ab responses in serum and fecal samples were analyzed by ELISA and end-point titers were expressed as Log$_2$ GMTs.±SD. *p≤0.05 compared with C57BL/6 in each day (n=5).

TABLE 4

Effect of a pharmacological inhibitor of neutrophil function on IgA responses to a sublingual vaccine.

|  | Serum IgG | Serem IgA | Saliva IgA | Fecal IgA |
|---|---|---|---|---|
| F1V alone | 21 ± 0.8 | <5 | <2 | <2 |
| F1V + EdTx | 21 ± 0.1 | <5 | <2 | <2 |
| F1V + EdTx + Sulfasalazine | 22 ± 0.8 | 11 ± 0.6 | 9 ± 0.5 | 6 ± 0.5 |

Example 3: Effect of Neutrophil-Depletion on Antigen-Specific IgA Responses to Epicutaneous Vaccination In this example, the effect of neutrophil depletion on antigen-specific IgA responses to epicutaneous vaccination was examined. Neutrophils were depleted using the 1A8 mAb, given to C57BL/6 mice i.p. on days −3, 4, and 11. The OVA antigen was given by epicutaneous immunization on intact skin (abdomen) using a volume of 100 μl. Mice were divided into three groups: 1) OVA only (1 mg) 2) OVA+ *cholera* toxin (CT, 25 μg) and 3) OVA+*B. anthracis* edema toxin (EdTx: 50 μg of PA+50 μg of EF). Antibody responses in serum and mucosal secretion were examined at days 14, 21, and 28.

Figure 17:
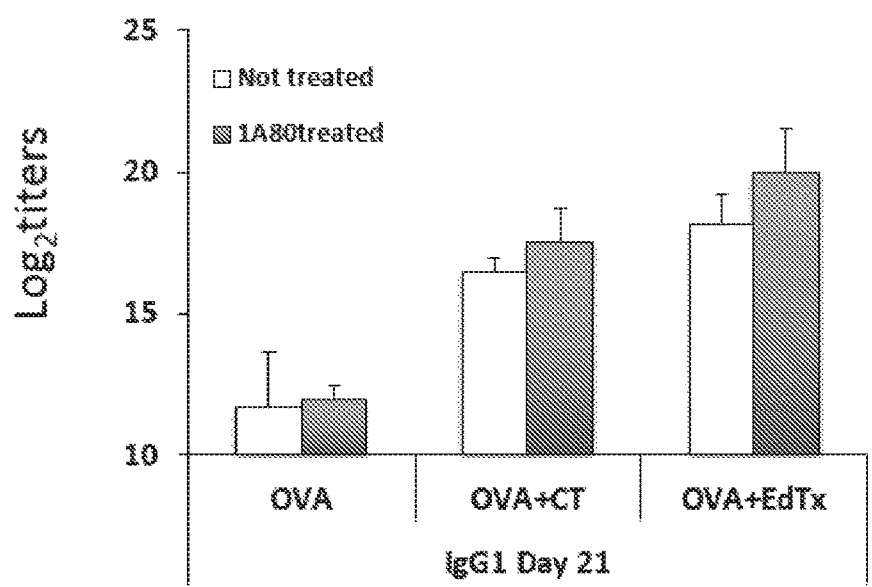
FIG. 17 shows OVA-specific serum IgG1 increases in mice treated with the 1A8 mAb. Neutrophils were depleted using the 1A8 mAb (administered to C57BL/6 mice i.p. on days −3, 4, and 11). The OVA antigen was given by epicutaneous immunization on intact skin (abdomen) using a volume of 100 μl. Mice were divided into three groups: 1) OVA only (1 mg) 2) OVA+cholera toxin (CT, 25 μg) and 3) OVA+B. anthracis edema toxin (EdTx: 50 μg of PA+50 μg of EF). Antibody responses in serum and mucosal secretion were examined at days 14, 21, and 28.
Figure 18:
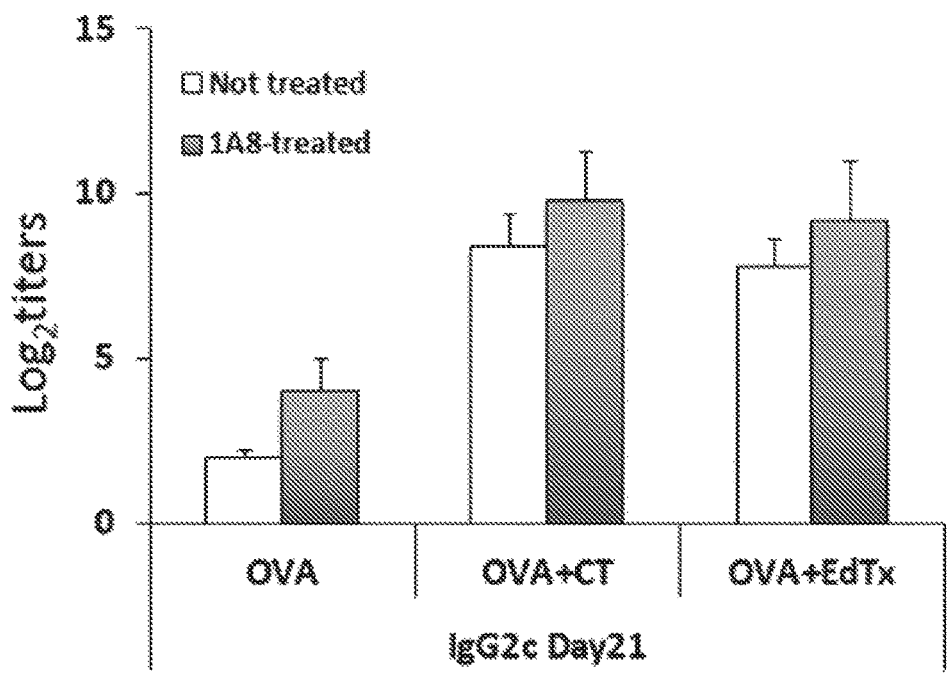
FIG. 18 shows OVA-specific serum IgG2c increases in mice treated with the 1A8 mAb. Neutrophils were depleted using the 1A8 mAb (administered to C57BL/6 mice i.p. on days −3, 4, and 11). The OVA antigen was given by epicutaneous immunization on intact skin (abdomen) using a volume of 100 μl. Mice were divided into three groups: 1) OVA only (1 mg) 2) OVA+cholera toxin (CT, 25 μg) and 3) OVA+B. anthracis edema toxin (EdTx: 50 μg of PA+50 μg of EF). Antibody responses in serum and mucosal secretion were examined at days 14, 21, and 28.

As seen in FIGS. 17 and 18, there was a slight increase in both IgG1 and IgG2c in mice treated with the 1A8 mAb for depletion of neutrophils. There was no change in the IgG1/IgG2c ratio, suggesting there is no major impact on Th2/Th1 responses.

Figure 19:
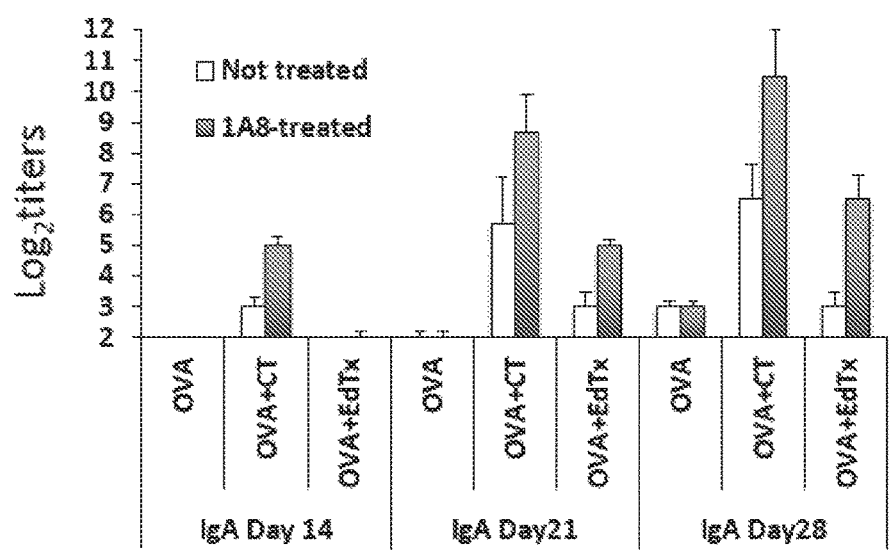
FIG. 19 shows OVA-specific serum IgA increases in mice treated with the 1A8 mAb. Neutrophils were depleted using the 1A8 mAb (administered to C57BL/6 mice i.p. on days −3, 4, and 11). The OVA antigen was given by epicutaneous immunization on intact skin (abdomen) using a volume of 100 μl. Mice were divided into three groups: 1) OVA only (1 mg) 2) OVA+cholera toxin (CT, 25 μg) and 3) OVA+B. anthracis edema toxin (EdTx: 50 μg of PA+50 μg of EF). Antibody responses in serum and mucosal secretion were examined at days 14, 21, and 28.

As seen in FIG. 19, depletion of neutrophils with the 1A8 mAb increased levels of OVA-specific serum IgA responses induced by *cholera* toxin as adjuvant and also led to the development of serum IgA responses in mice immunized with edema toxin as adjuvant.

Figure 20:
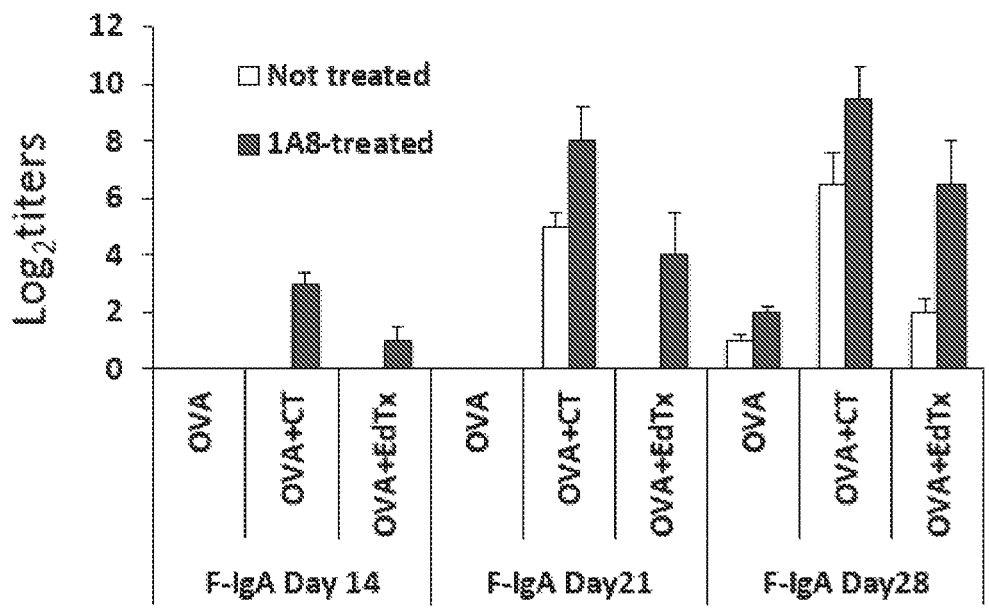
FIG. 20 shows induction of OVA-specific fecal IgA in mice treated with the 1A8 mAb. Neutrophils were depleted using the 1A8 mAb (administered to C57BL/6 mice i.p. on days −3, 4, and 11). The OVA antigen was given by epicutaneous immunization on intact skin (abdomen) using a volume of 100 μl. Mice were divided into three groups: 1) OVA only (1 mg) 2) OVA+cholera toxin (CT, 25 μg) and 3) OVA+B. anthracis edema toxin (EdTx: 50 μg of PA+50 μg of EF). Antibody responses in serum and mucosal secretion were examined at days 14, 21, and 28.

As seen in FIG. 20, depletion of neutrophils with the 1A8 mAb increased levels of fecal IgA (secretory IgA) responses induced by *cholera* toxin as adjuvant and also led to the development of fecal IgA (secretory IgA) responses in response to edema toxin as adjuvant.

Example 4: The Neutrophil Elastase Inhibitor Sivelestat Enhances Systemic IgG and Mucosal IgA Responses Induced by Experimental Vaccine Containing CpG as Adjuvant A vaccine capable of promoting anti-PA Abs in the bloodstream and in the airways may provide better protection against inhalational anthrax than the current injected alum-adsorbed PA-based vaccines. To examine this, a neutrophil elastase inhibitor (sivelestat) was examined in combination with CpG adjuvant to determine its effect on systemic IgG and mucosal IgA responses. C57BL/6 mice were given a nasal immunization of protective antigen of *Bacillus anthracis* (PA) (50 μg/dose given at a volume of 15 μl per nostril) three times at weekly intervals (dasy 0, 7, and 14). CpG adjuvant was administered at 5 μg/dose (CpG ODN 1826).

Mice were divided into four treatment groups: (1) PA only (no Sivelestat) (2) PA+CpG (3) PA+neutrophil elastase inhibitor (Sivelestat) and (4) PA+CpG+neutrophil elastase inhibitor (Sivelestat). Antibody responses in serum and mucosal secretions were examined at days 14, 21, and 28.

Figure 21:
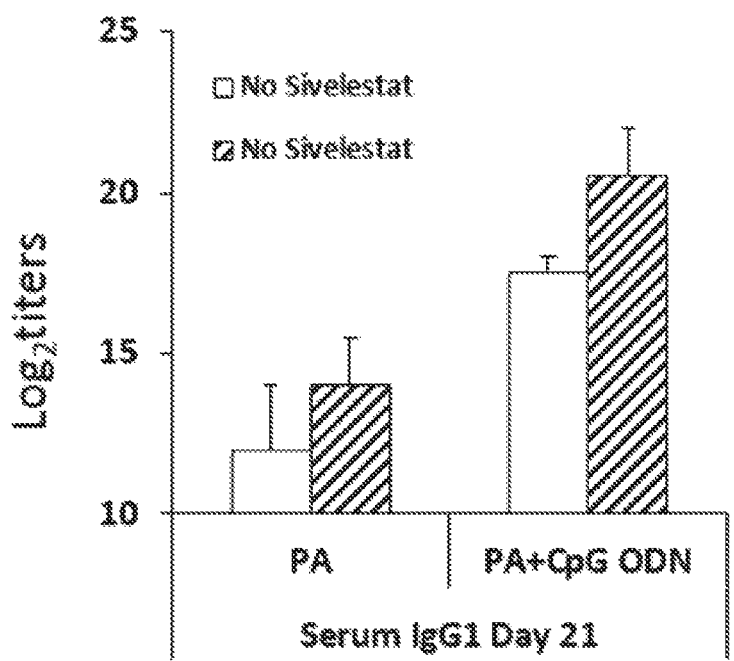
FIG. 21 shows the neutrophil elastase inhibitor sivelestat enhances PA-specific serum IgG1 response induced by experimental vaccine containing CpG as adjuvant. C57BL/6 mice were given a nasal immunization of protective antigen of Bacillus anthracis (PA) (50 μg/dose given at a volume of 15 μl per nostril) three times at weekly intervals (dasy 0, 7, and 14). CpG adjuvant was administered at 5 μg/dose (CpG ODN 1826). Mice were divided into four treatment groups: (1) PA only (no Sivelestat) (2) PA+CpG (3) PA+neutrophil elastase inhibitor (Sivelestat) and (4) PA+CpG+neutrophil elastase inhibitor (Sivelestat). Antibody responses in serum and mucosal secretions were examined at day 21.
Figure 22:
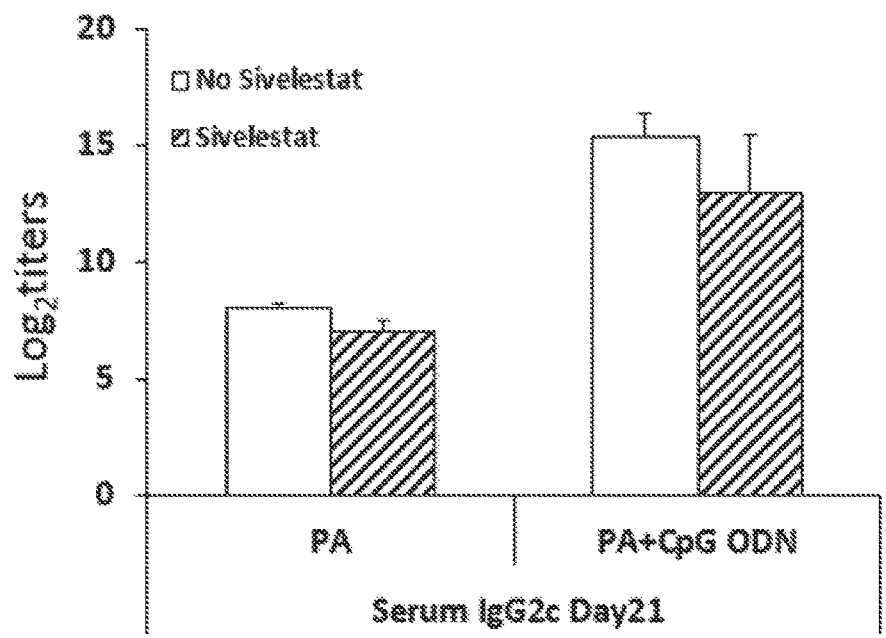
FIG. 22 shows the neutrophil elastase inhibitor sivelestat does not enhance PA-specific serum IgG2c response induced by experimental vaccine containing CpG as adjuvant. C57BL/6 mice were given a nasal immunization of protective antigen of Bacillus anthracis (PA) (50 µg/dose given at a volume of 15 µl per nostril) three times at weekly intervals (dasy 0, 7, and 14). C In some embodiments, the neutrophil elastase inhibitor comprises the protein elafin (peptidase inhibitor 3, skin-derived antileukoprotease (SKALP)), or a functional fragment and/or variant thereof capable of inhibiting neutrophil elastase.
Figure 23:
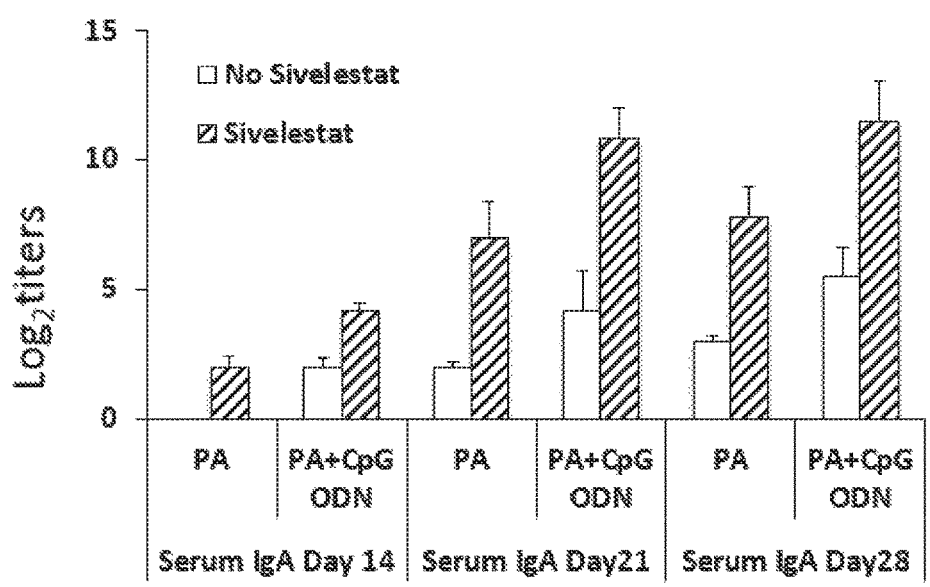
Figure 24:
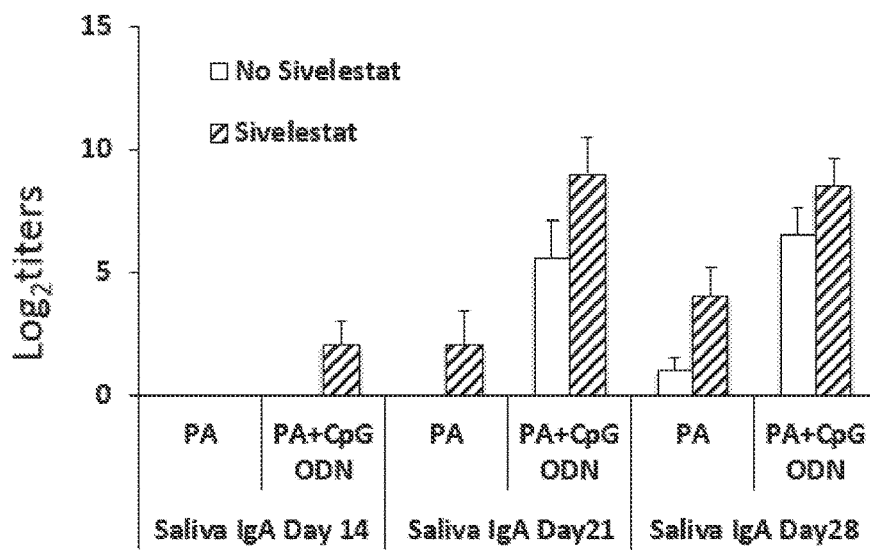
Figure 25:
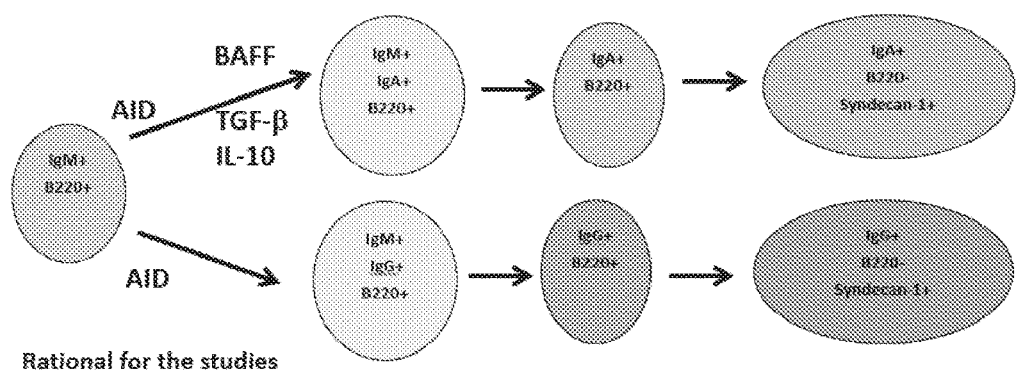
Figure 26A:
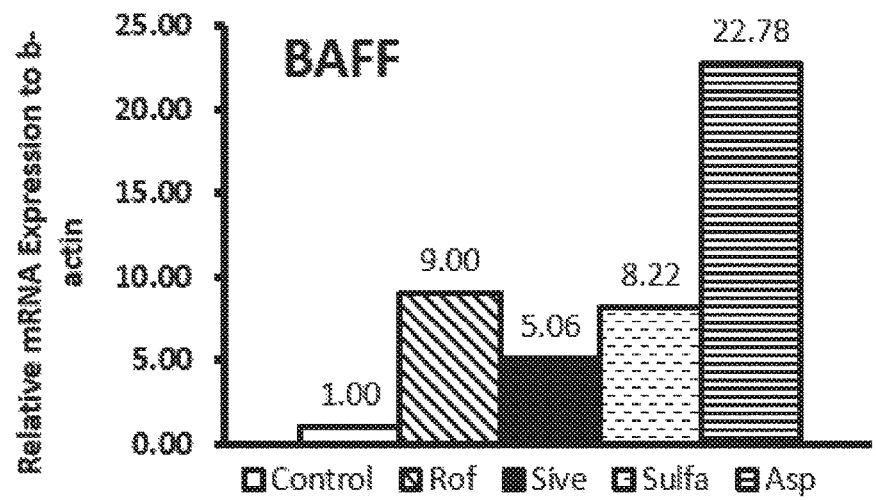
Figure 26B:
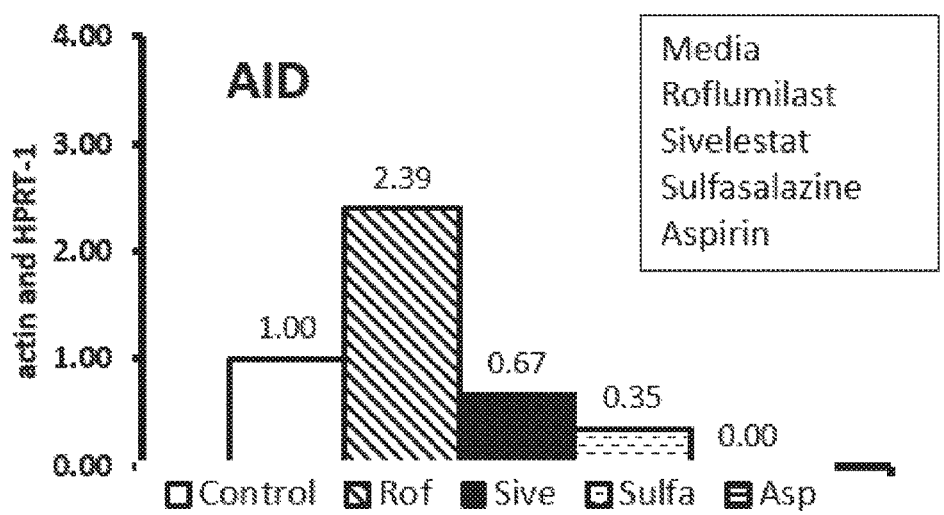
Figure 26C:
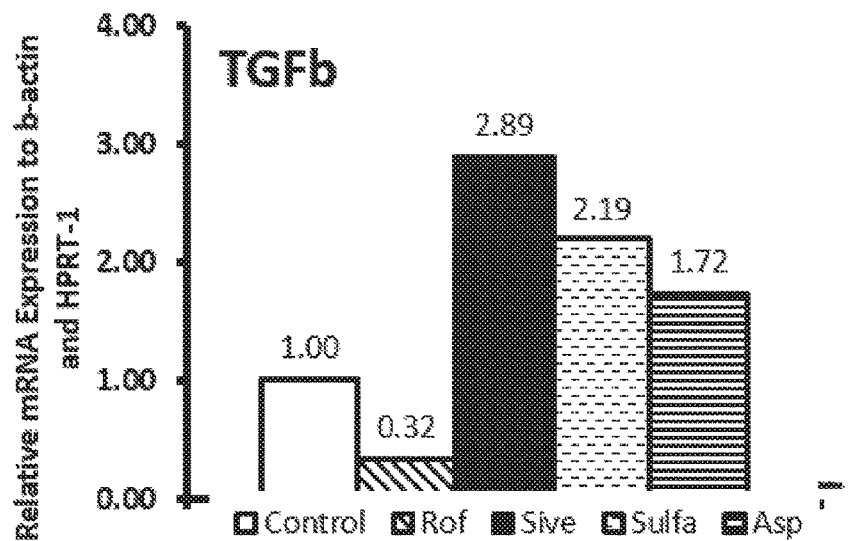
Figure 26D:
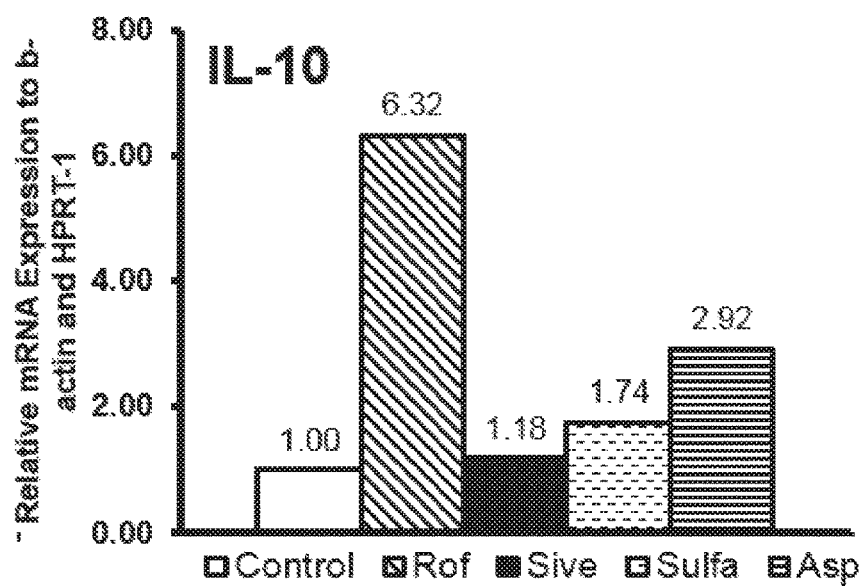

As shown in FIG. 21, sivelestat enhances PA-specific serum IgG1 response. In addition, sivelestat enhances PA-specific serum IgA response (FIG. 23) and PA-specific salivary IgA response (FIG. 24). However, sivelestat did not affect the PA-specific serum IgG2c response (FIG. 22).

Example 5: The Different Inhibitors of Neutrophil Function Differentially Regulate Immunoglobulin Class Switching and Production of IgA Responses In this example, the signaling induced by neutrophil inhibitors were examined to provide insight into mechanisms used to promote immunoglobulin class switching and production of IgG and/or IgA antibodies. In these experiments, the spleen cells of nice mice were cultured 24 hrs without or with neutrophil inhibitor (roflumilast (Phosphodiesterase-4 inhibitor), sivelestat (Neutrophil elastase inhibitor), sulfasalazine (Neutrophil NET inhibitor), or aspirin (COX inhibitor)). Gene expression was analyzed by qRT-PCR for BAFF, AID, TGFb, and IL-10. Mice were divided into 5 groups: (1) Control (Media) (2) Roflumilast (6.5 μM) (3) Sivelestat (46 μM) (4) Sulfasalazine (100 uM) and (5) Aspirin (100 μM).

As seen in FIG. 26, the different neutrophil inhibitors tested (roflumilast, sivelestat, sulfasalazine, and aspirin) differentially regulate genes involved in immunoglobulin class switching (BAFF, AID, TGFb, and IL-10).

In additional experiments, in vitro regulation of Ig class switch and IgG and IgA production by neutrophil inhibitors was examined. Spleen cells of nice mice were cultured for 4 days in the presence of *cholera* toxin B subunit (CT-B) in the presence or absence of a neutrophil inhibitor (roflumilast (6.5 μM), sivelestat (100 μM), sulfasalazine (100 μM), or aspirin (100 μM)). The frequency of IgA secreting cells was analyzed by ELISPOT. Finally, IgG and IgA production were analyzed by immunofluorescence on cytospins.

Figure 27:
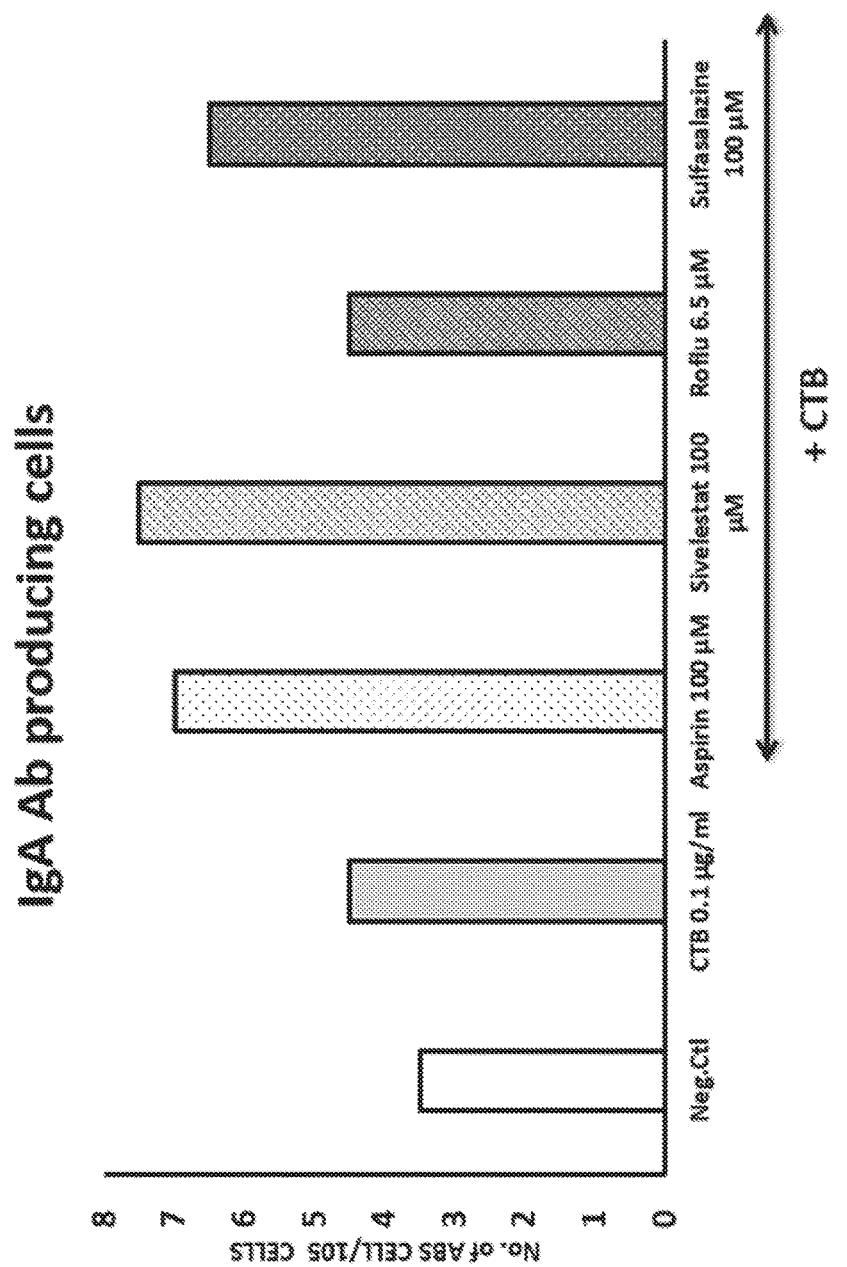

As seen in FIG. 27, the neutrophil inhibitors sivelestat (100 μM), sulfasalazine (100 μM), and aspirin (100 μM)) enhanced IgA secretion by spleen cells in the presence of the adjuvant *cholera* toxin B (CTB) subunit.

Neutrophil inhibitors enhance IgG and IgA secretion by spleen cells cultured in the presence of the adjuvant *cholera* toxin B subunit (CTB). Spleen cells of nice mice were cultured for 4 days in the presence of *cholera* toxin B subunit (CT-B) in the presence or absence of a neutrophil inhibitor (roflumilast (6.5 μM), sivelestat (100 μM), sulfasalazine (100 μM), or aspirin (100 μM)). IgG and IgA production were analyzed by immunofluorescence after staining cytospin samples with FITC-conjugated anti-IgA or PE-conjugated anti-IgG antibodies. Aspirin enhanced IgG and IgA production, while larger increases in IgG and IgA production were seen in spleen cells treated with sivelestat.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A vaccine composition, comprising a vaccine antigen and a neutrophil inhibitor in amounts effective to promote an IgA response to the antigen in a subject, wherein the neutrophil inhibitor comprises sivelestat, alvelestat, elafin, or an inhibitor of phosphodiesterase type 4.

2. The vaccine composition of claim 1 formulated for intranasal administration.

3. The vaccine composition of claim 1 formulated for sublingual or oral administration.

4. The vaccine composition of claim 1 formulated for intramuscular, subcutaneous, or epicutaneous administration.

5. The vaccine composition of claim 1 formulated for intravaginal administration.

6. The vaccine composition of claim 1, wherein the neutrophil inhibitor comprises sivelestat.

7. The vaccine composition of claim 1, wherein the neutrophil inhibitor is an inhibitor of phosphodiesterase type 4.

8. The vaccine composition of claim 1, wherein the vaccine antigen is a viral antigen.

9. An adjuvant composition comprising a neutrophil inhibitor and an additional adjuvant, in an amount effective to promote an IgA response to a vaccine antigen in the subject, wherein the neutrophil inhibitor comprises sivelestat, alvelestat, elafin, or an inhibitor of phosphodiesterase type 4.

10. The adjuvant composition of claim 9 formulated for sublingual or oral administration.

11. The adjuvant composition of claim 9, wherein the additional adjuvant is an aluminium salt, TLR9 agonist, TLR3 agonist, TLR4 agonist, TLR5 agonist, or squalene-based oil-in-water emulsion.

12. A method for enhancing an immune response to a vaccine antigen in a subject, comprising co-administering to the subject the vaccine antigen and a neutrophil inhibitor in an amount effective to promote an IgA response to the vaccine antigen in the subject, wherein the neutrophil inhibitor comprises sivelestat, alvelestat, elafin, or an inhibitor of phosphodiesterase type 4.

13. The method of claim 12, wherein the adjuvant composition is administered sublingually or orally.

14. The method of claim 12, wherein the adjuvant composition induces antigen-specific IgA in the serum and mucosal secretions.

15. The vaccine composition of claim 1, wherein the neutrophil inhibitor comprises alvelestat.

16. The vaccine composition of claim 1, wherein the neutrophil inhibitor comprises elafin.

17. The adjuvant composition of claim 9, wherein the neutrophil inhibitor comprises sivelestat.

18. The adjuvant composition of claim 9, wherein the neutrophil inhibitor comprises alvelestat.

19. The adjuvant composition of claim 9, wherein the neutrophil inhibitor comprises elafin.

20. The adjuvant composition of claim 9, wherein the neutrophil inhibitor is an inhibitor of phosphodiesterase type 4.

* * * * *

SEQUENCE LISTING

<160> NUMBER OF SEQ ID NOS: 7

<210> SEQ ID NO 1
<211> LENGTH: 17
<212> TYPE: PRT
<213> ORGANISM: Artificial Sequence
<220> FEATURE:
<223> OTHER INFORMATION: Synthetic construct

<400> SEQUENCE: 1

Met Lys Lys Ile Ser Ser Val Ile Ala Ile Ala Leu Phe Gly Thr Ile
1               5                   10                  15

Ala

<210> SEQ ID NO 2
<211> LENGTH: 17
<212> TYPE: PRT
<213> ORGANISM: Artificial Sequence
<220> FEATURE:
<223> OTHER INFORMATION: Synthetic construct

<400> SEQUENCE: 2

Val Ile Ala Ile Ala Leu Phe Gly Thr Ile Ala Thr Ala Asn Ala Ala
1               5                   10                  15

Asp

<210> SEQ ID NO 3
<211> LENGTH: 17
<212> TYPE: PRT
<213> ORGANISM: Artificial Sequence
<220> FEATURE:
<223> OTHER INFORMATION: Synthetic construct

<400> SEQUENCE: 3

His Gln Phe Thr Thr Lys Val Ile Gly Lys Asp Ser Arg Asp Phe Asp
1               5                   10                  15

Ile

<210> SEQ ID NO 4
<211> LENGTH: 17
<212> TYPE: PRT
<213> ORGANISM: Artificial Sequence
<220> FEATURE:
<223> OTHER INFORMATION: Synthetic construct

<400> SEQUENCE: 4

Val Ile Gly Lys Asp Ser Arg Asp Phe Asp Ile Ser Pro Lys Val Asn
1               5                   10                  15

Gly

<210> SEQ ID NO 5
<211> LENGTH: 17
<212> TYPE: PRT
<213> ORGANISM: Artificial Sequence
<220> FEATURE:
<223> OTHER INFORMATION: Synthetic construct

<400> SEQUENCE: 5

Arg Asp Phe Asp Ile Ser Pro Lys Val Asn Gly Glu Asn Leu Val Gly
1               5                   10                  15

Asp

<210> SEQ ID NO 6

```
<211> LENGTH: 21
<212> TYPE: DNA
<213> ORGANISM: Artificial Sequence
<220> FEATURE:
<223> OTHER INFORMATION: Synthetic construct

<400> SEQUENCE: 6
agctggtaaa gcctggggcc t                                              21

<210> SEQ ID NO 7
<211> LENGTH: 23
<212> TYPE: DNA
<213> ORGANISM: Artificial Sequence
<220> FEATURE:
<223> OTHER INFORMATION: Synthetic construct

<400> SEQUENCE: 7
cggtgactga ggttccttga ccc                                            23
```